(12) United States Patent
Gazit

(10) Patent No.: US 7,781,396 B2
(45) Date of Patent: *Aug. 24, 2010

(54) PEPTIDES DIRECTED FOR DIAGNOSIS AND TREATMENT OF AMYLOID-ASSOCIATED DISEASE

(75) Inventor: Ehud Gazit, Ramat-HaSharon (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 132 days.

This patent is subject to a terminal disclaimer.

(21) Appl. No.: 11/471,657

(22) Filed: Jun. 21, 2006

(65) Prior Publication Data

US 2006/0234947 A1  Oct. 19, 2006

Related U.S. Application Data

(63) Continuation-in-part of application No. 10/562,852, filed as application No. PCT/IL2004/000577 on Jun. 29, 2004, said application No. 10/562,852 is a continuation-in-part of application No. 10/901,243, filed on Jul. 29, 2004, now abandoned, which is a continuation-in-part of application No. PCT/IL03/000079, filed on Jan. 30, 2003, which is a continuation of application No. 10/235,852, filed on Sep. 6, 2002, now abandoned.

(60) Provisional application No. 60/483,180, filed on Jun. 30, 2003, provisional application No. 60/514,974, filed on Oct. 29, 2003, provisional application No. 60/352,578, filed on Jan. 31, 2002, provisional application No. 60/392,266, filed on Jul. 1, 2002, provisional application No. 60/436,453, filed on Dec. 27, 2002.

(51) Int. Cl.
*A61K 38/00* (2006.01)
(52) U.S. Cl. ......................................................... 514/2
(58) Field of Classification Search ........................ None
See application file for complete search history.

(56) References Cited

U.S. PATENT DOCUMENTS

| | | |
|---|---|---|
| 2,920,080 A | 1/1960 | Bucourt et al. |
| 3,042,685 A | 3/1962 | Roussel |
| 3,625,973 A | 12/1971 | Julia |
| 3,790,596 A | 2/1974 | Shkilkova et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,976,639 A | 8/1976 | Batcho et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,873,316 A | 10/1989 | Meade et al. |
| 4,879,219 A | 11/1989 | Wands et al. |
| 4,925,673 A | 5/1990 | Steiner et al. |
| 4,946,778 A | 8/1990 | Ladner et al. |
| 4,970,233 A | 11/1990 | McHugh |
| 5,011,771 A | 4/1991 | Bellet et al. |
| 5,013,556 A | 5/1991 | Woodle et al. |
| 5,192,659 A | 3/1993 | Simons |
| 5,270,163 A | 12/1993 | Gold et al. |
| 5,272,057 A | 12/1993 | Smulson et al. |
| 5,281,521 A | 1/1994 | Trojanowski |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,556,744 A | 9/1996 | Weiner et al. |

(Continued)

FOREIGN PATENT DOCUMENTS

DE    3412445    10/1985

(Continued)

OTHER PUBLICATIONS

Pispisa et al., Biopolymers 53: 169-181, 2000.*

(Continued)

*Primary Examiner*—Jeffrey Stucker
*Assistant Examiner*—Aditi Dutt

(57) ABSTRACT

Peptides having at least 2 amino acids and no more than 15 amino acids are provided. The peptides comprise amino acid sequence X-Y or Y-X, wherein X is an aromatic amino acid and Y is any amino acid other than glycine. Also provided are pharmaceutical compositions and kits including such peptides as well as methods using same for diagnosing and treating amyloid associated diseases.

2 Claims, 47 Drawing Sheets
(15 of 47 Drawing Sheet(s) Filed in Color)

U.S. PATENT DOCUMENTS

| | | | |
|---|---|---|---|
| 5,567,588 | A | 10/1996 | Gold et al. |
| 5,569,825 | A | 10/1996 | Lonberg et al. |
| 5,595,877 | A | 1/1997 | Gold et al. |
| 5,625,126 | A | 4/1997 | Lonberg et al. |
| 5,633,425 | A | 5/1997 | Lonberg et al. |
| 5,637,459 | A | 6/1997 | Burke et al. |
| 5,643,768 | A | 7/1997 | Kawasaki |
| 5,658,754 | A | 8/1997 | Kawasaki |
| 5,659,041 | A | 8/1997 | Pollak et al. |
| 5,661,016 | A | 8/1997 | Lonberg et al. |
| 5,683,867 | A | 11/1997 | Biesecker et al. |
| 5,688,561 | A | 11/1997 | Ichikawa et al. |
| 5,705,337 | A | 1/1998 | Gold et al. |
| 5,916,642 | A | 6/1999 | Chang |
| 6,162,828 | A | 12/2000 | Fukuda et al. |
| 6,251,625 | B1 | 6/2001 | Bommarius et al. |
| 6,255,286 | B1 | 7/2001 | Yanai et al. |
| 6,261,569 | B1 | 7/2001 | Comis et al. |
| 6,303,567 | B1 | 10/2001 | Findeis et al. |
| 6,309,669 | B1 | 10/2001 | Setterstrom et al. |
| 6,326,174 | B1 | 12/2001 | Joyce et al. |
| 6,359,112 | B2 | 3/2002 | Kapurniotu et al. |
| 6,361,861 | B2 | 3/2002 | Gao et al. |
| 6,593,339 | B1 | 7/2003 | Eek et al. |
| 6,610,478 | B1 | 8/2003 | Takle et al. |
| 6,613,875 | B1 | 9/2003 | Ghadiri |
| 6,617,114 | B1 | 9/2003 | Fowlkes et al. |
| 6,677,153 | B2 | 1/2004 | Iversen |
| 6,689,753 | B1 | 2/2004 | Soto-Jara |
| 6,762,331 | B2 | 7/2004 | Hong et al. |
| 6,858,318 | B2 | 2/2005 | Kogiso et al. |
| 6,976,639 | B2 | 12/2005 | Williams et al. |
| 7,045,537 | B1 | 5/2006 | Woolfson et al. |
| 2001/0041732 | A1 | 11/2001 | Gurley et al. |
| 2002/0006954 | A1 | 1/2002 | Hensley et al. |
| 2002/0086067 | A1 | 7/2002 | Choi et al. |
| 2002/0151506 | A1 | 10/2002 | Castillo et al. |
| 2003/0130484 | A1 | 7/2003 | Gordon et al. |
| 2003/0144185 | A1 | 7/2003 | McGimpsey |
| 2003/0158237 | A1 | 8/2003 | Saragovi et al. |
| 2003/0225155 | A1 | 12/2003 | Fernandez-Pol et al. |
| 2004/0001893 | A1 | 1/2004 | Stupp et al. |
| 2004/0029830 | A1 | 2/2004 | Herbert |
| 2004/0052928 | A1 | 3/2004 | Gazit |
| 2004/0152672 | A1 | 8/2004 | Carson et al. |
| 2005/0020809 | A1 | 1/2005 | Gazit |
| 2005/0069570 | A1 | 3/2005 | Haynie |
| 2006/0079454 | A1 | 4/2006 | Reches et al. |
| 2006/0079455 | A1 | 4/2006 | Gazit et al. |
| 2006/0089380 | A1 | 4/2006 | Barnham et al. |
| 2006/0194777 | A1 | 8/2006 | Gazit et al. |
| 2006/0234947 | A1 | 10/2006 | Gazit |
| 2007/0021345 | A1 | 1/2007 | Gazit |
| 2007/0135334 | A1 | 6/2007 | Gazit |
| 2007/0298043 | A1 | 12/2007 | Gazit et al. |
| 2008/0009434 | A1 | 1/2008 | Reches et al. |
| 2008/0194667 | A1 | 8/2008 | Gazit et al. |

FOREIGN PATENT DOCUMENTS

| | | |
|---|---|---|
| DE | 10043282 | 3/2002 |
| EP | 0081122 | 6/1983 |
| EP | 0264166 | 4/1988 |
| EP | 0421946 | 4/1991 |
| EP | 0885904 | 6/1998 |
| EP | 0885904 | 3/2004 |
| EP | 966975 | 7/2005 |
| FR | 1373316 | 9/1964 |
| JP | 59-044313 | 3/1984 |
| JP | 60-040061 | 2/1985 |
| JP | 63-044895 | 2/1988 |
| JP | 02-295923 | 6/1990 |
| JP | 10-245342 | 9/1998 |
| JP | 2000-193661 | 7/2000 |
| JP | 2001-504334 | 4/2001 |
| WO | WO 80/00789 | 5/1980 |
| WO | WO 92/19253 | 11/1992 |
| WO | WO 97/16191 | 9/1997 |
| WO | WO 98/20135 | 5/1998 |
| WO | WO 99/42102 | 8/1999 |
| WO | WO 99/58652 | 11/1999 |
| WO | WO 00/24390 | 4/2000 |
| WO | WO 01/05421 | 1/2001 |
| WO | WO 01/10457 | 2/2001 |
| WO | WO 01/45726 | 6/2001 |
| WO | WO 01/49281 | 7/2001 |
| WO | WO 01/49307 | 7/2001 |
| WO | WO 01/93836 | 12/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/070269 | 8/2003 |
| WO | WO 03/077866 | 9/2003 |
| WO | WO 2004/052773 | 6/2004 |
| WO | WO 2005/016339 | 2/2005 |
| WO | WO 2005/020809 | 3/2005 |
| WO | WO 2005/027901 | 3/2005 |
| WO | WO 2005/085867 | 9/2005 |
| WO | WO 2006/006172 | 1/2006 |
| WO | WO 2006/018850 | 2/2006 |
| WO | WO 2006/020681 | 2/2006 |
| WO | WO 2006/027780 | 3/2006 |
| WO | WO 2006/013552 | 9/2006 |
| WO | WO 2007/029003 | 3/2007 |
| WO | WO 2007/043048 | 4/2007 |

OTHER PUBLICATIONS

Tsai et al., 218th ACS National Meeting, New Orleans, Aug. 22-26, 1999, Meeting abstract—MEDI-018.*

Tsai et al. 218th ACS National Meeting, New Orleans, Aug. 22-26, 1999, Meeting abstract—MEDI-018.*

Appukkuttan et al. "Microwave Enhanced Formation of Electron Rich Arylboronates", Synlett, 8: 1204-1206, 2003. Figs. Scheme 4, Compounds 5A, 5B, 5C, 5D.

Beugelmans Database Crossfire Beilstein [Online], Beilstein Institut zur F?rderung der Chemischen Wissenschaften, Frankfurt am Main, DE, Database Accession No. 116671 (BRN) Compounds INDOL-2-YL-Methanol & Beugelmans R.: Bulletin de la Soci?t? Chimique Fran?aise, p. 335-336, 1969.

Cohen et al "Inhibition of Amyloid Fibril Formation and Cytotoxicity by Hydroxyindole Derivatives", Biochemistry, 45: 4727-4735, 2006. Abstract, p. 4728, col. 1, Last §, p. 4728, col. 2, § 2, Fig.1, p. 4729, col. 1, p. 4728, col. 1, Last §, p. 4728, col. 2, § 2, Fig.1, p. 4728, col. 1, Last §, p. 4728, col. 2, § 2, Fig.1, 4, p. 4732, col. 2, § 2,3, p. 4733, col. 2, § 4.

Altland et al. "Potential Treatment of Transthyretin-Type Amyloidoses by Sulfite", Neurogenetics, 2: 183-188, 1999.

Azriel et al. "Analysis of the Minimal Amyloid-Forming Fragment of the Islet Amyloid Polypeptide", The Journal of Biological Chemistry, 276(36): 34156-34161, 2001.

Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.

Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.

Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.

Kocisko et al. "New Inhibitors of Scrabie-Associated Prion Protein Formation in A Library of 2,000 Drugs and Natural Products", Journal of Virology, 77(19): 10288-10294, 2003.

Lashuel et al. "New Class of Inhibitors of Amyloid-? Fibril Formation. Implications for the Mechanism of Pathogenesis in Alzheimer's Disease", The Journal of Biological Chemistry, 277(45):42881-42890, 2002.

Oza et al. "Synthesis and Evaluation of Anthranilic Acid-Based Transthyretin Amyloid Fibril Inhibitors", Bioorganic & Medicinal Chemistry Letters, 9: 1-6, 1999.

Peterson et al. "Inhibiting Transthyretin Conformational Chamges That Lead to Amyloid Fibril Formation", Proc. Natl. Acad. Sci. USA, 95: 12956-12960, 1998.

Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.

Gazit "A Possible Role for 'Phi'-Stacking in the Self-Assembly of Amyloid Fibrils", The FASEB Journal, 16: 77-83, 2002.

Soto et al. Beta-Sheet Breaker Peptides Inhibit Fibrillogenesis in A Rat Brain Model of Amyloidosis: Implications for Alzheimer's Therapy, Nature Medicine, 4(7): 822-826, 1998.

Inglot "Comparison of the Antiviral Activity In Vitro of Some Non-Steroidal Anti-Inflammatory Drugs", Journal of General Virology, 4(2): 203-214, 1969.

Pavia et al. "Antimicrobial Activity of Nicotine Against A Spectrum of Bacterial and Fungal Pathogens", Journal of Medical Microbiology, 49(7): 675-676, 2000.

Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.

Lee et al. "Anti-Diabetic Constituent From the Node of Lotus Rhizome (Nelumbo Nucifera Gaertn)", Natural Product Sciences, 7(4), 107-109, 2001. p. 108, col. 1, Last §—col. 2, § 1.

Honma et al. "Use of A Thromboxane A2 Antagonist or Synthase Inhibitor for Treating Central Nervous System Diseases, e.g. Alzheimer Type Dementia." Database WPI, Section Ch. Week 200039, Derwent Publications, AN 2000-451668. & WO 00/30683 (Yagami et al.), Jun. 2, 2000. Abstract.

Losert et al. "Effect of Indole 3 Alkanecarboxylic Acifs on Glucose Utilization in Rats" Arzneimittel-Forschung/Drug Research, 25(6): 880-887, 1975. p. 880, col. 1, § 6, p. 886, col. 2, § 4, 5, p. 887, col. 1, § 3.

Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, AN 2003-286683 & RU 2196568 C1 (Kiselev) Jan. 20, 2003. Abstract.

Kon-Ya et al "Indole Derivatives as Potent Inhibitors of Larval Settlement by the Barnacle, Balanus Amphitrite", Bioscience Biotechnology Biochemistry, JP, 58(12): 2178-2181, 1994. Compound 102.

Booth et al. "Instability, unfolding and aggregation of human lysozyme variants underlying amyloid fibrilloagenesis", Nature. Feb. 27, 1997;385(6619):787-93.

Glener, GG, "Amyloid deposits and amyloidosis. The beta-fibrilloses (first of two parts)". N Engl J Med. Jun. 5, 1980:302(23):1283-92.

Ferrannini, E., "Insulin resistance versus insulin deficiency in non-insulin-dependent diabetes mellitus: problems and prospects". Endocr Rev. Aug. 1998;19(4):477-90.

Westermark, P., "Amyloid and Polypeptide Hormones: Whatbis their Interrelationship?", Amyloid,: Int. J. Exp. Clin. Invest., 1994, 1:47-60.

Westermark et al, "Islet amyloid polypeptide: pinpointing amino acid residues linked to amyloid fibril formation", Proc Natl Acad Sci U S A. Jul. 1990;87(13):5036-40.

Johnson et al, "Islet amyloid, islet-amyloid polypeptide, and diabetes mellitus", N Engl J Med. Aug. 24, 1989;321(8):51:-8.

Mosselman et al, "Islet amyloid polypeptide: identification and chromosomal localization of the human gene", FEBS Lett. Nov. 7, 1988;239(2):227-32.

Moriarty et al, "Effects of sequential proline substitutions on amyloid formation by human amylin20-29", Biochemistry. Feb. 9, 1999;38(6):1811-8.

Hoppener et al, "Islet amyloid and type 2 diabetes mellitus", N Engl J Med. Aug. 10, 2000;343(6):411-9.

Seino S; Study Group of Comprehensive Analysis of Genetic Factors in Diabetes Mellitus, "S20G mutation of the amylin gene is associated with Type II diabetes in Japanese. Study Group of Comprehensive Analysis of Genetic Factors in Diabetes Mellitus", Diabetologia. Jul. 2001;44(7:906-9.

Gillmore et al, "Amyloidosis: a review of recent diagnostic and therapeutic development", Br J Haematol. Nov. 1997;99(2):245-56.

Kilkarni et al, "Investigation of the effects of antisense oligodeoxynucleotides to islet amyloid polypeptide mRNA on insulin release, content and expression", J Endocrinol. Dec. 1996;151(3):341-8.

Novials et al, "Reduction of islet amylin expression and basal secretion by adenovirus-mediated delivery of amylin antisense cDNA", Pancreas. Aug. 1998;17(2):182-6.

Kahn et al, "Islet amyloid: a long-recognized but underappreciated pathological feature of type 2 diabetes", Diabetes. Feb. 1999;48(2):241-53.

Merlini et al, "Interactions of the anthracycline 4'-iodo-4'-deoxydoxorubicin with amyloid fibrils: inhibition of amyloidogenesis", Proc Natl Acad Sci U S A. Mar. 28, 1995;92(7):2959-63.

Tenidis et al, "Identification of a penta- and hexapeptide of islet amyloid polypeptide (IAPP) with amyloidogenic and cytotoxic properties", J Mol Biol. Jan. 28, 2000;295(4):1055-71.

Kuner et al, "Controlling polymerization of beta-amyloid and prion-derived peptides with synthetic small molecule ligands". J Biol Chem. Jan. 21, 2000:275(3):1673-8.

Findeis, MA. "Approaches to discovery and characterization of inhibitors of amyloid beta-peptide polymerization", Biochim Biophys Acta. Jul. 26, 2000;1502(1 :76-84.

Wilesmith et al, "Bovine spongiform ercephalopathy". Curr Top Microbiol Immunol. 1991;172:21-38.

Gajdusek, DC, "Unconventional viruse: and the origin and disappearance of kuru", Science. Sep. 2, 1977:197(4307):943-60.

Medore et al, "Fatal familial insomnia, prion disease with a mutation at codon 178 of the protein gene", N Engl J Med. Feb. 13, 1992:326(7):444-9.

Pinkert et al, "An albumin enhancer located 10 kb upstream functions along with its promoter to direct efficient, liver-specific expression in transgenic mice", Genes Dev. May 1987;1(3):268-76.

Calame et al, "Transcriptional controlling elements in the immunoglobulin and T cell receptor loci", Adv Immunol. 1988;43:235-75.

Winoto et al. "A novel, inducible and T cell-specific enhancer located at the 3' end of the T cell receptor alpha locus", EMBO J. Mar. 1989;8(3):729-33.

Banerji et al, "A lymphocyte-specific cellular enhancer is located downstream of the joining region in immunoglobulin heavy chain genes", Cell. Jul. 1983;33(3):729-40.

Byrne et al, "Multiplex gene regulation a two-tiered approach to transgene regulation in transgenic mice", Proc Natl Acad Sci U S A. Jul. 1989;86(14):5473-7.

Edlund et al, "Cell-specific expression of the rat insulin gene: evidence for role of two distinct 5' flanking elements", Science. Nov. 22, 1985;230(4728):912-6.

Bursavich et al, "Designing non-peptide peptidomimetics in the 21st century: inhibitors targeting conformational ensembles", J Med Chem. Jan. 3, 2002:;45(3):541-58.

Baltzer et al, "De novo design of proteins—what are the rules?", Chem Rev. Oct. 2001;101(10):3153-63.

Orlandi et al, "Cloning immunoglobulin variable domains for expression by the polymerase chain reaction", Proc. Natl Acad. 86:3833-383:1984.

Winter et al, "Man-made antibodies", Nature. Jan. 24, 1991;349(6307):293-9.

Kohler et al, "Continuous cultures of fused cells secreting antibody of predefined specificity", 1975. *Biotechnology*. 1992;24:524-6.

Kozbor et al, "Specific immunoglobulin production and enhanced tumorigenicity following ascites growth of human hybridomas", *J Immunol Methods*. Jul. 16, 1985;81(1):31-42.

Cote et al, "Generation of human monoclonal antibodies reactive with cellular antigens", *Proc Natl Acad Sci U S A*. Apr. 1983:80(7):2026-30.

Cole et al, "Human monoclonal antibodies", *Mol Cell Biochem*. Jun. 1984;62(2):109-20.

Han et al, "Technetium Complexes for the Quantitation of Brain Amyloid", *J Am Chem Soc*, 1996, 118:4506-4507.

Sambrook et al, "Molecular Cloning: A Laboratory Manual", $2^{nd}$ Ed., Cold Spring Harbor Laboratory Press. 1989. Table of Contents.

"Current Protocols in Molecular Biology", Ausubel et al, Eds. vol. 1 (Supp. 63), John Wiley & Sons, Inc. Table of Contents.

Perbal, B.. "A Practical Guide to Molecular Cloning", John Wiley & Sons, Table of Contents.

Stites et al, Eds., "Basic & Clinical Immunology", $8^{th}$ ED., Prentice-Hall Int. Inc., Table of Contents.

Gait, MJ, Ed., "Oligonucleotide Synthesis a Practical Approach", IRL Press, Table of Contents.

Freshney, RI, ED., "Animal Cell Culture a Practical Approach", IRL Press, Table of Contents.

Marshak et al, Eds., "Strategies for Protein Purification and Characterization, A Laboratory Course Manual", Cold Spring Harbor Laboratory Press, 1996, Table of Contents.

Cooper MB, "Selective amyloid staining as a function of amyloid composition and structure. Histochemical analysis of the alkaline Congo red, standardized toluidine blue, and iodine methods", *Lab Invest*. Sep. 1974;31(3):232-8.

Database, Accession No. AAW93015, 1991.

Database, Accession No. S04016, 1993.

Gorman et al, "Alzheimer β-Amyloid Peptides, Structures Of Amyloid Fibrils And Alternate Aggregation Products", *Biopolymers*, 60: 381-394, 2001.

Kazumi Kon-Ya et al "Indole Derivatives as Potent Inhibitors of Larval Settlement by the Barnacle, Balanus Amphitrite", Bioscience Biotechnology and Agrochem, Tokyo, JP, vol. 58, No. 12, 1994, pp. 2178-2181 XP008064229—ISSN: 0916-8451, compound 102.

Beugelmans Database Crossfire Beilstein [Online], Beilstein Institute zur Foerderung der Chemischen Wissenschaften, Frankfurt am Main, DE; Database Accession No. 116671 (BRN) Compounds INDOL-2-YL-Methanol & Beugelmans R.: Bull. Soc. Chim. Fr., p. 335-336, 1969.

Gazit "Global Analysis of Tandem Aromatic Optapeptide Repeats: The Significance of the Aroma-glycine Motif", Bioinformatics Discovery Note, 18(6): 880-883, 2002.

Gazit "The 'Correctly Folded' State of Proteins: Is it a Metastable State?", Angew. Chem. Int. Ed.,41(2): 257-259, , 2002.

Gorman et al. "Alzheimer β-Amyloid Peptides, Structures Of Amyloid Fibrils And Alternate Aggregation Products", Biopolymers, 60: 381-394, 2001. Claims: 1-16, 22-26, 70-80, 91-100.

Database, Accession No. AAW93015, 1991. Claims: 1-16, 22-26.

Database, Accession No. S04016, 1993. Claims: 1-16, 22-26.

Gazit "A Possible Role for 'Phi'-Stacking in the Self-Assembly of Amyloid Fibrils", FASEB: 77- .

Coughlan et al. "Factors Influencing the Processing and Function of the Amyloid Beta Precursor Protein—A Potential Therapeutic Target in Alzheimer's Disease?", Pharmacology and Therapeutics 86: 111-144, 2000.

Damas et al. "Review: TTR Amyloidosis—Structural Features Leading to Protein Aggregation and Their Implications on Therapeutic Strategies", Journal of Structural Biology, 130: 290-299, 2000.

Gazit "Mechanistitc Studies of The Process of Amyloid Fibrils Formation by The Use of Peptide Fragments and Analogues: Implications of the Design of Fibrillization Inhibitors", Current Medicinal Chemistry, 9,: 1667-1675, 2002.

Mazor et al. "Idendification and Characterization of a Novel Molecular-Recognition and Self-Assembly Domain Within the Islet Amyloid Polypeptide", Journal of Molecular Biology, 322: 1013-1024, 2002.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1):68-76, 2000.

Anguiano et al. "Protofibrillar Islet Amyloid Polypeptide Permeabilizes Synthetic Vesicles by A Pore-Like Mechnaism That May Be Relevant to Type II Diabetes", Biochemistry, 41: 11338-11343, 2002.

Arvinte et al. "The Structure and Mechanism of Formation of Human Calcitonin Fibrils", The Journal of Biological Chemistry, 268(9): 6415-6422, 1993.

Austin et al. "Medical Progress: Calcitonin. Physiology and Pathophysiology", The New England Journal of Medicine, 304(5): 269-278, 1981.

Balaram "De Novo Design: Backbone Conformational Constraints in Nucleating Helices and β-Hairpins", Journal of Peptide Research, 54: 195-199, 1999.

Balbach et al. "Supramolecular Structure in Full-Length Alzheimer's β-Amyloid Fibrils: Evidence for A Parallel β-Sheet Organization From Solid-State Nuclear Magnetic Resonance", Biophysical Journal, 83: 1205-1216, 2002.

Bauer et al. "Interfacial Adsorption and Aggregation Associated Changes in Secondary Structure of Human Calcitonin Monitored by ATR-FTIR Spectroscopy", Biochemistry, 33: 12276-12282, 1994.

Benvenga et al. "Homology of Calcitonin With the Amyloid-Related Proteins", Journal of Endocrinological Investigation, 17: 119-122, 1994.

Berger et al. "Calcitonin-Like Immunoreactivity of Amyloid Fibrils in Medullary Thyroid Carcinomas", Virchows Archiv A Pathological Anatomy and Histopathology, 412: 543-551, 1988.

Berson et al. "Proprotein Convertase Cleavage Liberates A Fibrillogenic Fragment of A Resident Glycoprotein to Initiate Melanosome Biogenesis", Journal of Cell Biology, 161(3): 521-533, 2003.

Bird et al. "Single-Chain Antigen-Binding Proteins", Science, 242(4877): 423-426, 1988.

Boerner et al. "Production of Antigen-Specific Human Monoclonal Antibodies From In Vitro-Primed Human Splenocytes", The Journal of Immunology, 147(1): 86-95, 1991.

Bong et al. "Self-Assembling Organic Nanotubes", Angewandte Chemie, International Edition,40:988-1011, 2001.

Chapman et al. "Role of *Escherichia coli* Curli Operons in Directing Amyloid Fiber Formation", Science, 295(5556): 851-855, 2002, Abstract.

Choplin "Computers and the Medicinal Chemist", Comprehensive Medicinal Chemistry, 4(Chap.17.2): 33-58, 1990.

Chou et al. "Conformational Parameters for Amino Acids in Helical, β-Sheet, and Random Coil Regions Calculated From Proteins", Biochemistry, 13(2): 211-222, 1974.

Chou et al. "Empirical Predictions of Protein Conformation", Annual Reviews in Biochemistry, 47: 251-276, 1978.

Claessen et al. "A Novel Class of Secreted Hydrophodic Proteins is Involved in Aerial Hyphae Formation in Streptomyces Coelicolor by Forming Amyloid-Like Fibrils", Genes & Development, 17: 1714-1726, 2003.

Claessens et al. "Review Commentary: π- π Interactions in Self-Assembly", Journal of Physical Organic Chemistry, 10: 254-272, 1997.

Clark et al. "Self-Assembling Cyclic β3-Peptide Nanotubes as Artificial Transmembrane Ion Channels", Journal of the American Chemical Society, JACS, 120: 651-656, 1998.

Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.

Copp "Endocrine Regulation of Calcium Metabolism", Annual Reviews in Physiology, 32: 61-86, 1970.

Elliot et al. "The Chaplins: A Family of Hydrophobic Cell-Surface Proteins Involved in Aerial Mycelium Formation in Streptomyces Coelicolor", Genes & Development, 17: 1727-1740, 2003.

Findeis et al. "Modified-Peptide Inhibitors of Amyloid β-Peptide Polymerization", Biochemistry, 38: 6791-6800, 1999.

Fingl et al. "Inroduction: General Principles", The Pharmacological Basis of Therapeutics, 5th Ed., Sec.1(Chap.1): 1-53, 1975.

Fishwild et al. "High-Avidity Hum IgGκ Monoclonal Antibodies From A Novel Strain of Minilocus Transgenic Mice", Nature Biotechnology, 14: 845-851, 1996.

Gazit "Mechanisms of Amyloid Fibril Self-Assembly and Inhibition Model Short Peptides as A Key Research Tool", The FEBS Journal, 272: 5971-5978, 2005.

Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.

Ghadiri et al. "Artificial Transmembrane Ion Channels From Self-Assembling Peptide Nanotubes", Nature, 369(6478): 301-304, 1994.

Gillard et al. "Controlling Self-Assembly", Chemical European Journal, 3(12): 1933-1940, 1997.

Häggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.

Harlow et al. "Antibodies: A Laboratory Manual", Cold Spring Harbor Laboratory, p. III-IX, 1988.

Holmes et al. "Extensive Neurite Outgrowth and Active Synapse Formation on Self-Assembling Peptide Scaffolds", Proc. Natl. Acad. Sci. USA, 97(12): 6728-6733, 2000.

Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.

Hoyle et al. "Pseudomonas Aeruginosa Biofilm as A Diffusion Barrier to Piperacillin", Antimicrobial Agents and Chemotherapy, 36(9): 2054-2056, 1992.

Huang et al. "A Review on Polymer Nanofibers by Electrospinning and Their Applications in Nanocomposites", Composites Science and Technology, 63: 2223-2253, 2003.

Inbar et al. "Localization of Antibody-Combining Sites Within the Variable Portions of Heavy and Light Chains", Proc. Natl. Acad. Sci. USA, 69(9): 2659-2662, 1972.

Jack et al. "The Organization of Aromatic Side Groups in An Amyloid Fibril Probed by Solid-State 2H and 19F NMR Spectroscopy", Journal of the American Chemical Society, JACS, 128: 8098-8099, 2006.

Jayawarna et al. "Nanostructured Hydrogels for Three-Dimensional Cell Culture Through Self-Assembly of Fluorenylmethoxycarbonyl-Dipeptides", Advanced Materials, 18: 611-614, 2006.

Jin "Electrospinning Bombyx Mori Silk With Poly (Ethylene Oxide)" Biomacromolecules, 3: 1233-1239, 2002.

Jones et al. "Replacing the Complementarity-Determining Regions in A Human Antibody With Those From A Mouse", Nature, 321: 522-525, 1986.

Kamihira et al. "Conformational Transitions and Fibrillation Mechanism of Human Calcitonin as Studied by High-Resolution Solid-State 13C NMR [in Process Citation]", Protein Science, 9: 867-877, 2000.

Kanaori et al. "Study of human Calcitonin Fibrillation by Proton Nuclear Magnetic Resonance Spectroscopy", Biochemistry, 34: 12138-12143, 1995.

Kaplan "Fibrous Proteins-Silk as A Model System", Polymer Degradation and Stability, 59: 25-32, 1998.

Kapurniotu et al. "Structure-Based Design and Study of Non-Amyloidogenic, Double N-Methylated IAPP Amyloid Core Sequences as Inhibitors of Formation and Cytotoxicity", Journal of Molecular Biology, 315: 339-350, 2002.

Kedar et al. "In Vitro Synthesis of 'Amyloid' Fibrils From Insulin, Calcitonin and Parathormone", Israel Journal of Medical Science, 12(10): 1137-1140, 1976.

Kubik "High-Performance Fibers from Spider Silk", Angewandte Chemie, International Edition, 41(15): 2721-2723, 2002.

Kyte et al. "A Simple Method for Displaying the Hydropathic Character of A Protein", Journal of Molecular Biology, 157: 105-132, 1982.

Larrick et al. "PCR Amplification of Antibody Genes", Methods: A Companion to Methods in Enzymology, 2(2): 106-110, 1991.

Lazaris et al. "Spider Silk Fibers Spun From Soluble Recombinant Silk Produced in Mammalian Cells", Science, 295: 472-476, 2002. p. 474-475.

Lee et al. "Virus-Based Febrication of Micro- and Nanofibers Using Electrospinnig" Nano Letters,4(3): 387-390, 2004.

Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.

Lonberg et al. "Antigen-Specific Human Antibodies From Mice Comprising Four Distinct Genetic Modifications", Nature, 368(6474): 856-859, 1994.

Lonberg et al. "Human Antibodies From Transgenic Mice", International Review of Immunology, 13: 65-93, 1995.

Lowe et al. "Structure-Function Relationships for Inhibitors of β-Amyloid Toxicity Containing the Recognition Sequence KLVFF", Biochemistry, 40: 7882-7889, 2001.

Lyon et al. "Self-Assembly and Gelation of Oxidized Gluthathione in, Organic Solvents", Journal of the American Chemical Society, 123: 4408-4413, 2001.

Mah et al. "A Genetic Basis for Pseudomonas Aeruginosa Biofilm Antibiotic Resistance", Nature, 426: 306-310, 2003.

Mahler et al. "Rigid, Self-Assembled Hydrogel Composed of A Modified Aromatic Dipeptide", Advanced Materials, 18(11): 1365-1370, 2006.

Marks et al. "By-Passing Immunization—Human Antibodies from V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Matsui et al. "Crystalline Glyclylglycine Bolaamphiphile Tubules and Their pH-Sensitive Structural Transformation" The Journal of Physical Chemistry B, 104(15): 3384-3386, 2000.

Maury et al. "Creation of Amyloid Fibrils From Mutant ASN187 Gelsolin Peptides", Biochemical and Biophysical Research Communications, 183(1): 227-231, 1992.

McGaughey et al. "π-Stacking Interactions", The Journal of Biological Chemistry, 273(25): 15458-15463, 1998.

Meluleni et al. "Mucoid Pseudomonas Aeruginosa Growing in A Biofilm in Vitro are Killed by Opsonic Antibodies to the mucoid Exopolysaccharide Capsule but Not by Antibodies Produced During Chronic Lung Infection in Cystic Fibrosis Patients[1],[2]", Journal of Immunology, 155:2029-2038, 1995.

Morrison "Success in Specification", Nature, 368(6474): 812-813, 1994.

Mosmann "Rapid Colorimetric Assay for Cellular Growth and Survival: Application to Proliferation and Cytotoxicity Assays", Journal of Immunological Methods, 65: 55-63, 1983.

Murphy et al. "Biofilm Formation by Nontypeable Haemophilus Influenzae: Strain variability, Outer Membrane Antigen Expression and Role of pili", BMC Microbiology, 2(7): 2002, 1-8.

Mutter "Studies on the Coupling Rates in Liquid-Phase Peptide Synthesis Using Competition Experiments", International Journal of Peptide Protein Research, 13: 274-277, 1979.

Neuberger "Generating High-Avidity Human Mabs in Mice", Nature Biotechnology, 14: 826, 1996.

Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.

Pack et al. "Improved Bivalent Miniantibodies, With Identical Avidity as Whole Antibodies, Produced by High Cell Density Fermentation of *Escherichia coli*", Bio/Technology, 11: 1271-1277, 1993.

Petkova et al. "A Structural Model for Alzheimer's β-Amyloid Fibrils Based on Experimental Constraints From Solid State NMR", Proc. Natl. Acad. Sci. USA, 99(26): 16742-16747, 2002.

Pettmann et al. "Morphological and Biochemical Maturation of Neurones Cultured in the Absence of Glial Cells", Nature, 281: 378-380, 1979.

Porter "The Hydrolysis of Rabbit γ-Globulin and Antibodies With Crystalline Papain", Biochemical Journal, 73: 119-126, 1959.

Presta "Antibody Engineering", Current Opinion in Structural Biology, 2: 593-596, 1992.

Puchtler et al. "A Review of Early Concepts of Amyloid in Context With Contemporary Chemical Literature From 1839 to 1859", The Journal of Histochemistry and Cytochemistry, 14(2): 123-134, 1966.
Reches et al. "Designed Aromatic Homo-Dipeptides: Formation of Ordered Nanostructures and Potential Nanotechnological Applications", Physical Biology, 3: S10-S19, 2006.
Reches et al. "Self-Assembly of Peptide Nanotubes and Amylois-Like Structures by Charged-Termini-Capped Diphenylalanine Peptide Analogues", Israel Journal of Chemistry, 45(3): 363-371, 2005.
Reches et al. "Supporting Online Material", Science, 300(5619): 1-9, 2003. Retrieved From the Internet: URL:http://www.sciencemag.org/cgi/data/300/5619/625/DC1.
Riechmann et al. "Reshaping Human Antibodies for Therapy", Nature, 332: 323-329, 1988.
Sacchettini et al. "Therapeutic Strategies for Human Amyloid Diseases", Nature Reviews: Drug Discovery, 1: 267-275, 2002.
Shetty et al. "Aromatic π-Stacking in Solution as Revealed Through the Aggregation of Phenylacetylene Macrocycles", Journal of the American Chemical Society, 118: 1019-1027, 1996.
Solomon et al. "Disaggregation of Alzheimer β-Amyloid by Site-Directed MAb", Proc. Natl. Acad. Sci. USA, 94: 4109-4112, 1997.
Stewart "Theoretical Aspects of Antibiotic Diffusion Into Microbial Biofilms", Antimicrobial Agents and Chemotherapy, 40(11): 2517-2522, 1996.
Sun et al. "Aromatic Van der Waals Clusters: Structure and Nonrigidity", Journal of Physical Chemistry, 100: 13348-13366, 1996.
Tjernberg et al. "Arrest of β-Amyloid Fibril Formation by A Pentapeptide Ligand", The Journal of Biological Chemistry, 271(15): 8545-8548, 1996.
Tjernberg et al. "Controlling Amyloid β-Peptide Fibril Formation With Protease-Stable Ligands", The Journal of Biological Chemistry, 272(19): 12601-12605, 1997.
Toledano et al. "Enzyme-Triggered Self-Assembly of Peptide Hydrogels Via Reversed Hydrolysis", Journal of the American Chemical Society, JACS, 128(4): 1070-1071, 2006.
Tonkinson et al. "Antisense Oligodeoxynucleotides as Clinical Therapeutic Agents", Cancer Investigation, 14(1): 54-65, 1996.
True et al. "Epigenetic Regulation of Trenslation Reveals Hidden Genetic Variation to Produce Complex Traits", Nature, 431: 184-187, 2004.
Tsang et al. "A Simple Chemical Method of Opening and Filling Carbon Nanotubes", Nature, 372: 159-162, 1994.
Tuite et al. "Propagation of Yeast Prions", Nature Reviews 4: 878-889, 2003.
Vauthey et al. "Molecular Self-assembly of Surfactant-Like Peptides to form Nanotubes and Nanovesicles", PNAS,99(8):5355-5360, 2002.
Verhoeyen et al. "Reshaping Human Antibodies: Grafting An Antilysozyme Activity", Science, 239: 1534-1536, 1988.
Vidal et al. "A Stop-Codon Mutation int he BRI Gene Associated With Familial British Dementia", Nature, 399: 776-781, 1999.
Whitlow et al. "Single-Chain Fv Proteins and Their Fusion Proteins", Methods: A Companion to Methods in Enzymology, 2(2): 97-105, 1991.
Wolfenden et al. "Affinities of Amino Acid Side Chains for Solvent Water", Biochemistry, 20: 849-855, 1981.
Yokoi et al. "Dynamic Reassembly of Peptide RADA16 Nanofiber Scaffold", Proc. Natl. Acad. Sci. USA, 102(24): 8414-8419, 2005.
Zaidi et al. "Forty Years of Calcitonin—Where Are We Now? A Tribute to the Work of Iain Macintyre, FRS", Bone, 30(5): 655-663, 2002.
Zhang et al. "Supramolecular Hydrogels Respond to Ligand-Receptor Interaction", Journal of the American Chemical Society, 125(45): 13680-13681, 2003.
Cherny et al. "The Formation of *Escherichia coli* Curli Amyloid Fibrils is Mediated by Prion-Like Peptide Repeats", Journal of Molecular Biology, 352(2): 245-252, 2005.
Cherny et al. "The YefM Antitoxin Defines A Family of Natively Unfolded Proteins", The Journal of Biological Chemistry, 279(9): 8252-8261, 2004.

Engelberg-Kulka et al. "Bacterial Programmed Cell Death Systems as Targets for Antibiotics", Trends in Microbiology, vol. 12 (2): p. 66-71, 2004.
Forloni et al. "Anti-Amyloidogenic Activity of Tetracyclines: Studies in Vitro", FEBS Letters, 487(3): 404-407, 2001. Figs. 1,3.
Görbitz "Nanotube Formation by Hydrophobic Dipeptides", Chemistry, 7(23): 5153-5159, 2001, Abstract.
Grady et al. "Axe—Txe, A Broad-Spectrum Proteic Toxin—Antitoxin System Specified by a Multidrug-Resistant, Clinical Isolate of Enterococcus Faecium", Molecular Microbiology, vol. 47(5: p. 1419-1432, 2003.
Grateau "[Coli's Curli or How Amyloid Can be Physiological.]", Médecine Sciences, 18(6-7): p. 664, 2002.
Haldar et al. "First Crystallographic Signature of the Highly Ordered Supramolecular Helical Assemblage From A Tripeptide Containing A Non-Coded Amino Acid", Tetrahedron Letters, 43(14): 2653-2656, 2002. Abstract.
Harrison et al. "Amyloid Peptides and Proteins in Review", Reviews in Physiology, Biochemistry and Pharmacology, 159: 1-77, 2007.
Hartgerink et al. "Peptide Nanotubes and Beyond", Chemistry European Journal 4(8): 1367-1372, 1998. Abstract.
Lansbury "Following Nature's Anti-Amyloid Strategy", Nature Biotechnology 19(2): 112-113, 2001. p. 112, Left-Hand col., Paragraph 1—Middle col., Paragraph 1.
Maji et al. "Fibril-Forming Model Synthetic Peptides Containing 3-Aminophenylacetic Acid", Tetrahedron, 58(43): 8695-8702, 2002, Abstract.
Mosselman et al. "The Complete Islet Amyloid Polypeptide Precursor Is Encoded by Two Exons", FEBS Letters, 247: 154-158, 1989, Database Accession No. S04016.
Nicolaus "Symbiotic Approach to Drug Design", Decision Making in Drug Research, p. 173-186, 1983.
Reches et al. "Amyloid Fibril Formation by Pentapeptide and Tetrapeptide Fragments of Human Calcitonin", The Journal of Biological Chemistry, 277(38): 35475-35480, 2002.
Reches et al. "Casting Metal Nanowires Within Discrete Self-Assembled Peptide Nanotubes", Science, 300(5619): 625-627, 2003, Abstract.
Sigel-Causey et al. "Phylogeny of the Pelecaniformes: Molecular Systematics of A Privative Group", Avian Molecular Evolution and Systematics, academic Press, p. 159-171, NBCI GenBank, Accession No. AAB58518, 1997.
Notice of Allowance Dated Sep. 17, 2008 From the US Patent Office Re.: U.S. Appl. No. 11/148,266.
Official Action Dated Sep. 29, 2008 From the US Patent Office Re.: U.S. Appl. No. 11/660,522.
Inouye et al "Synthesis And Biological Properties of The 10-Substituted Analogues of ACTH-(1-18)-NH2", Shionogi Research Laboratory, Fukushima-Ku, Osaka, p. 177-182, 1978.
Jelokhani-Niaraki et al "Changes in Conformation and Antimicrobial Properties Caused by Replacement of D-amino Acids With α-Aminoisobutyric Acid in the Gramicidin Backbbone:Synthesis and Circular Dichroic Studies", J. Chem. Soc. Perkin Trans., 2: 1187-1193, 1992.
Examination Report Dated Jan. 8, 2008 From the Government of India, Patent Office Re.: Application No. 1671/CHENP/2004.
Examination Report Dated May 10, 2007 From the Government of India, Patent Office Re.: Application No. 1499/CHENP/2005.
Examination Report Dated Jun. 19, 2007 of the Government of India, Patent Office Re.: Application No. 1671/CHENP/2004.
Examination Report Dated Mar. 20, 2008 From the Government of India, Patent Office Re.: Application No. 1400/CHENP/2006.
International Search Report Dated May 10, 2004 From International Searching Authority Re.: Application No. PCT/IL2004/000012.
International Search Report Dated Aug. 16, 2005 From the International Searching Authority Re.: Application No. PCT/IL2004/000898.
International Search Report Dated Jul. 19, 2004 From the International Searching Authority Re.: Application No. PCT/IL03/01045.
Notice of Allowance Dated Sep. 16, 2008 From the US Patent Office Re.: U.S. Appl. No. 11/148,262.
Notice of Allowance Dated Sep. 17, 2008 From the US Patent Office Re.: U.S. Appl. No. 11/148,266.

Office Action Dated Sep. 15, 2008 From the Israeli Patent Office Re.: Application No. 169121 and Its Translation Into English.
Office Action Dated Sep. 15, 2008 From the Israeli Patent Office Re.: Appliction No. 169120 and Its Translation Into English.
Official Action Dated Sep. 2, 2008 From the US Patent Office Re.: U.S. Appl. No. 11/471,657.
Official Action Dated Dec. 3, 2008 From the US Patent and Trademark Office Re.: U.S. Appl. No. 10/574,405.
Official Action Dated Dec. 12, 2008 From the US Patent and Trademark Office Re.: U.S. Appl. No. 11/656,542.
Official Action Dated Dec. 16, 2008 From the US Patent and Trademark Office Re.: U.S. Appl. No. 10/562,852.
Official Action Dated Sep. 29, 2008 From the US Patent Office Re.: U.S. Appl. No. 11/660,522.
Translation of the Examination Report Dated Oct. 10, 2006 From the Goverment of India, Patent Office Re.: Application No. 1510/CHENP/2005.
Translation of the Notice of Reason of Rejection Dated Jul. 11, 2008 From the Japanese Patent Office Re.: Application No. 2003-563456.
Written Opinion Not Dated From the International Searching Authority Re.: Application No. PCT/IL2004/000898.
Cherny et al. "The Formation of *Escherichia coli* Curti Amyloid Fibrils is Mediated by Prion-Like Peptide Repeats", Journal of Molecular Biology, 352(2): 245-252, 2005.
Chopin et al. "Analysis of Six Prophages in Lactococcus Lactis IL1403: Different Genetic Structure of Temperate and Virulent Phage Populations", Nucleic Acids Research, 29(3): 644-651, 2001.
Ghadiri et al. "Self-Assembling Organic Nanotubes Based on A Cyclic Peptide Architecture", Nature, 366: 324-327, Dec. 25, 1993.
Görbitz "Nanotube Formation by Hydrophobic Dipeptides", Chemical European Journal, Chemistry, XP001180634, 7(23): 5153-5159, Dec. 3, 2001.
Hayden et al. "'A' Is for Amylin and Amyloid in Type 2 Diabetes Mellitus", JOP Journal of the Pancreas (Online), 2(4): 124-139, 2001.

Horne et al. "A Heterocyclic Peptide Nanotube", Journal of the American Chemical Society, JACS, 125(31): 9372-9376, Aug. 6, 2003. Abstract.
Inouye et al "Synthesis and Biological Properties of the 10-Substituted Analogues of ACTH-(1-18)-NII2", Shionogi Research Laboratory, Fukushima-Ku, Osaka, p. 177-182, 1978.
Jelokhani-Niaraki et al "Changes in Conformation and Antimicrobial Properties Caused by Replacement of D-Amino Acids With α-Aminoisobutyric Acid in the Gramicidin Backbbone: Synthesis and Circular Dichroic Studies", Journal of the Chemical Society Perkin Transactions, 2: 1 187-1193, 1992.
Maji et al. "Fibril-Forming Model Synthetic Peptides Containing 3-Aminophenylacetic Acid", Tetrahedron, 58(43): 8695-8702, 2002, Abstract.
Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.
Reza et al "Self-assembling Organic Nanotubes Based on a Cyclic Peptide Architecture", Nature 366:324-327 (1993).
Sano "Prevention of Alzheimer's Disease: Where We Stand", Current Neurology and Neuroscience Reports, 2(5): 392-399, Oct. 2002. Abstract.
Sigel-Causey et al. "Phylogeny of the Pelecaniformes: Molecular Systematics of A Privative Group", Avian Molecular Evolution and Systematics, academic Press, p. 159-171, NBCI GenBank, Accession No. AAB58518, 1997.
Stephenson et al. "The 'Promiscuous Drug Concept' With Applications to Alzheimer's Disease", FEBS Letters, 579: 1338-1342, 2005.
Tsai et al. "Synthesis of AIB-Containing Peptidomimetics as Potential Inhibitors of Alzheimer's γ-Secretase", 218th ACS National Meeting, New Orleans, USA, Meeting Abstract, MEDI-018, 1999. Abstract.

* cited by examiner

Rodent KCNTATCATQRLANFLVRSSNNLGPVLPPTNVGSNTY SEQ ID NO: 152

Human KCNTATCATQRLANFLVHSSNNNFGAILSSTNVGSNTY SEQ ID NO: 153

| | | |
|---|---|---|
| wt | NH2-NFGAILSS-COOH | SEQ ID NO: 1 |
| N1A | NH2-AFGAILSS-COOH | SEQ ID NO: 2 |
| F2A | NH2-NAGAILSS-COOH | SEQ ID NO: 3 |
| G3A | NH2-NFAAILSS-COOH | SEQ ID NO: 4 |
| I5A | NH2-NFGAALSS-COOH | SEQ ID NO: 5 |
| L6A | NH2-NFGAIASS-COOH | SEQ ID NO: 6 |

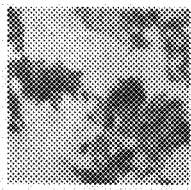 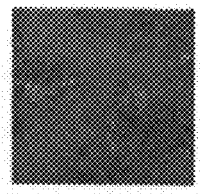 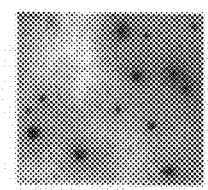 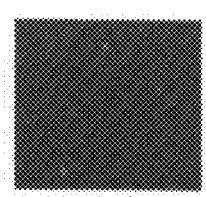
Fig. 6a      Fig. 6b      Fig. 6c      Fig. 6d
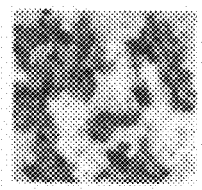 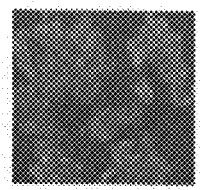 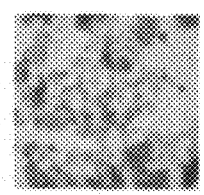 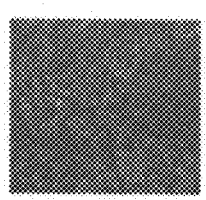
Fig. 6e      Fig. 6f      Fig. 6g      Fig. 6h
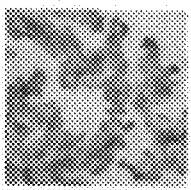 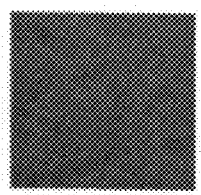 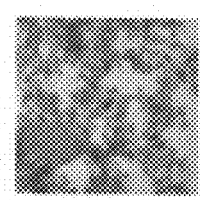 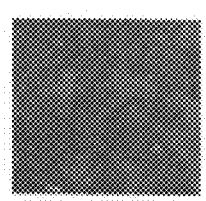
Fig. 6i      Fig. 6j      Fig. 6k      Fig. 6l
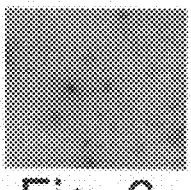 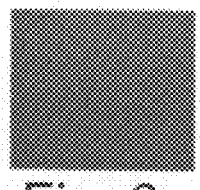
Fig. 6m      Fig. 6n Synthetic gene SEQ ID NO: 165
Human cDNA SEQ ID NO: 166

SEQ ID NO: 164

① M  K  C  N  T  A  T  C  A  T  Q  R  L  A
② ATGAAATGCAACACCGGCGACCTGCGCGACCCAGCGCCTGGCG
③ ATGAAATGCAACACTGCCACATGTGCAACCAGCGCCTGGCA

① M  F  L  V  H  S  S  N  N  F  G  A  I  L
② AACTTTCTGGTGCATAGCAGCAACAACTTTGGCGCGATTCTG
③ AATTTTTAGTTCATTCCAGCAACAACTTTGGTGCCATTCTC

① S  S  T  N  V  G  S  N  T  Y
② AGCAGCACCAACGTGGGCAGCAACACCTAT
③ TCATCTACCAACGTGGGGATCCAATACATAT

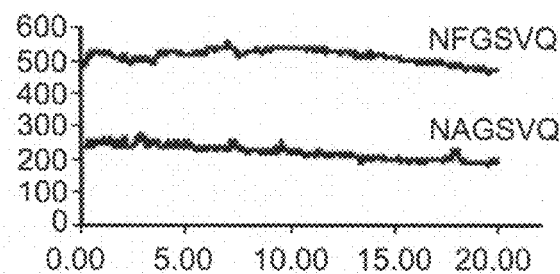
Fig. 19a
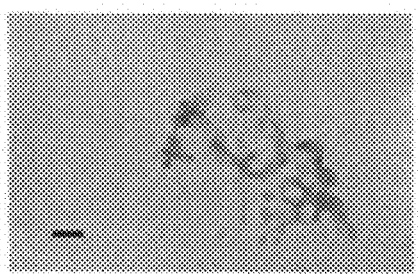
Fig. 19b
Fig. 19c
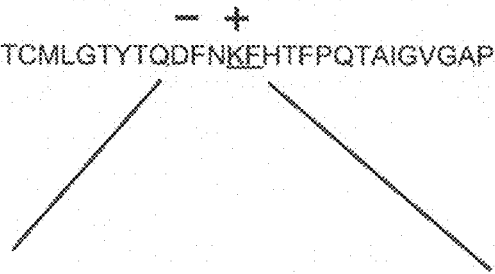
Fig. 20a  NH$_2$-CGNLSTCMLGTYTQDFN<u>KE</u>HTFPQTAIGVGAP-COOH
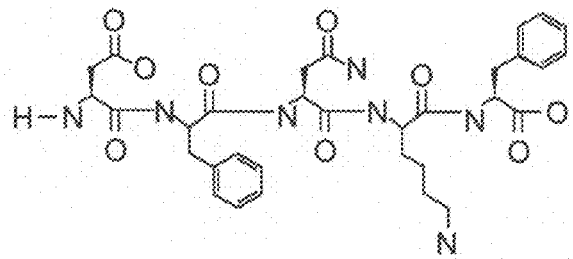
Fig. 20b

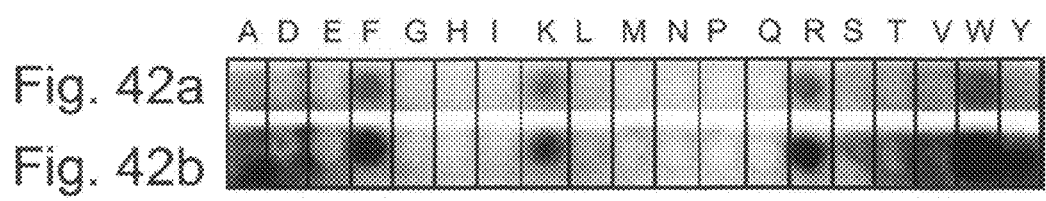
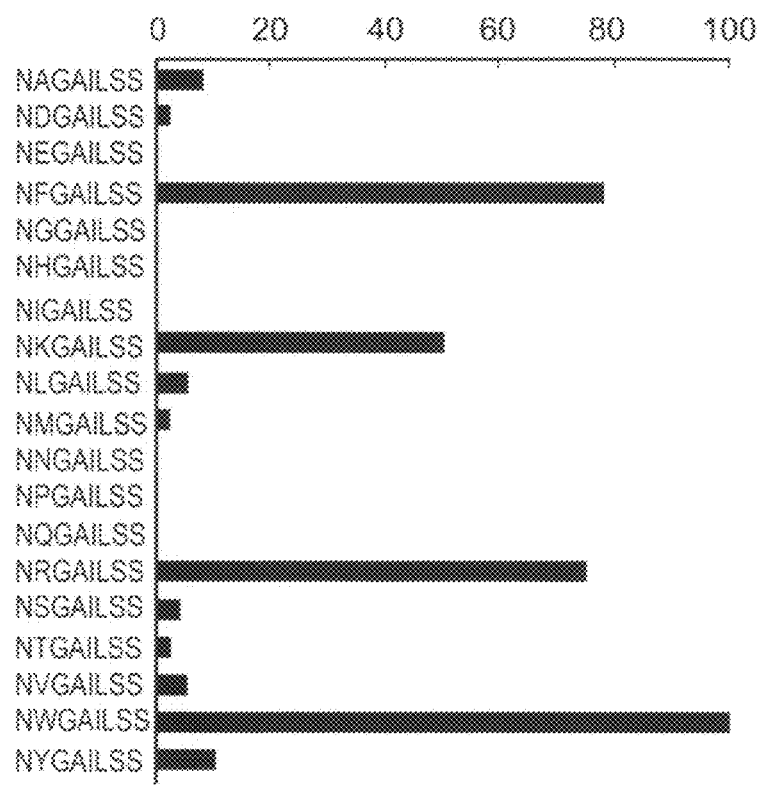
Fig. 42c

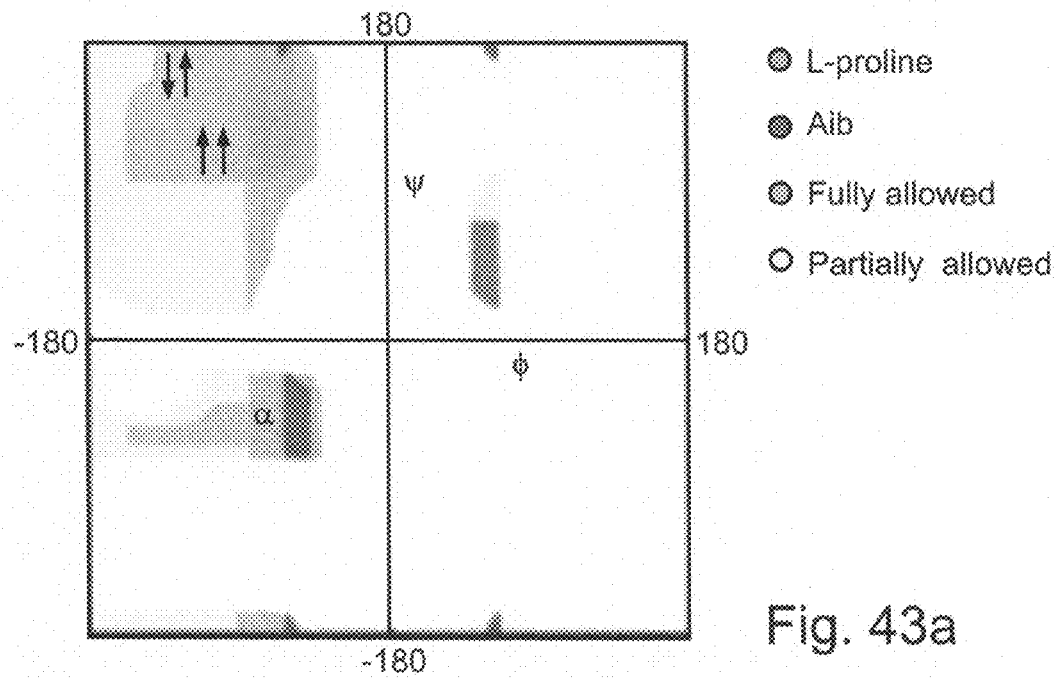
Fig. 43a
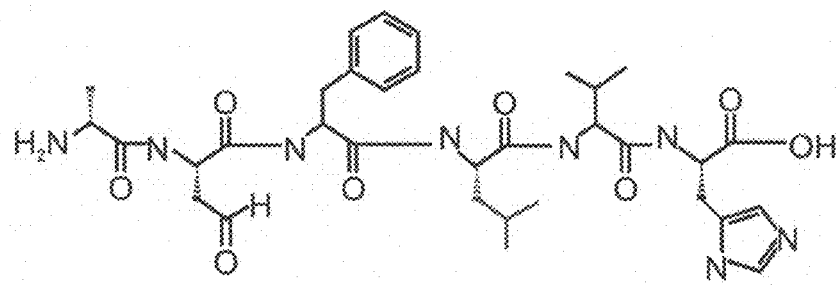
Fig. 43b
Fig. 43c

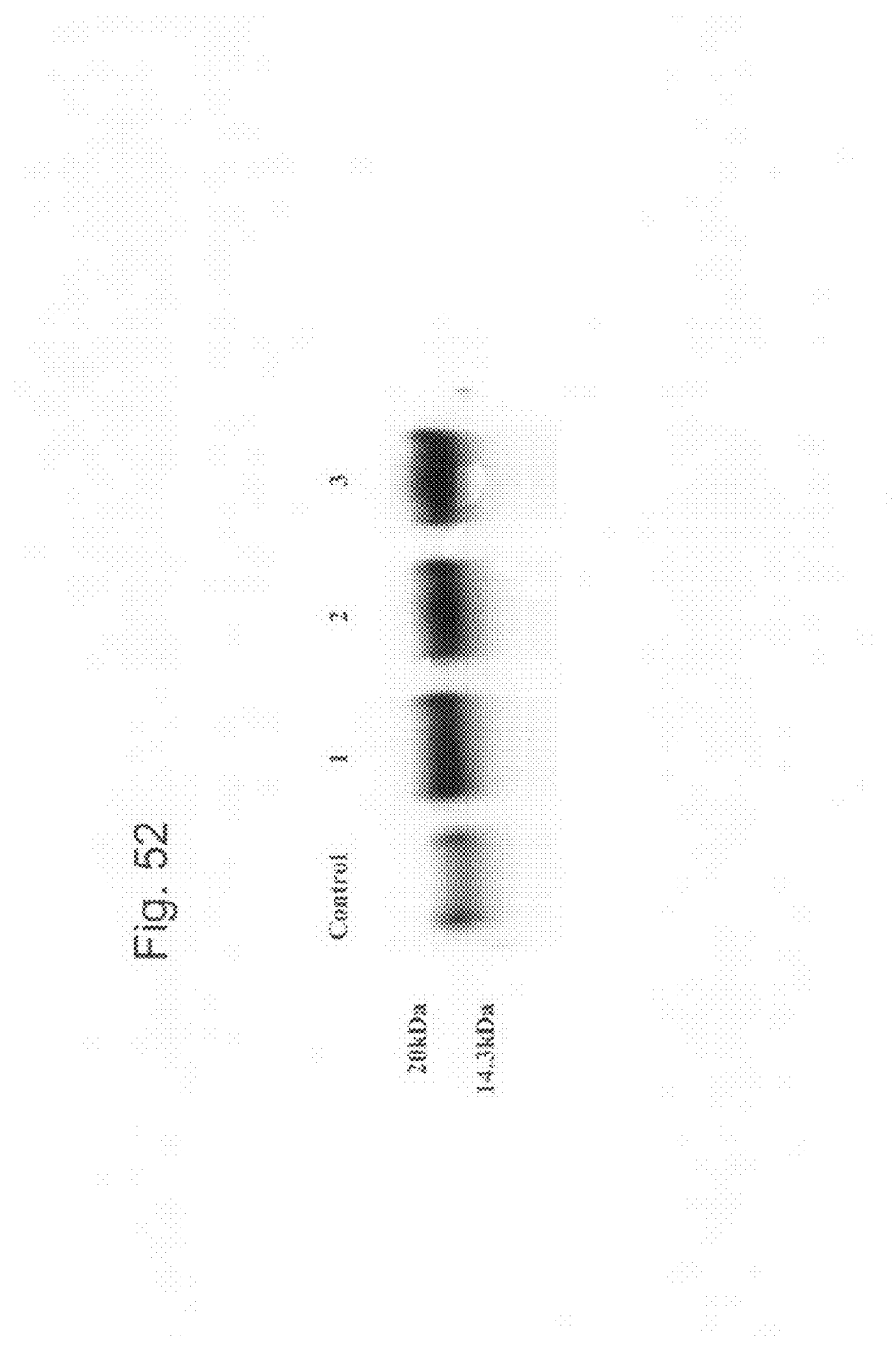

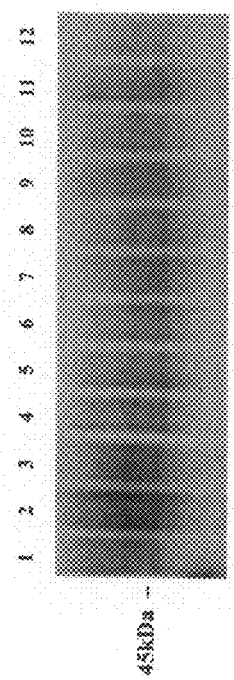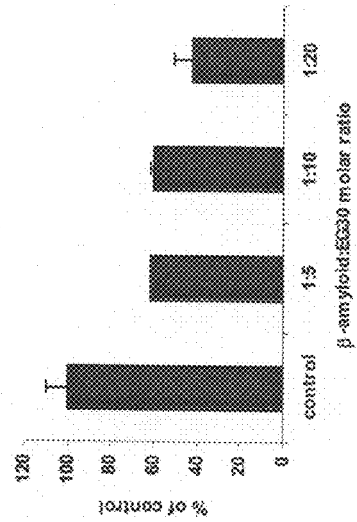
Fig. 53a
Fig. 53b

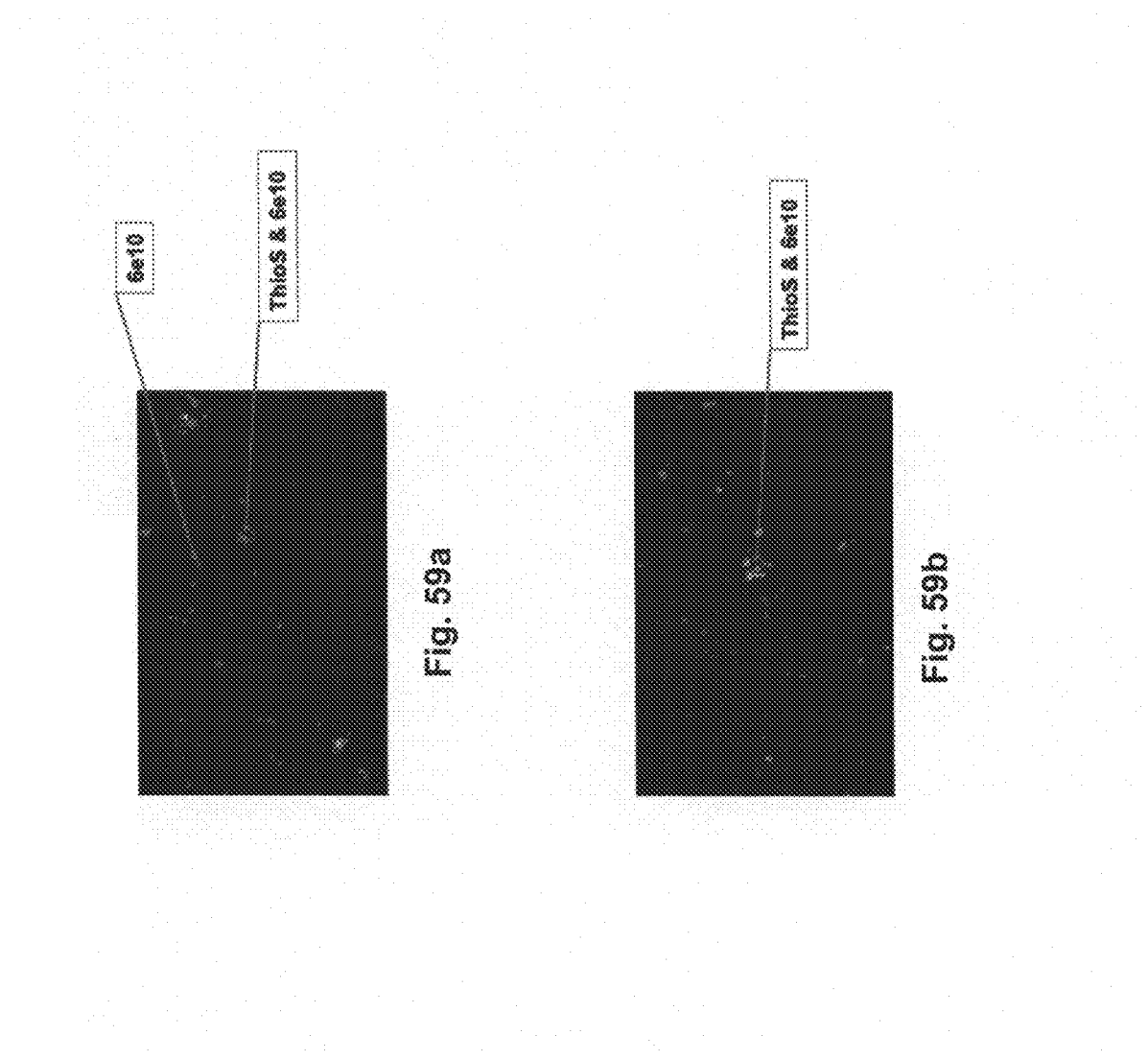

PEPTIDES DIRECTED FOR DIAGNOSIS AND TREATMENT OF AMYLOID-ASSOCIATED DISEASE

RELATED APPLICATIONS

This application is continuation-in-part (CIP) of U.S. patent application Ser. No. 10/562,852, filed Dec. 30, 2005, which is a National Phase of PCT Patent Application No. PCT/IL2004/000577 having International Filing Date of Jun. 29, 2004, which claims the benefit of U.S. Provisional Patent Application No. 60/483,180, filed Jun. 30, 2003, and U.S. Provisional Patent Application No. 60/514,974, filed Oct. 29, 2003.

U.S. patent application Ser. No. 10/562,852 is also a continuation-in-part (CIP) of U.S. patent application Ser. No. 10/901,243, filed Jul. 29, 2004, which is continuation-in-part (CIP) of PCT Patent Application No. PCT/IL03/00079, filed Jan. 30, 2003, which is a continuation of U.S. patent application Ser. No. 10/235,852, filed Sep. 6, 2002, and also claims the benefit of U.S. Provisional Patent Application No. 60/352,578, filed Jan. 31, 2002, U.S. Provisional Patent Application No. 60/392,266, filed Jul. 1, 2002 and U.S. Provisional Patent Application No. 60/436,453, filed Dec. 27, 2002.

The contents of all the above Patent Applications are incorporated herein by reference.

FIELD AND BACKGROUND OF THE INVENTION

The present invention relates to peptides and antibodies directed there against which can be used to diagnose, prevent, and treat amyloid-associated diseases, such as Type II diabetes mellitus and Alzheimer's disease.

Amyloid material deposition (also referred to as amyloid plaque formation) is a central feature of a variety of unrelated pathological conditions including Alzheimer's disease, prion-related encephalopathies, type II diabetes mellitus, familial amyloidosis and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel or parallel β-pleated sheets lying with their long axes perpendicular to the long axis of the fibril [Both et al. (1997) Nature 385:787-93; Glenner (1980) N. Eng. J. Med. 302:1283-92; Balbach et al. (2002) Biophys J. 83:1205-16].

Approximately twenty amyloid fibril proteins have been identified in-vivo and correlated with specific diseases. These proteins share little or no amino acid sequence homology; however the core structure of the amyloid fibrils is essentially the same. This common core structure of amyloid fibrils and the presence of common substances in amyloid deposits suggest that data characterizing a particular form of amyloid material may also be relevant to other forms of amyloid material and thus can be implemented in template design for the development of drugs against amyloid-associated diseases such as type II diabetes mellitus, Alzheimer's dementia or diseases and prion-related encephalopathies.

Furthermore, amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of amyloid polypeptides or inhibiting amyloidosis may be useful for treating amyloid associated diseases.

Inhibition of the production of amyloid polypeptides—Direct inhibition of the production of amyloid polypeptides may be accomplished, for example, through the use of antisense oligonucleotides such as against human islet amyloid polypeptide messenger RNA (mRNA). In vitro, the addition of antisense oligonucleotides or the expression of antisense complementary DNA against islet amyloid polypeptide mRNA increased the insulin mRNA and protein content of cells, demonstrating the potential effectiveness of this approach [Kulkarni et al. (1996) J. Endocrinol. 151:341-8; Novials et al. (1998) Pancreas 17:182-6]. However, no experimental results demonstrating the in vivo effectiveness of such antisense molecules have been demonstrated.

Inhibition of the formation of amyloid fibrils—Amyloid, including islet amyloid, contains potential stabilizing or protective substances, such as serum amyloid P component, apolipoprotein E, and perlecan. Blocking their binding to developing amyloid fibrils could inhibit amyloidogenesis [Kahn et al. (1999) Diabetes 48:241-53], as could treatment with antibodies specific for certain parts of an amyloidogenic protein [Solomon et al. (1997) Proc. Natl. Acad. Sci. USA 94:4109-12].

The following summarizes current attempts to engineer drugs having the capability of destabilizing amyloid structures.

Destabilizing compounds—Heparin sulfate has been identified as a component of all amyloids and has also been implicated in the earliest stages of inflammation-associated amyloid induction. Kisilevsky and co-workers (Nature Med. 1:143-148, 1995) described the use of low molecular weight anionic sulfonate or sulfate compounds that interfere with the interaction of heparin sulfate with the inflammation-associated amyloid precursor and the β peptide of Alzheimer's disease (AD). Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin accelerated Aβ fibril formation and were able to disassemble preformed fibrils in vitro, as monitored by electron micrography. Moreover, these compounds substantially arrested murine splenic inflammation-associated amyloid progression in vivo in acute and chronic models. However, the most potent compound [i.e., poly-(vinylsulfonate)] showed acute toxicity. Similar toxicity has been observed with another compound, IDOX (Anthracycline 4'-iodo-4'-deoxy-doxorubicin), which has been observed to induce amyloid resorption in patients with immunoglobin light chain amyloidosis (AL) [Merlini et al. (1995) Proc. Natl. Acad. Sci. USA 92:2959-63].

Destabilizing antibodies—Anti-β-amyloid monoclonal antibodies have been shown to be effective in disaggregating β-amyloid plaques and preventing β-amyloid plaque formation in vitro (U.S. Pat. No. 5,688,561). However, no experimental results demonstrating the in vivo effectiveness of such antibodies have been demonstrated.

Destabilizing peptides—The finding that the addition of synthetic peptides that disrupt the β-pleated sheets ("β-sheet breakers") dissociated fibrils and prevented amyloidosis [Soto et al. (1998) Nat. Med. 4:822-6] is particularly promising from a clinical point of view. In brief, a penta-residue peptide inhibited amyloid beta-protein fibrillogenesis, disassembled preformed fibrils in vitro and prevents neuronal death induced by fibrils in cell culture. In addition, the beta-sheet breaker peptide significantly reduced amyloid beta-protein deposition in vivo and completely blocked the formation of amyloid fibrils in a rat brain model of amyloidosis.

Small molecules—The potential use of small molecules which bind the amyloid polypeptide, stabilizing the native fold of the protein has been attempted in the case of the transthyretin (TTR) protein [Peterson (1998) Proc. Natl. Acad. Sci. USA 95:12965-12960; Oza (1999) Bioorg. Med. Chem. Lett. 9:1-6]. Thus far, it has been demonstrated that molecules such as thyroxine and flufenamic acid are capable of preventing the conformation change, leading to amyloid formation. However, the use of the compounds in animal models has not been proved yet and might be compromised due to the presence in blood or proteins, other than TTR, capable of binding these ligands.

Antioxidants—Another proposed therapy has been the intake of antioxidants in order to avoid oxidative stress and maintain amyloid proteins in their reduced state (i.e., monomers and dimers). The use of sulfite was shown to lead to more stable monomers of the TTR both in vitro and in vivo [Altland (1999) Neurogenetics 2:183-188]. However, a complete characterization of the antioxidant effect is still not available and the interpretation of results concerning possible therapeutic strategies remains difficult.

While reducing the present invention to practice, the present inventors have demonstrated that contrary to the teachings of U.S. Pat. No. 6,359,112 to Kapurniotu, peptide aggregation into amyloid fibrils is governed by aromatic interactions. Such findings enable to efficiently and accurately design peptides, which can be used to diagnose and treat amyloid-associated diseases.

SUMMARY OF THE INVENTION

According to one aspect of the present invention there is provided a peptide comprising amino acid sequence X-Y or Y-X, wherein X is an aromatic amino acid and Y is any amino acid other than glycine, the peptide being at least 2 and no more than 15 amino acids in length.

According to another aspect of the present invention there is provided a peptide comprising an amino acid sequence selected from the group consisting of SEQ ID NOs. 4, 12-19, 27-45, 112-123, 125 and 127, the peptide being at least 2 and no more than 15 amino acids in length.

According to yet another aspect of the present invention there is provided a peptide comprising an amino acid sequence selected from the group consisting of SEQ ID NOs. 4, 12-19, 27-45, 112-123, 125 and 127, the peptide being at least 2 and no more than 15 amino acids in length.

According to still another aspect of the present invention there is provided a peptide selected from the group consisting of SEQ ID NOs. 4, 12-19, 27-45, 112-123, 125 and 127.

According to an additional aspect of the present invention there is provided a method of treating or preventing an amyloid-associated disease in an individual, the method comprising providing to the individual a therapeutically effective amount of a peptide including the amino acid sequence X-Y or Y-X, wherein X is an aromatic amino acid and Y is any amino acid other than glycine, the peptide being at least 2 and no more than 15 amino acids in length.

According to further features in preferred embodiments of the invention described below, the peptide is an active ingredient of a pharmaceutical composition which also includes a physiologically acceptable carrier.

According to still further features in the described preferred embodiments the peptide is expressed from a nucleic acid construct.

According to yet an additional aspect of the present invention there is provided a pharmaceutical composition for treating or preventing an amyloid-associated disease comprising as an active ingredient a peptide including the amino acid sequence X-Y or Y-X, wherein X is an aromatic amino acid and Y is any amino acid other than glycine, the peptide being at least 2 and no more than 15 amino acids in length and a pharmaceutically acceptable carrier or diluent.

According to still further features in the described preferred embodiments at least one amino acid of the at least 2 and no more than 15 amino acids of the peptide is a D stereoisomer.

According to still further features in the described preferred embodiments at least one amino acid of the at least 2 and no more than 15 amino acids of the peptide is an L stereoisomer.

According to still further features in the described preferred embodiments the peptide is two amino acids in length and Y is a β-sheet breaker amino acid.

According to still further features in the described preferred embodiments the peptide is as set forth in SEQ ID NO: 145.

According to still further features in the described preferred embodiments the peptide is 3 amino acids in length, whereas Y is an aromatic amino acid and an amino acid residue attached to the amino acid sequence X-Y or Y-X is a β-sheet breaker amino acid.

According to still further features in the described preferred embodiments the β-sheet breaker amino acid is at a C-terminus of the peptide.

According to still further features in the described preferred embodiments the peptide is at least 3 amino acids in length and includes a thiolated amino acid at an N-terminus thereof.

According to still an additional aspect of the present invention there is provided a nucleic acid construct comprising a polynucleotide segment encoding a peptide including the amino acid sequence X-Y or Y-X, wherein X is an aromatic amino acid and Y is any amino acid other than glycine, the peptide being at least 2 and no more than 15 amino acids in length.

According to still further features in the described preferred embodiments the nucleic acid construct further comprises a promoter.

According to a further aspect of the present invention there is provided an antibody or an antibody fragment comprising an antigen recognition region capable of binding a peptide including the amino acid sequence X-Y or Y-X, wherein X is an aromatic amino acid and Y is any amino acid other than glycine, the peptide being at least 2 and no more than 15 amino acids in length.

According to still further features in the described preferred embodiments Y is a polar uncharged amino acid selected from the group consisting of serine, threonine, asparagine, glutamine and natural derivatives thereof.

According to still further features in the described preferred embodiments Y is a β-sheet breaker amino acid.

According to still further features in the described preferred embodiments the β-sheet breaker amino acid is a naturally occurring amino acid.

According to still further features in the described preferred embodiments the naturally occurring amino acid is selected from the group consisting of proline, aspartic acid, glutamic acid, glycine, lysine and serine.

According to still further features in the described preferred embodiments the β-sheet breaker amino acid is a synthetic amino acid.

According to still further features in the described preferred embodiments the synthetic amino acid is a Cα-methylated amino acid.

According to still further features in the described preferred embodiments the Cα-methylated amino acid is α-aminoisobutyric acid.

According to still further features in the described preferred embodiments the peptide is a linear or cyclic peptide.

According to still further features in the described preferred embodiments the peptide is selected from the group consisting of SEQ ID NOs. 4, 12-19, 27-45, 112-123, 125 and 127.

According to still further features in the described preferred embodiments the peptide is at least 4 amino acids in length and includes at least two serine residues at a C-terminus thereof.

According to still further features in the described preferred embodiments the peptide is at least 3 amino acids in length and whereas at least one of the amino acids of the peptide other than X-Y is a polar uncharged amino acid selected from the group consisting of serine, threonine, asparagine, glutamine and natural derivatives thereof.

According to still further features in the described preferred embodiments the peptide is at least 3 amino acids in length and whereas at least one of the amino acids of the peptide other than X-Y is a is a β-sheet breaker amino acid.

According to still further features in the described preferred embodiments the β-sheet breaker amino acid is a naturally occurring amino acid.

According to still further features in the described preferred embodiments the naturally occurring amino acid is selected from the group consisting of proline, aspartic acid, glutamic acid, glycine, lysine and serine.

According to still further features in the described preferred embodiments the β-sheet breaker amino acid is a synthetic amino acid.

According to still further features in the described preferred embodiments the synthetic amino acid is a Cα-methylated amino acid.

According to still further features in the described preferred embodiments the Cα-methylated amino acid is α-aminoisobutyric acid.

According to still further features in the described preferred embodiments the β-sheet breaker amino acid is located downstream to the X-Y in the peptide.

According to still further features in the described preferred embodiments the β-sheet breaker amino acid is located upstream to the X-Y in the peptide.

According to still further features in the described preferred embodiments the peptide is at least 3 amino acids in length and whereas at least one of the amino acids of the peptide is a positively charged amino acid and at least one of the amino acid residues of the peptide is a negatively charged amino acid.

According to still further features in the described preferred embodiments the positively charged amino acid is selected from the group consisting of lysine, arginine, and natural and synthetic derivatives thereof.

According to still further features in the described preferred embodiments the negatively charged amino acid is selected from the group consisting of aspartic acid, glutamic acid and natural and synthetic derivatives thereof.

According to yet a further aspect of the present invention there is provided a pharmaceutical composition for treating or preventing an amyloid-associated disease comprising as an active ingredient an antibody or an antibody fragment having an antigen recognition region capable of binding a peptide including the amino acid sequence X-Y or Y-X, wherein X is an aromatic amino acid and Y is any amino acid other than glycine, the peptide being at least 2 and no more than 15 amino acids in length and a pharmaceutical acceptable carrier or diluent.

According to still a further aspect of the present invention there is provided a method of treating or preventing an amyloid-associated disease in an individual, the method comprising providing to the individual therapeutically effective amount of an antibody or an antibody fragment having an antigen recognition region capable of binding a peptide including the amino acid sequence X-Y or Y-X, wherein X is an aromatic amino acid and Y is any amino acid other than glycine, the peptide being at least 2 and no more than 15 amino acids in length.

According to still a further aspect of the present invention there is provided a peptide having the general Formula:

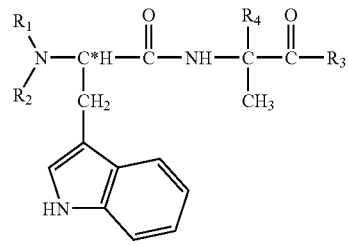

wherein:

C* is a chiral carbon having a D configuration.

$R_1$ and $R_2$ are each independently selected from the group consisting of hydrogen, alkyl, cycloalkyl, aryl, carboxy, C-thiocarb;

$R_3$ is selected from the group consisting of hydroxy, alkoxy, aryloxy, thiohydroxy, thioalkoxy, thioaryloxy, halo and amine; and $R_4$ is alkyl.

According to still a further aspect of the present invention there is provided a method of treating or preventing an amyloid-associated disease in an individual, the method comprising providing to the individual a therapeutically effective amount of a peptide having the general Formula:

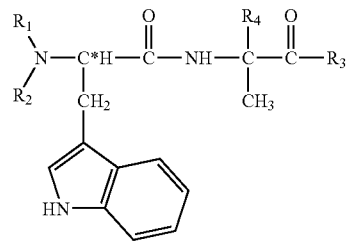

wherein:

C* is a chiral carbon having a D configuration.

$R_1$ and $R_2$ are each independently selected from the group consisting of hydrogen, alkyl, cycloalkyl, aryl, carboxy, C-thiocarb;

$R_3$ is selected from the group consisting of hydroxy, alkoxy, aryloxy, thiohydroxy, thioalkoxy, thioaryloxy, halo and amine; and $R_4$ is alkyl.

According to still further features in the described preferred embodiments $R_4$ is methyl.

According to still further features in the described preferred embodiments $R_1$ and $R_2$ are each hydrogen and $R_3$ is hydroxy.

According to still further features in the described preferred embodiments the peptide is a cyclic peptide.

The present invention successfully addresses the shortcomings of the presently known configurations by providing novel peptides, compositions and methods, which can be used to diagnose and treat amyloid associated diseases such as type II Diabetes mellitus.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
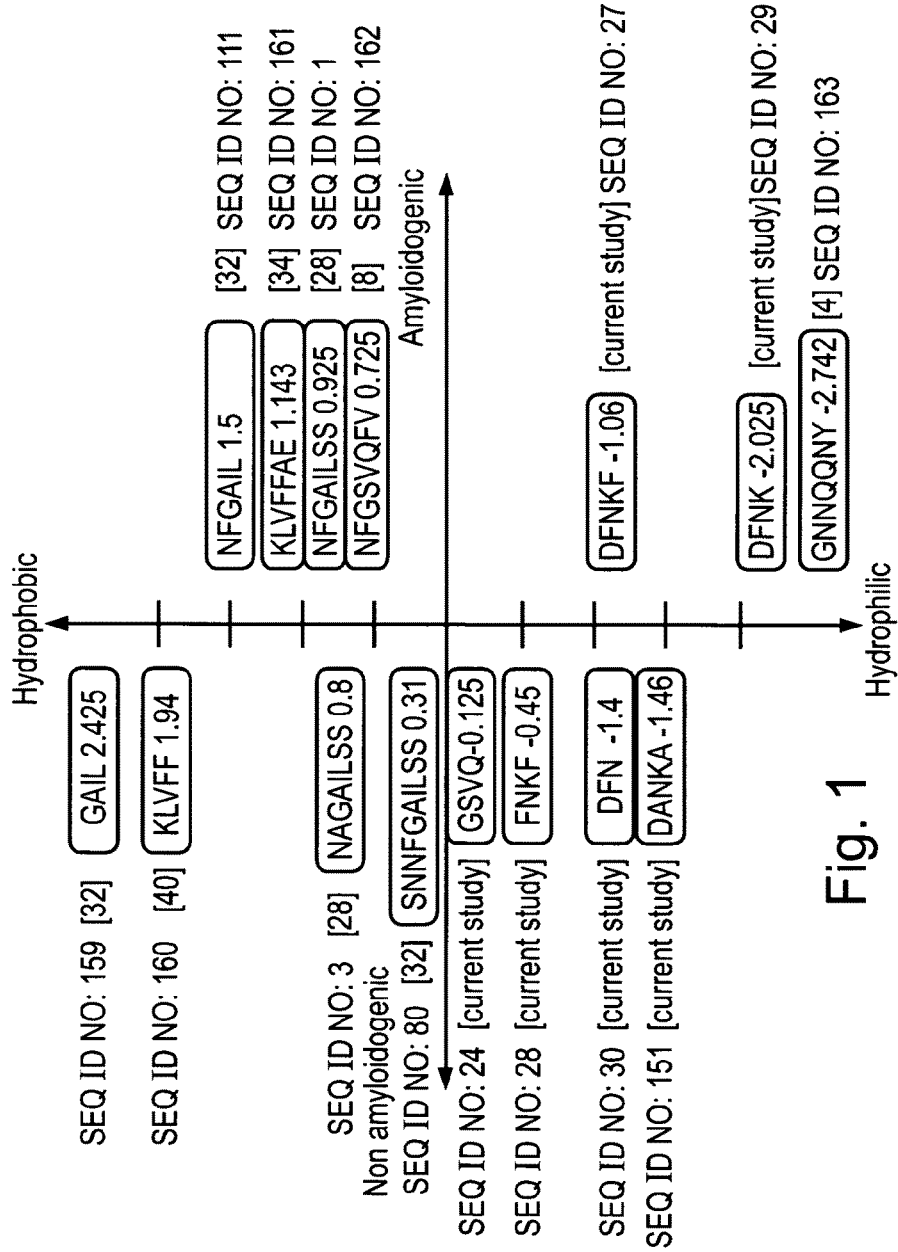

FIG. 1 is a schematic illustration depicting the self-assembly ability and hydrophobicity of a group of peptides from a number of amyloid proteins as deduced using Kyte and Dolittle scale. Note, that no correlation is observed between hydrophobicity and the amyloidogenic potential of the analyzed peptides. The only apparent indication for potential amyloid fibril formation in this group of peptide is a combination of aromatic nature and minimal length.

Figure 2B:
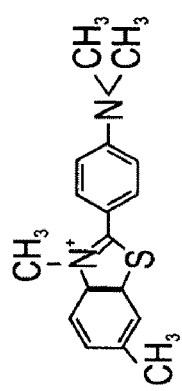
Figure 2C:
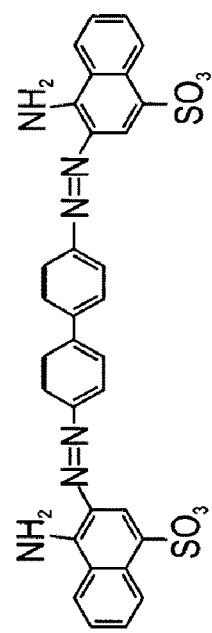
Figure 2A:
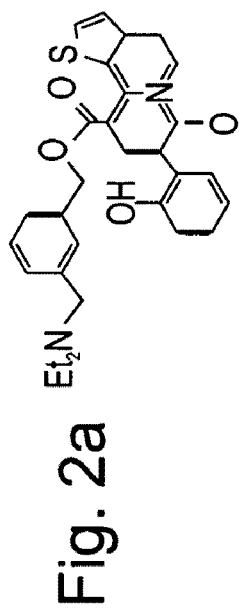

FIGS. 2a-c are schematic illustrations of amyloid binding with the inhibitory aromatic reagents: Ro 47-1816/001 (FIG. 2a), Thioflavin T (FIG. 2b) and CR dye (FIG. 2c).

Figures 3A, 3B, 3C:
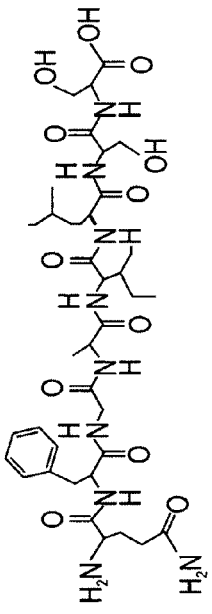

FIGS. 3a-c are schematic illustrations of a primary sequence comparison between human and rodent IAPP and the synthetic peptides of the present invention. FIG. 3a is a sequence alignment of human and rodent IAPP. A block indicates a seven amino acid sub-sequence illustrating the major inconsistencies between the sequences. The "basic amyloidogenic unit" is presented by bold letters and underlined. FIG. 3b illustrates the chemical structure of the wild type IAPP peptide (SEQ ID NO: 1). FIG. 3c illustrates the primary sequences and SEQ ID NOs. of the peptides derived from the basic amyloidogenic unit.

Figure 4A:
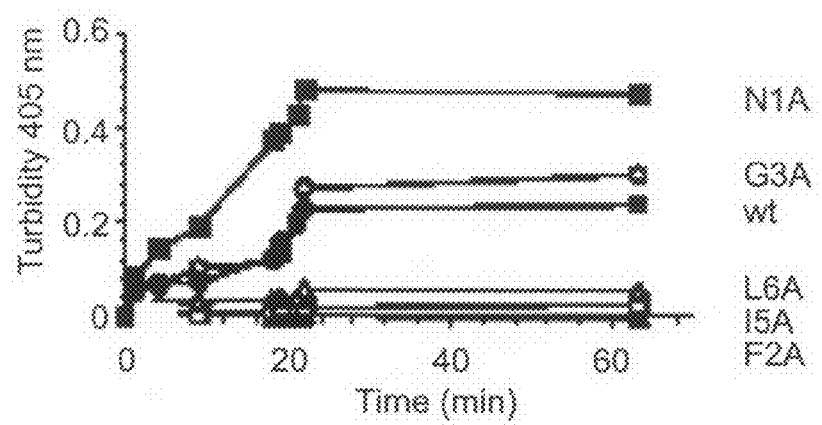
Figure 4B:
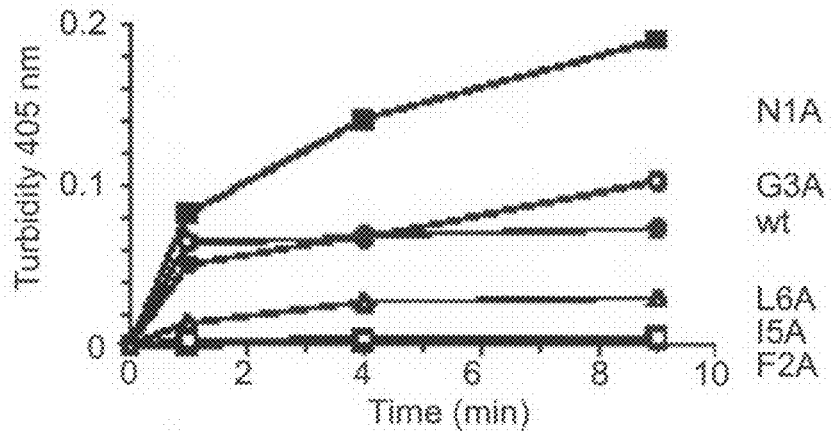

FIGS. 4a-b are graphs illustrating light absorbance at 405 nm as a function of time during fibril formation thus reflecting the aggregation kinetics of IAPP-derived peptides. The following symbols are used: closed squares—N1A, opened circles—G3A, closed circles—wild type, opened triangles—L6A, opened squares—I5A and closed triangles—F2A.

Figure 5:
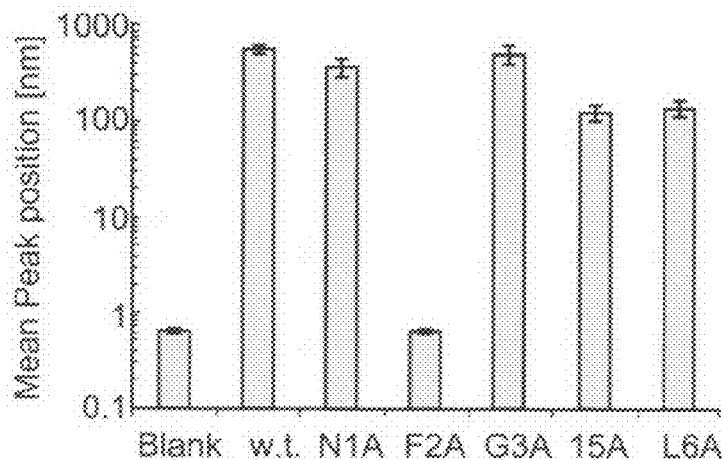

FIG. 5 is a histogram depicting mean particle size of assembled IAPP peptide and derivatives as measured by light scattering. Each column represents the results of 3-5 independent measurements.

FIGS. 6a-n are photomicrographs illustrating Congo Red binding to pre-assembled IAPP peptides. Normal field and polarized field micrographs are shown respectively for each of the following aged peptide suspensions: N1A peptide (FIGS. 6a-b), F2A peptide (FIGS. 6c-d), G3A peptide (FIGS. 6e-f), wild type peptide (FIGS. 6g-h), I5A peptide (FIGS. 6i-j) and L6A (FIGS. 6k-l). Buffer with Congo red reagent was used as a negative control visualized with and without polarized light as shown in FIGS. 6m and 6n, respectively.

Figure 7A:
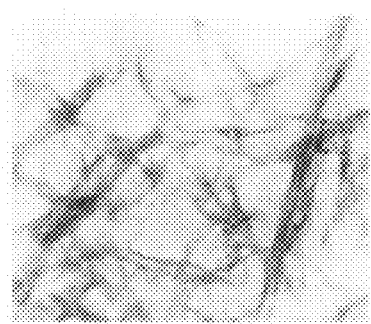
Figure 7B:
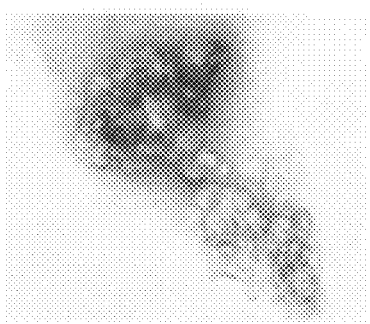
Figure 7C:
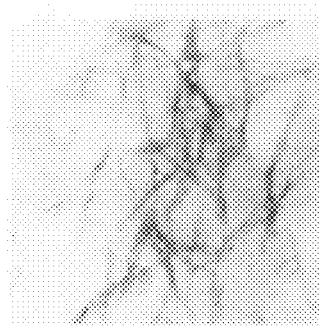
Figure 7D:
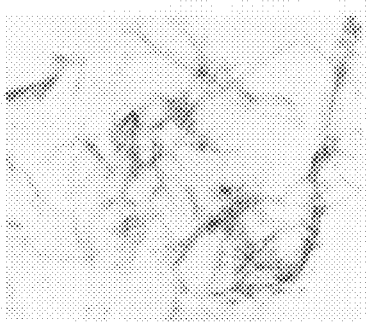
Figure 7E:
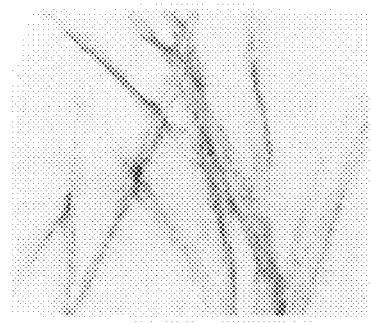
Figure 7F:
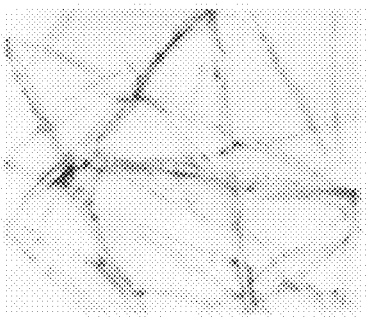

FIGS. 7a-f are electron micrographs of "aged" IAPP peptide and derivatives. N1A peptide (SEQ ID NO: 2, FIG. 7a), F2A peptide (SEQ ID NO: 3, FIG. 7b), G3A peptide (SEQ ID NO: 4, FIG. 7c), wild type peptide (SEQ ID NO: 1. FIG. 7d), I5A peptide (SEQ ID NO: 5, FIG. 7e) and L6A (SEQ ID NO: 6. FIG. 7f). The indicated scale bar represents 100 nm.

FIG. 8a is a nucleic acid sequence alignment of wild type hIAPP (SEQ ID NO: 1) and a corresponding sequence modified according to a bacterial codon usage. Modified bases are underlined.

Figure 8B:
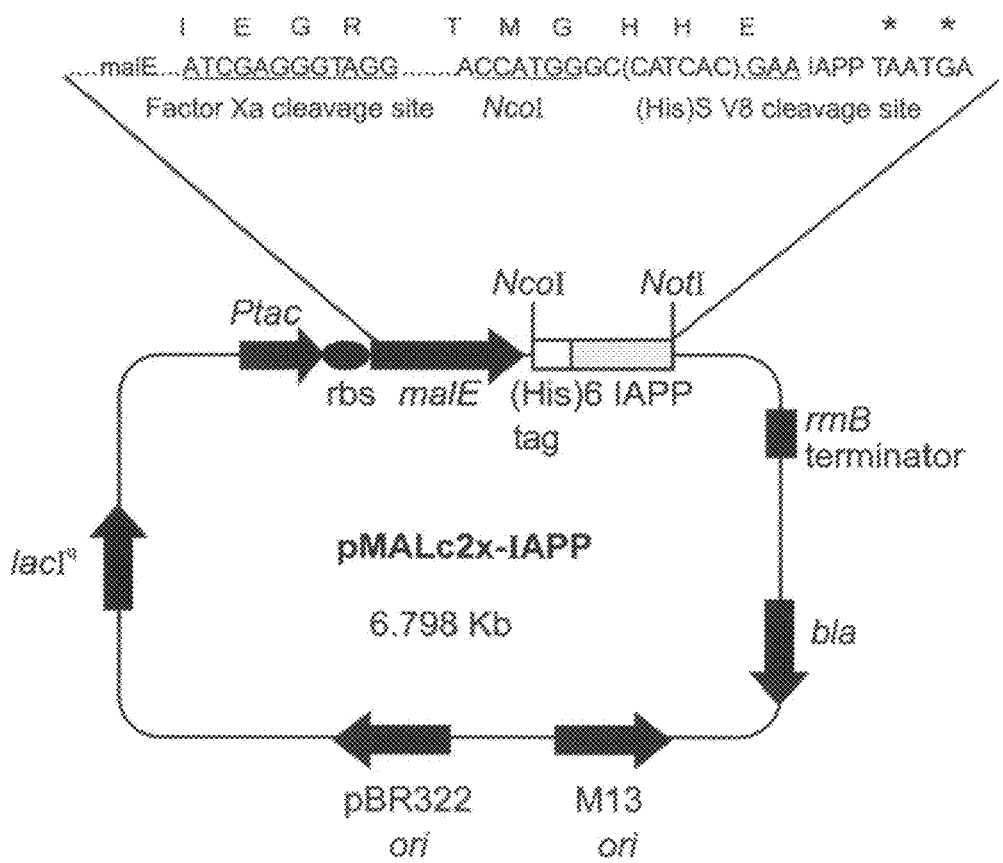

FIG. 8b is a schematic illustration of the pMALc2x-NN vector which is used for cytoplasmic expression of the 48 kDa MBP-IAPP protein. The V8 Ek cleavage site and the $(His)_6$ tag are fused C-terminally to the malE tag vector sequence. A factor Xa cleavage site for removal of the MBP tag is indicated.

Figure 9:
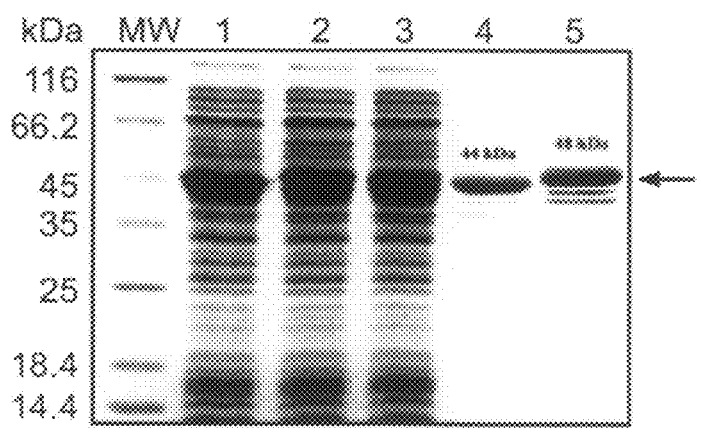

FIG. 9 is a protein gel GelCode Blue staining depicting bacterial expression and purification of MBP and MIBP-IAPP fusion protein. Bacterial cell extracts were generated and proteins were purified on an amylose resin column. Samples including 25 µg protein were loaded in each of Lanes 1-3 whereas 5 µg protein were loaded on each of lanes 4-5. Proteins were resolved on a 12% SDS-PAGE and visualized with GelCode Blue staining. A molecular weight marker is indicated on the left. Lane 1—0.5 mM IPTG-induced soluble extract of MBP. Lane 2—0.1 mM IPTG-induced soluble extract of MBP-IAPP. Lane 3—0.5 mM IPTG-induced soluble extract of MBP-IAPP. Lane 4—purified MBP. Lane 5—purified MBP-IAPP. An arrow marks the MBP-IAPP.

Figure 10A:
Figure 10B:
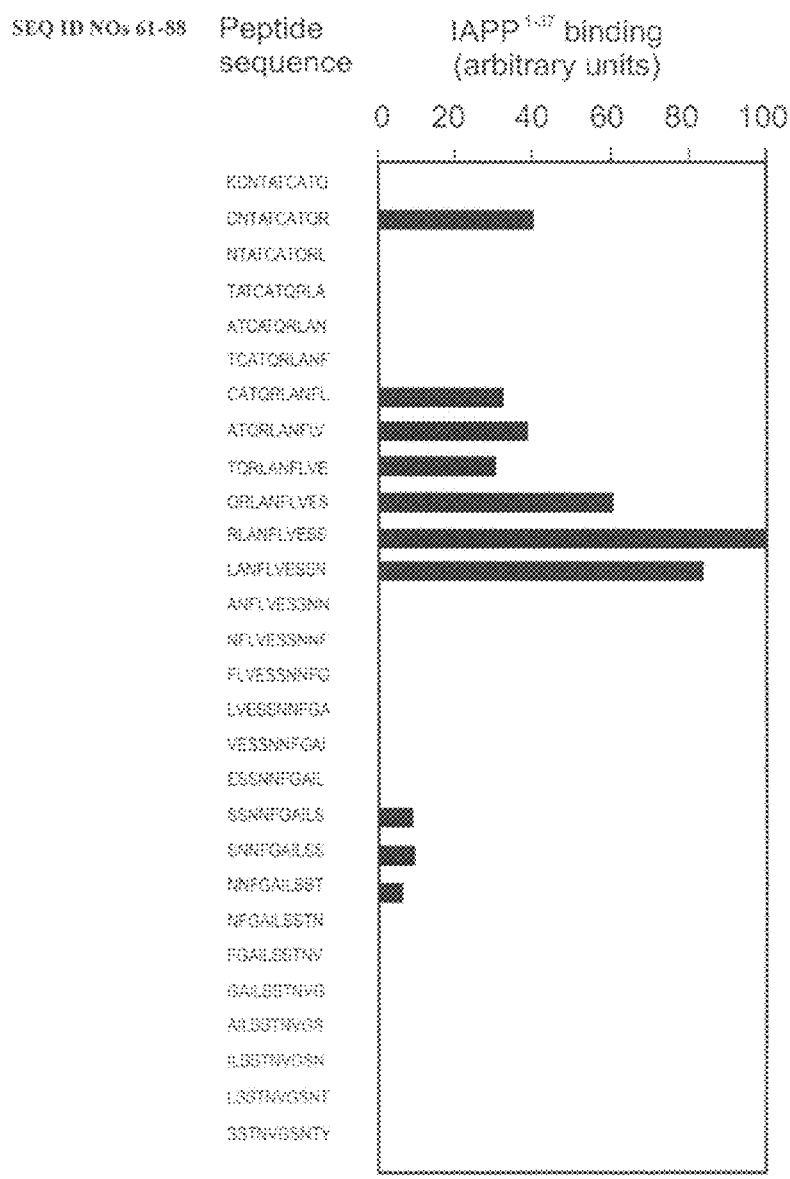

FIGS. 10a-b are a dot-blot image (FIG. 10a) and densitometric quantitation thereof (FIG. 10b) depicting putative amyloidogenic sequences in hIAPP (SEQ ID NOS: 61-88).

Figure 11:
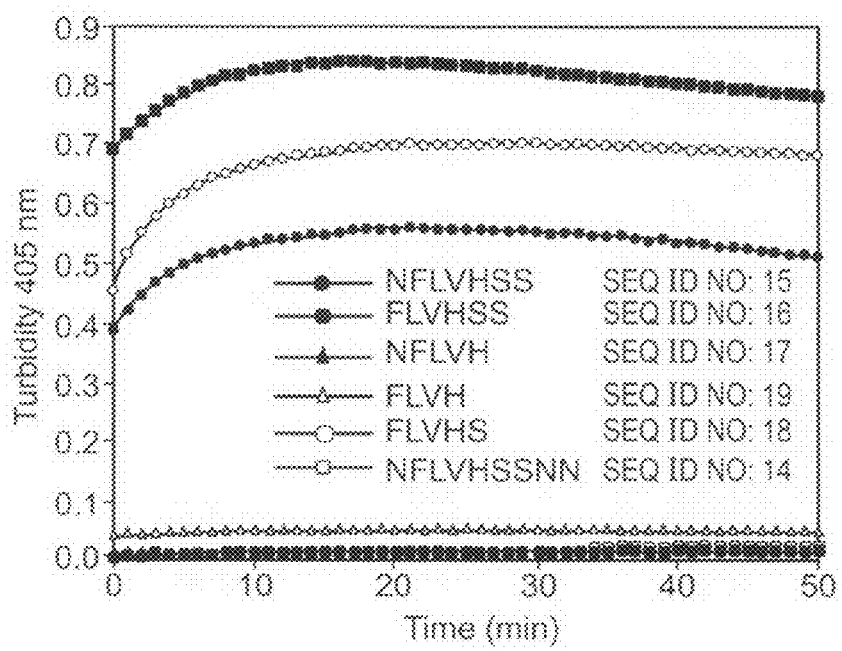

FIG. 11 is a graphic illustration depicting light absorbance at 405 nm as a function of time during fibril formation thus reflecting the aggregation kinetics of IAPP-derived peptides (SEQ ID NOs. 14-19).

Figure 12A:
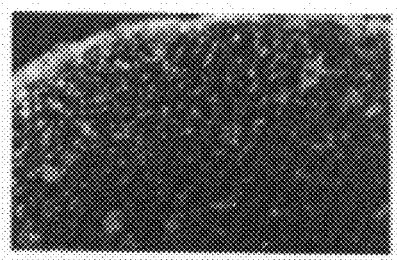
Figure 12B:
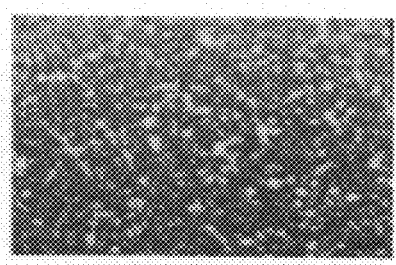
Figure 12C:
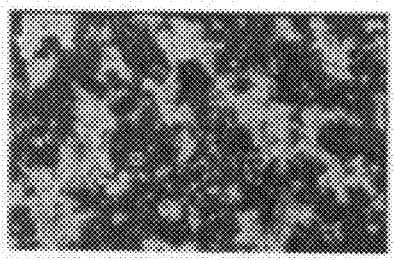
Figure 12D:
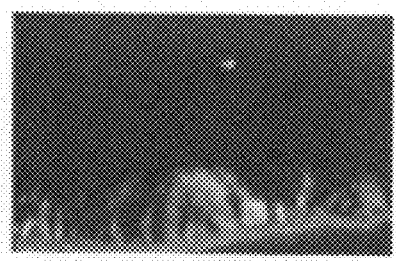
Figure 12E:
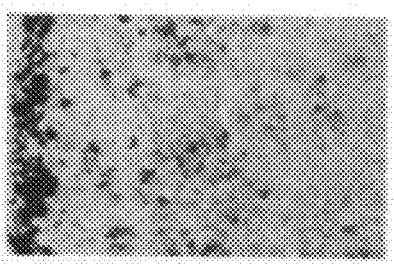
Figure 12F:
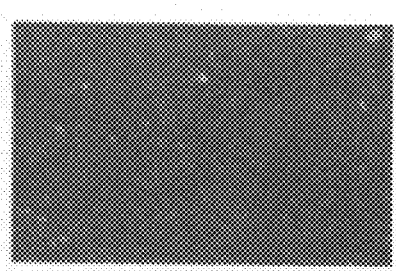

FIGS. 12a-f are photomicrographs illustrating Congo Red binding to pre-assembled IAPP peptides. Polarized field micrographs are shown for each of the following one day aged peptide suspensions: NFLVHSSNN peptide (SEQ ID NO: 14, FIG. 12a), NFLVHSS (SEQ ID NO: 15. FIG. 12b), FLVHSS (SEQ ID NO: 16, FIG. 12c), NFLVH (SEQ ID NO: 17, FIG. 12d), FLVHS (SEQ ID NO: 18, FIG. 12e) and FLVH (SEQ ID NO: 19. FIG. 12f).

FIGS. 13a-f are electron micrographs of "aged" IAPP peptides. NFLVHSSNN peptide (SEQ ID NO: 14, FIG. 13a), NFLVHSS (SEQ ID NO: 15, FIG. 13b), FLVHSS (SEQ ID NO: 16, FIG. 13c), NFLVH (SEQ ID NO: 17, FIG. 13d), FLVHS (SEQ ID NO: 18, FIG. 13e) and FLVH (SEQ ID NO: 19, FIG. 13f). The indicated scale bar represents 100 nm.

Figure 14:
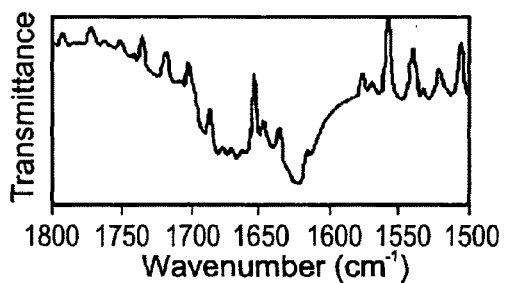
Figure 14:
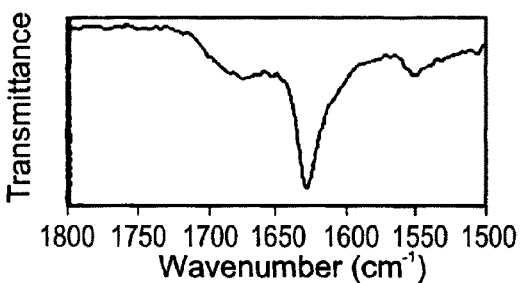
Figure 14:
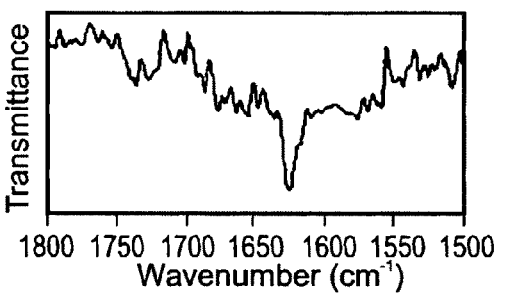
Figure 14:
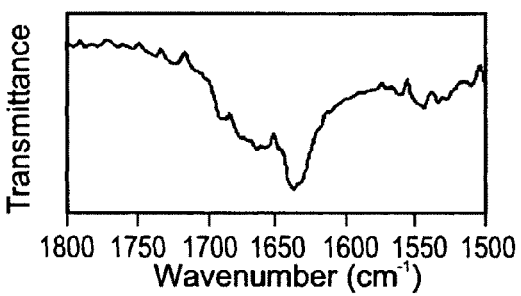
Figure 14:
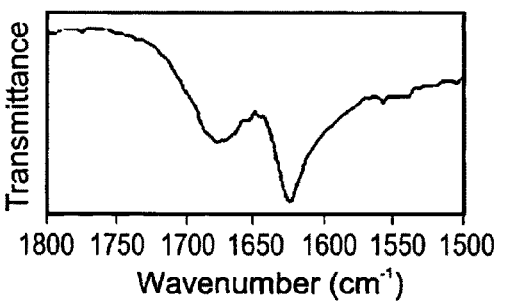
Figure 14:
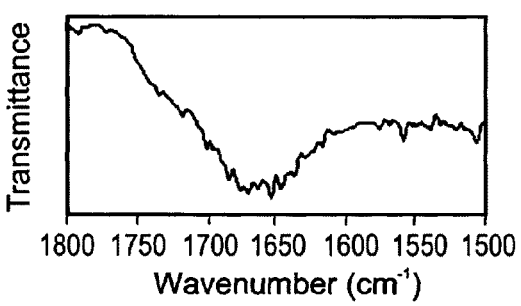

FIGS. 14a-f are graphs showing secondary structures in the insoluble IAPP aggregates as determined by Fourier transformed infrared spectroscopy. NFLVHSSNN peptide (SEQ ID NO: 14. FIG. 14a), NFLVHSS (SEQ ID NO: 15, FIG. 14b), FLVHSS (SEQ ID NO: 16, FIG. 14c), NFLVH (SEQ ID NO: 17, FIG. 14d), FLVHS (SEQ ID NO: 18, FIG. 14e) and FLVH (SEQ ID NO: 19, FIG. 14f).

Figure 15:
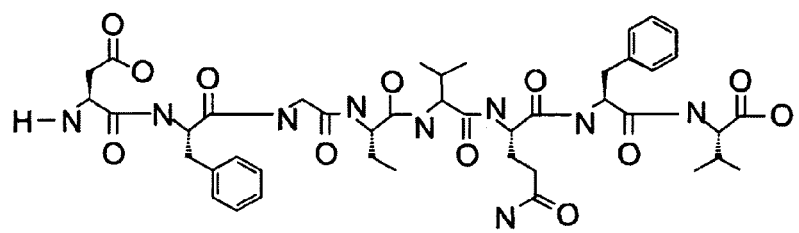

FIG. 15 is a chemical structure of a previously reported amyloidogenic peptide fragment of Medin [Haggqvist (1999) Proc. Natl. Acad. Sci. USA 96:8669-8674].

Figures 16A, 16B:
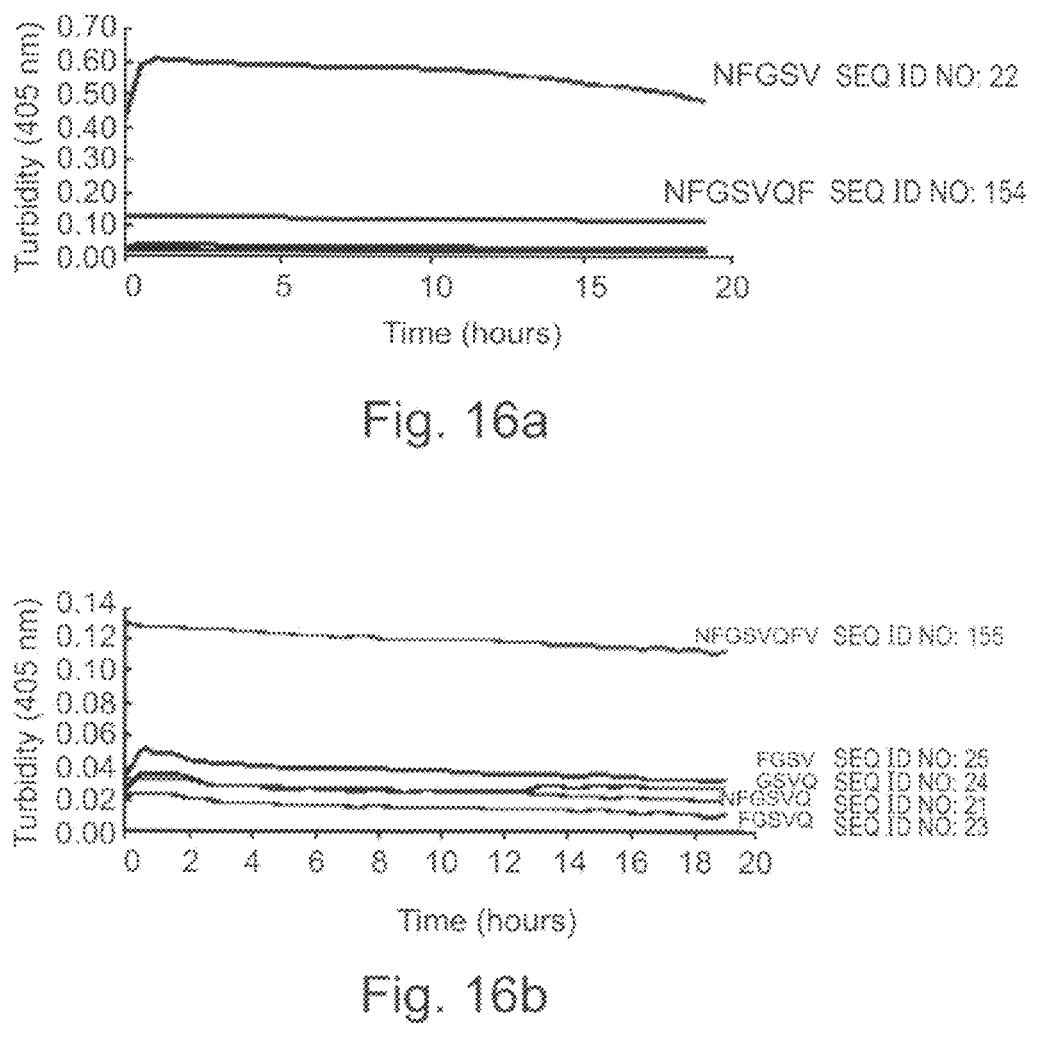

FIGs. 16a-b are graphs illustrating light absorbance at 405 nm as a function of time during fibril formation thus reflecting the aggregation kinetics of Medin-derived peptides (SEQ ID NOs: 21-25, 154-155). FIG. 16a illustrates a short-term kinetic assay. FIG. 16b illustrates a long-term kinetic assay.

FIGS. 17a-f are electron micrographs of "aged" Medin-derived peptides. NFGSVQFA (SEQ ID NO: 156)—FIG. 17a, NFGSVQ (SEQ ID NO: 21)—FIG. 17b, NFGSV (SEQ ID NO: 22)—FIG. 17c, FGSVQ (SEQ ID NO: 23)—FIG. 17d, GSVQ (SEQ ID NO: 24)—FIG. 17e and FGSV (SEQ ID NO: 25)—FIG. 17f. The indicated scale bar represents 100 nm.

FIGS. 18a-f are photomicrographs illustrating Congo Red binding to pre-assembled Medin-derived peptides. Polarized field micrographs are shown for each of the following aged peptide suspensions: NFGSVQFA (SEQ ID NO: 156)—FIG. 18a, NFGSVQ (SEQ ID NO: 21)—FIG. 18b, NFGSV (SEQ ID NO: 22)—FIG. 18c, FGSVQ (SEQ ID NO: 23)—FIG. 18d, GSVQ (SEQ ID NO: 24)—FIG. 18e and FGSV (SEQ ID NO: 25)—FIG. 18f.

FIGS. 19a-c depict the effect of an alanine mutation on the amyloidogenic features of the hexapeptide amyloidogenic fragment of Medin. FIG. 19a—is a graph illustrating light absorbance at 405 nm as a function of time during fibril formation thus reflecting the aggregation kinetics of Medin-derived alanine mutant (SEQ ID NOs: 21, 26); FIG. 19b is an electron micrograph of "aged" Medin-derived alanine mutant, The scale bar represents 100 nm; FIG. 19c is a photomicrograph illustrating Congo Red binding to pre-assembled Medin-derived peptide mutant.

FIGS. 20a-b are the amino acid sequence of human Calcitonin (FIG. 20a, SEQ ID NO: 158) and chemical structure of an amyloidogenic peptide fragment of human Calcitonin (FIG. 20b). Underlined are residues 17 and 18 which are important to the oligomerization state and hormonal activity of Calcitonin [Kazantzis (2001) Eur. J. Biochem. 269:780-791].

FIGS. 21a-d are electron micrographs of "aged" Calcitonin-derived peptides. DFNKF (SEQ ID NO: 27)—FIG. 21a, DFNK (SEQ ID NO: 29)—FIG. 21b, FNKF (SEQ ID NO: 28)—FIG. 21c and DFN (SEQ ID NO: 30)—FIG. 21d. The indicated scale bar represents 100 nm.

FIGS. 22a-d are photomicrographs illustrating Congo Red binding to pre-assembled Calcitonin-derived peptides. Polarized field micrographs are shown for each of the following aged peptide suspensions: DFNKF (SEQ ID NO: 27)—FIG. 22a, DFNK (SEQ ID NO: 29)—FIG. 22b, FNKF (SEQ ID NO: 28)—FIG. 22c and DFN (SEQ ID NO: 30)—FIG. 22d.

Figure 23:
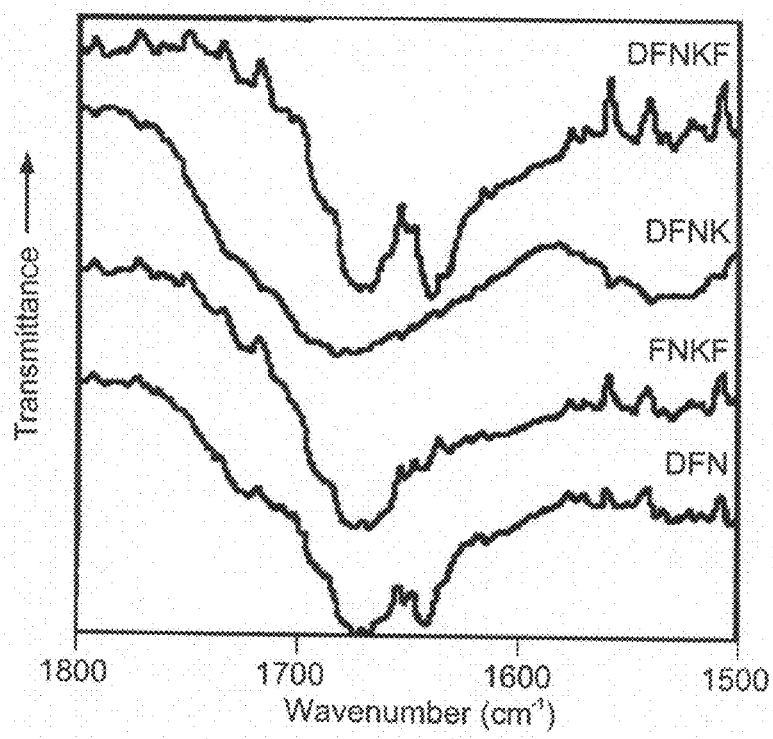

FIG. 23 is a graphic illustration showing secondary structures in the insoluble Calcitonin aggregates as determined by Fourier transformed infrared spectroscopy (SEQ ID NOs: 27-30).

Figure 24A:
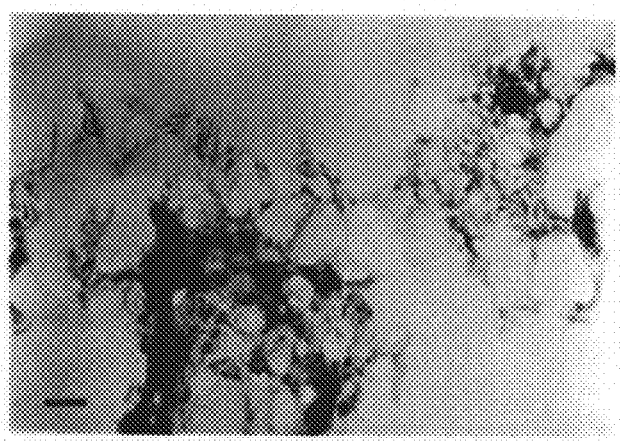
Figure 24B:
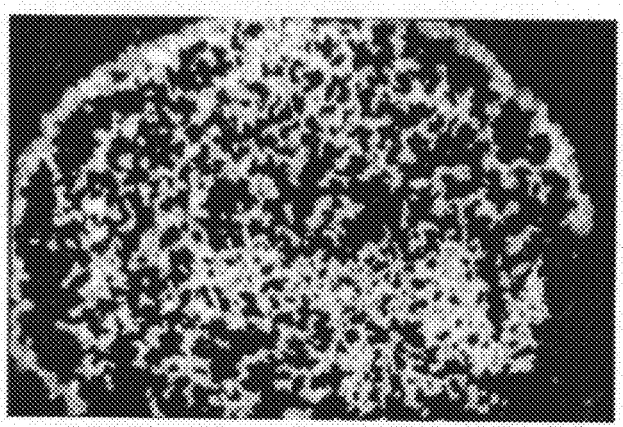
Figure 24C:
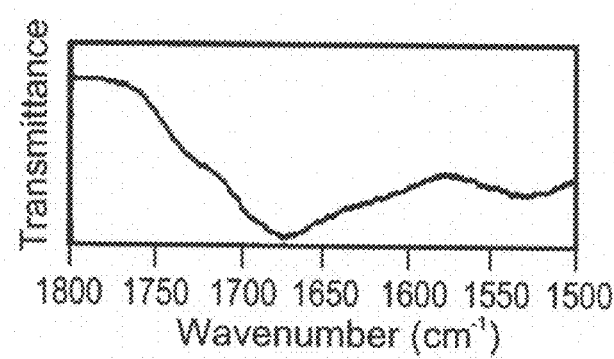

FIGS. 24a-c depict the effect an alanine mutation on the amyloidogenic features of the pentapeptide amyloidogenic fragment of Calcitonin (SEQ ID NO: 31). FIG. 24a is an electron micrograph of "aged" Calcitonin-derived alanine mutant. The scale bar represents 100 nm; FIG. 24b—is a photomicrograph illustrating Congo Red binding to pre-assembled Calcitonin-derived peptide mutant; FIG. 24c is a graph showing secondary structures in the mutant peptide as determined by Fourier transformed infrared spectroscopy.

Figure 25:
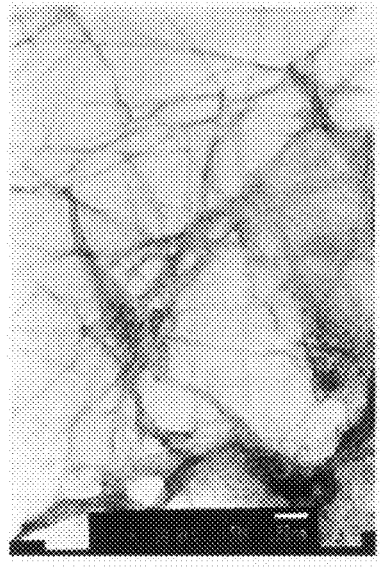

FIG. 25 is an electron micrograph depicting self-assembly of "aged" Lactotransferrin-derived peptide (SEQ ID NO: 32). The scale bar represents 100 nm.

Figure 26:
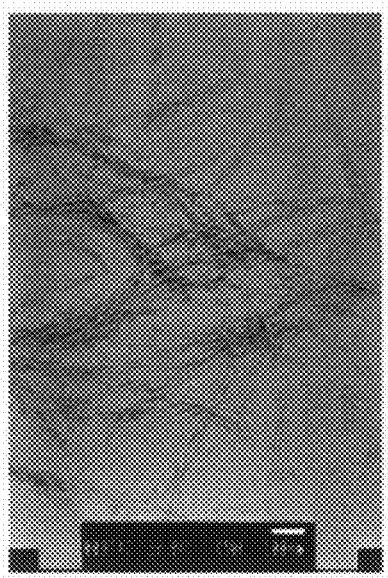

FIG. 26 is an electron micrograph depicting self-assembly of "aged" Serum amyloid A protein-derived peptide (SEQ ID NO: 33). The scale bar represents 100 nm.

Figure 27:
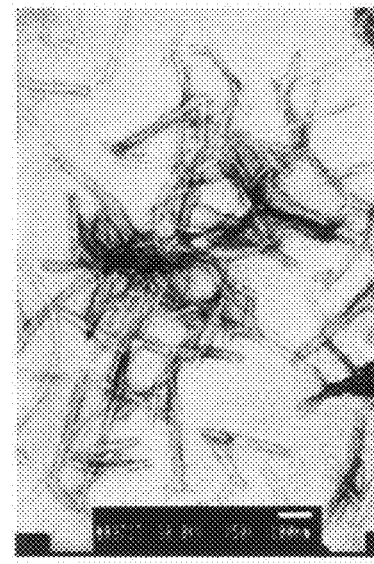

FIG. 27 is an electron micrograph depicting self-assembly of "aged" BriL-derived peptide (SEQ ID NO: 34). The scale bar represents 100 nm.

Figure 28:
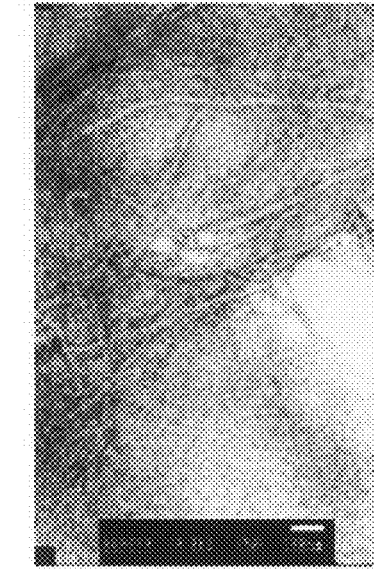

FIG. 28 is an electron micrograph depicting self-assembly of "aged" Gelsolin-derived peptide (SEQ ID NO: 35). The scale bar represents 100 nm.

Figure 29:

FIG. 29 is an electron micrograph depicting self-assembly of "aged" Serum amyloid P-derived peptide (SEQ ID NO: 36). The scale bar represents 100 nm.

Figure 30:
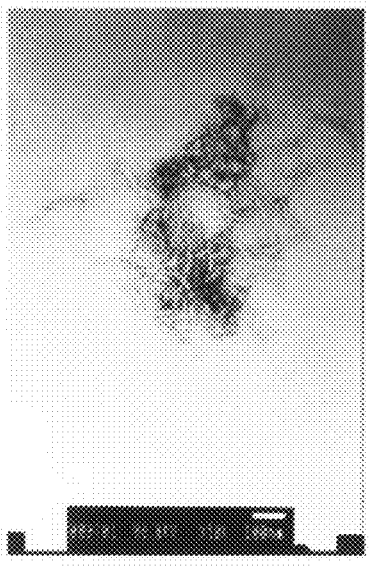

FIG. 30 is an electron micrograph depicting self-assembly of "aged" Immunoglobulin light chain-derived peptide (SEQ ID NO: 37). The scale bar represents 100 nm.

Figure 31:
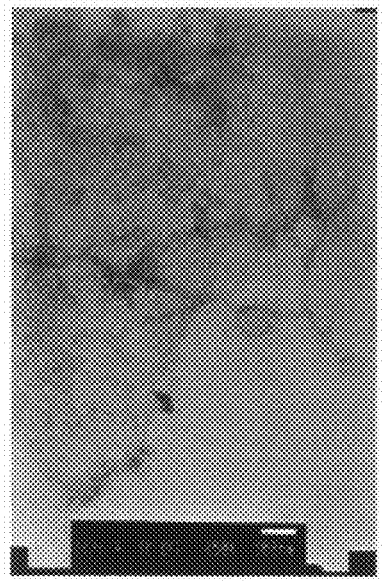

FIG. 31 is an electron micrograph depicting self-assembly of "aged" Cystatin C-derived peptide (SEQ ID NO: 38). The scale bar represents 100 nm.

Figure 32:
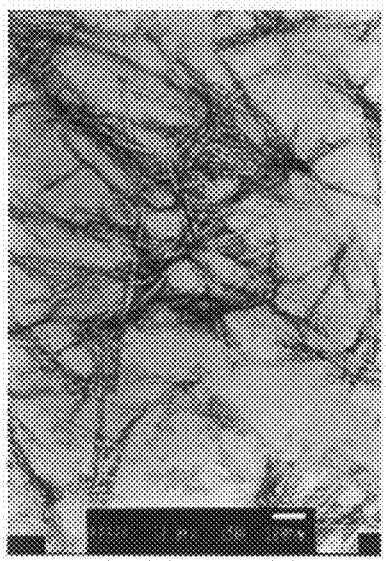

FIG. 32 is an electron micrograph depicting self-assembly of "aged" Transthyretin-derived peptide (SEQ ID NO: 39). The scale bar represents 100 nm.

Figure 33:
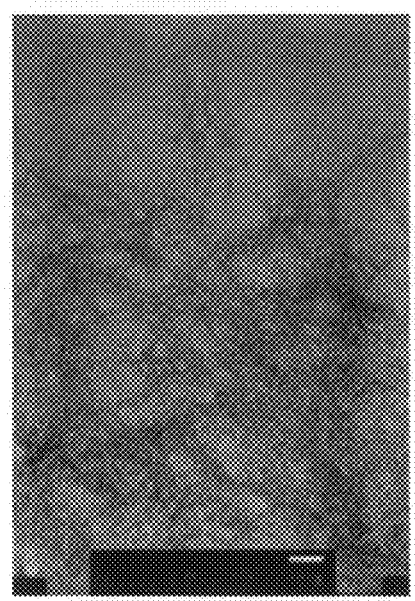

FIG. 33 is an electron micrograph depicting self-assembly of "aged" Lysozyme-derived peptide (SEQ ID NO: 40). The scale bar represents 100 nm.

Figure 34:
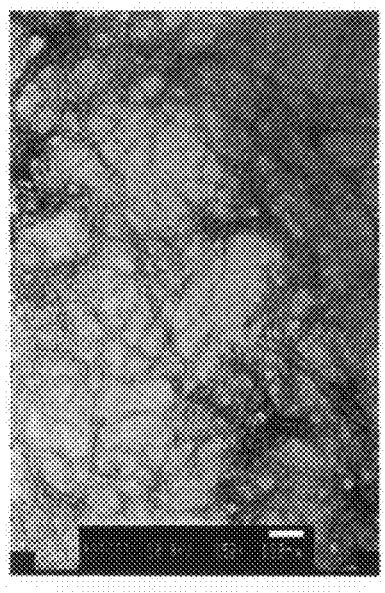

FIG. 34 is an electron micrograph depicting self-assembly of "aged" Fibrinogen-derived peptide (SEQ ID NO: 41). The scale bar represents 100 nm.

Figure 35:

FIG. 35 is an electron micrograph depicting self-assembly of "aged" Insulin-derived peptide (SEQ ID NO: 42). The scale bar represents 100 nm.

Figure 36:
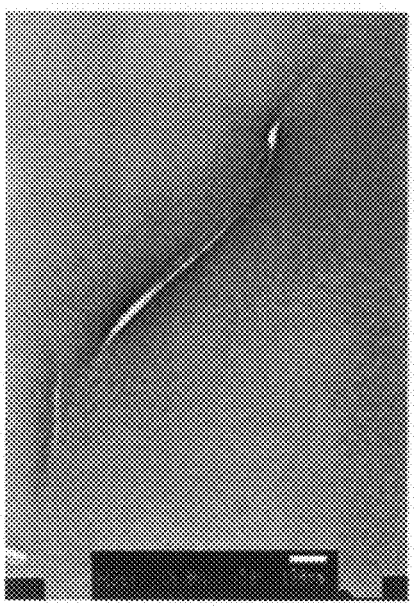

FIG. 36 is an electron micrograph depicting self-assembly of "aged" Prolactin-derived peptide (SEQ ID NO: 43). The scale bar represents 100 nm.

Figure 37:
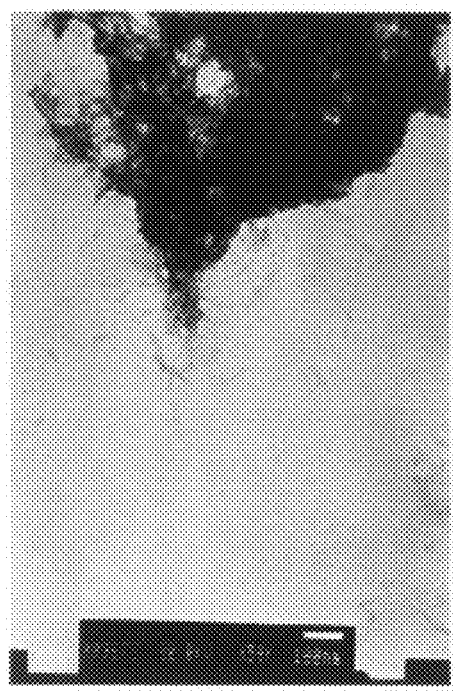

FIG. 37 is an electron micrograph depicting self-assembly of "aged" Beta 2 microglobulin-derived peptide (SEQ ID NO: 44). The scale bar represents 100 nm.

Figure 38:
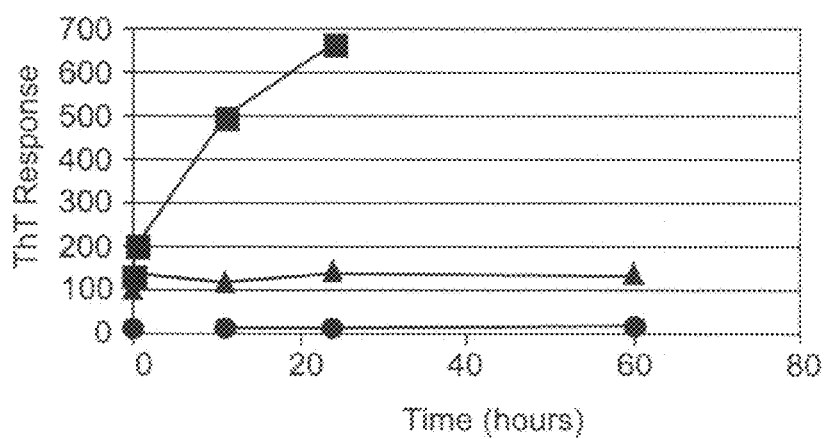

FIG. 38 is a graphic representation of the effect of an inhibitory peptide on IAPP self-assembly (SEQ ID NO: 45). Squares—wild type (wt) IAPP peptide; triangles—wt-IAPP+ inhibitory peptide; circles—no peptides.

Figure 39:
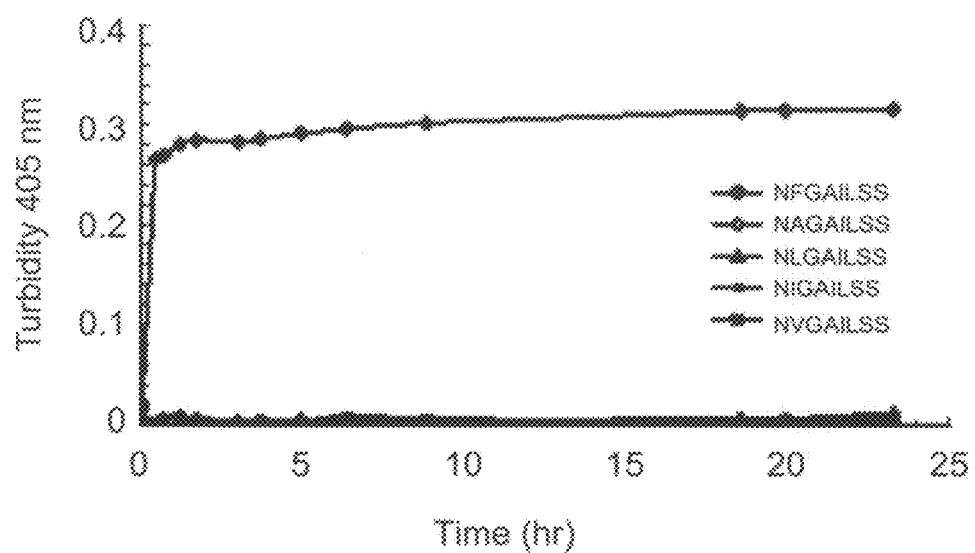

FIG. 39 is a graphic illustration depicting light absorbance at 405 nm as a function of time during fibril formation thus reflecting the aggregation kinetics of IAPP-derived peptides (SEQ ID NOs. 46-49).

Figure 40:
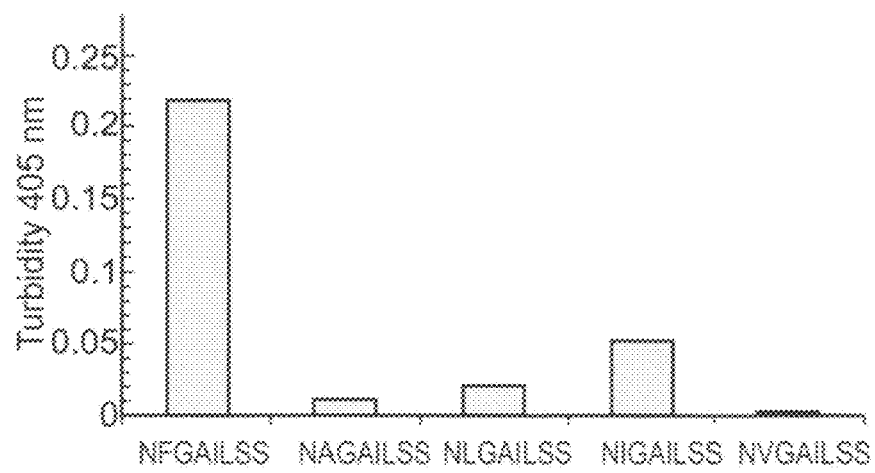

FIG. 40 is a histogram representation illustrating turbidity of IAPP analogues following seven day aging (SEQ ID NOs. 46-49).

FIG. 41a-f are electron micrographs of "aged" IAPP analogues. NEGAILSS (SEQ ID NO: 461)—FIG. 41a; NFGAILSS (SEQ ID NO: 461)—FIG. 41b; NIGAILSS (SEQ ID NO: 47)—FIG. 41c; NLGAILSS (SEQ ID NO: 48)—FIG. 41d; NVGAILSS (SEQ ID NO: 49)—FIG. 41e and NAGAILSS (SEQ ID NO: 89, 91, 92)—FIG. 41f. The indicated scale bar represents 100 nm.

FIGS. 42a-c illustrate the binding of IAPP-NFGAILSS to analogues of the minimal amyloidogenic sequence SNNX-GAILSS (SEQ ID NO: 90. X=any natural amino acid but cysteine). FIG. 42a shows short exposure of the bound peptide-array. FIG. 42b shows long exposure of the bound peptide-array. FIG. 42c shows quantitation of the short exposure (FIG. 42a) using densitometry and arbitrary units (SEQ ID NOs: 91-110).

FIG. 43a is a Ramachandran plot showing the sterically allowed regions for all residues (yellow for fully allowed, orange for partially allowed), for L-Proline (blue) and for the achiral Aib residue (magenta).

FIGS. 43b-c are schematic illustrations showing the chemical structure of the longer wild-type IAPP peptide (ANFLVH, SEQ ID NO: 124, FIG. 43b) and the Aib modified structure thereof peptide (Aib-NF-Aib-VH, SEQ ID NO: 125, FIG. 43c). Functional groups suitable for modification are marked in blue (FIG. 43b) while modified groups are marked in red (FIG. 43c).

Figure 44A:
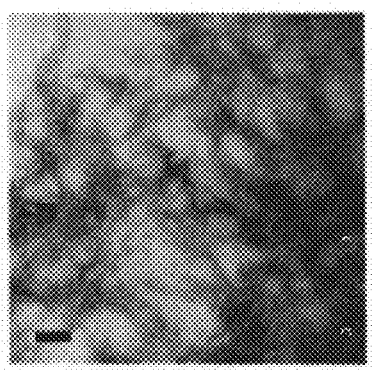
Figure 44B:
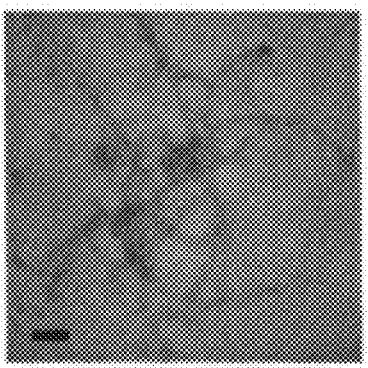
Figure 44C:
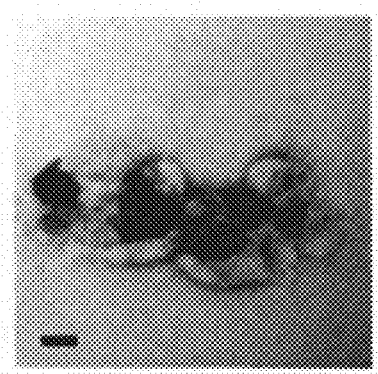
Figure 44D:
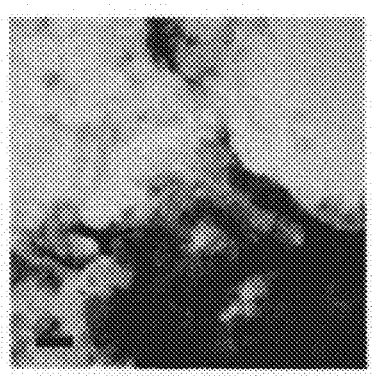

FIGS. 44a-d are electron micrographs of "aged" IAPP analogues. FIG. 44a—ANFLVH (SEQ ID NO: 124); FIG. 44b—ANFLV (SEQ ID NO: 126); FIG. 44c—Aib-NF-Aib-VH (SEQ ID NO: 125); and FIG. 44d—Aib-NF-Aib-V (SEQ ID NO: 127). The indicated scale bar represents 100 nm.

Figure 45A:
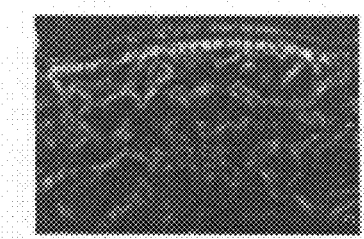
Figure 45B:
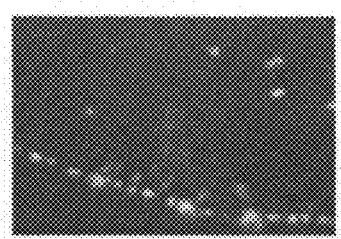
Figure 45C:
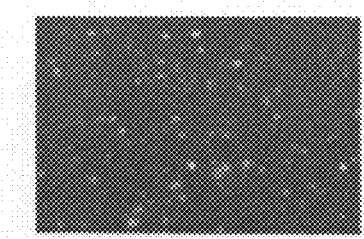
Figure 45D:
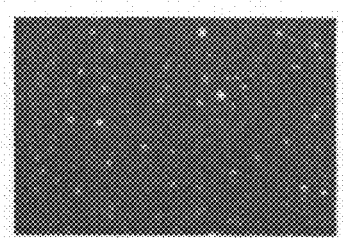

FIGS. 45a-d are photomicrographs illustrating Congo Red binding to pre-assembled wild type and Aib modified IAPP peptides. Polarized field micrographs are shown for each of the following aged (i.e., 11 days) peptide suspensions. FIG. 45a—ANFLVH (SEQ ID NO: 124); FIG. 45b—ANFLV (SEQ ID NO: 126); FIG. 45c—Aib-NF-Aib-VH (SEQ ID NO: 125); FIG. 45d—Aib-NF-Aib-V (SEQ ID NO: 127).

Figure 46A:
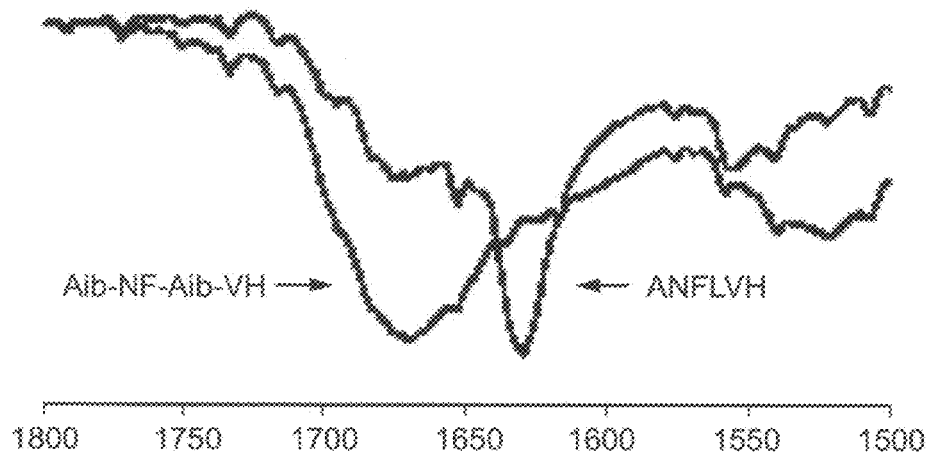
Figure 46B:
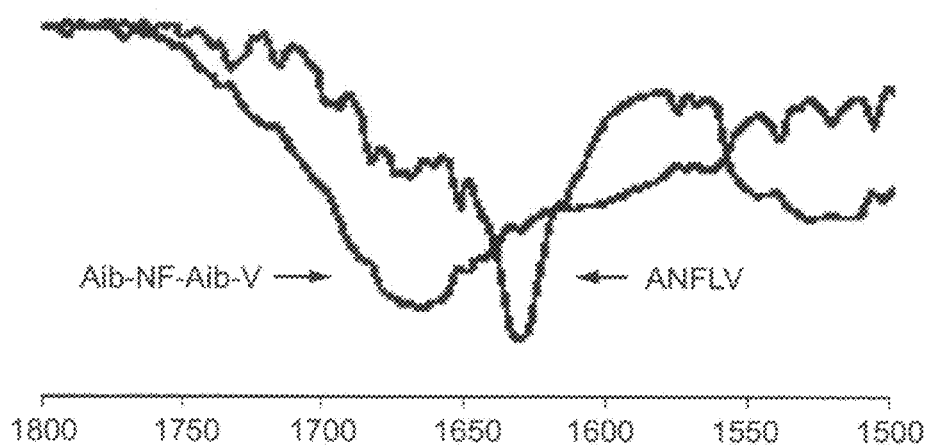

FIGS. 46a-b are graphs showing secondary structures in the insoluble wild type and Aib modified hIAPP aggregates as determined by Fourier transformed infrared spectroscopy (FT-IR). FIG. 46a—wild-type peptide ANFLVH (SEQ ID NO: 124) and the corresponding Aib modified peptide (SEQ ID NO: 125) as designated by arrows. FIG. 46b—wild-type ANFLVH (SEQ ID NO: 126) and the corresponding Aib modified peptide (SEQ ID NO: 127) as designated by arrows.

Figure 47:
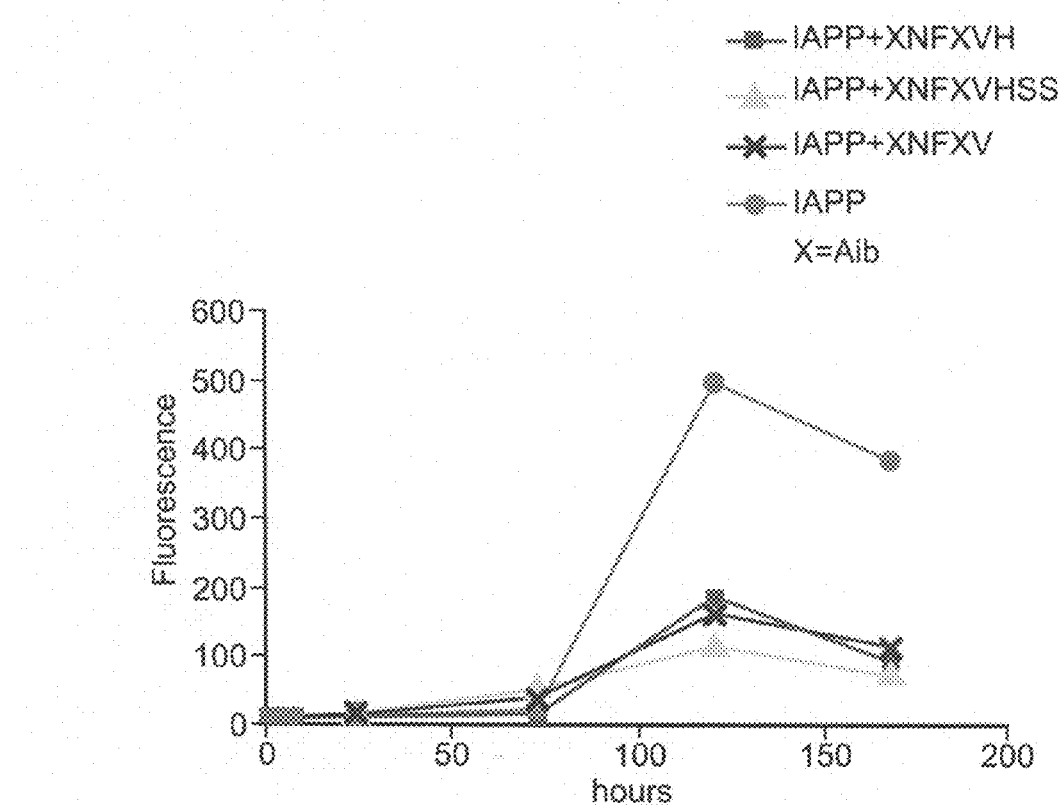

FIG. 47 is a graph showing the inhibitory effect of Aib modified peptides on amyloid fibril formation. Wild type IAPP (SEQ ID NO: 1) was incubated alone or with the various peptides of the present invention (SEQ ID NO: 125, 127 and 157). Fibril formation as a function of time was determined using ThT fluorescence.

Figure 48:
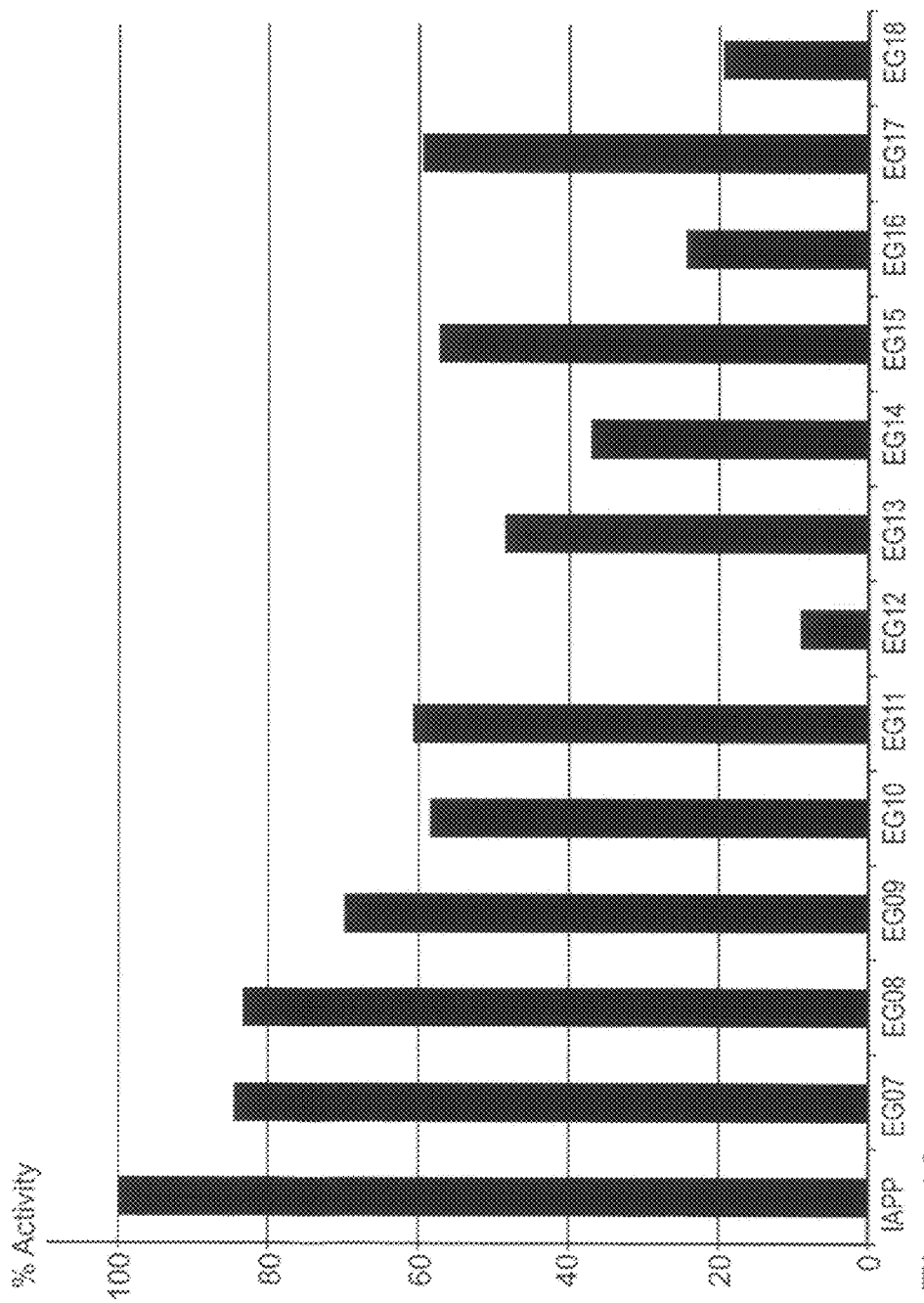

FIG. 48 is a histogram showing the inhibitory effect of short aromatic sequences (SEQ ID NOs. 112-123) on IAPP self-assembly.

Figure 49A:
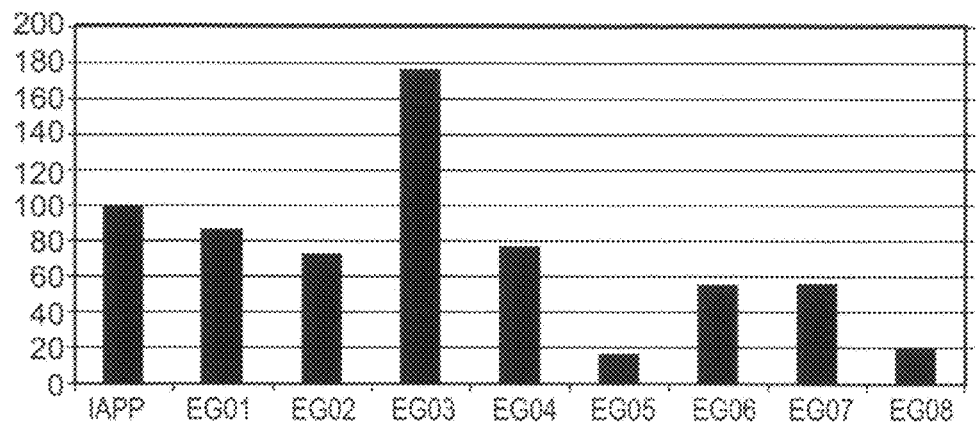
Figure 49B:
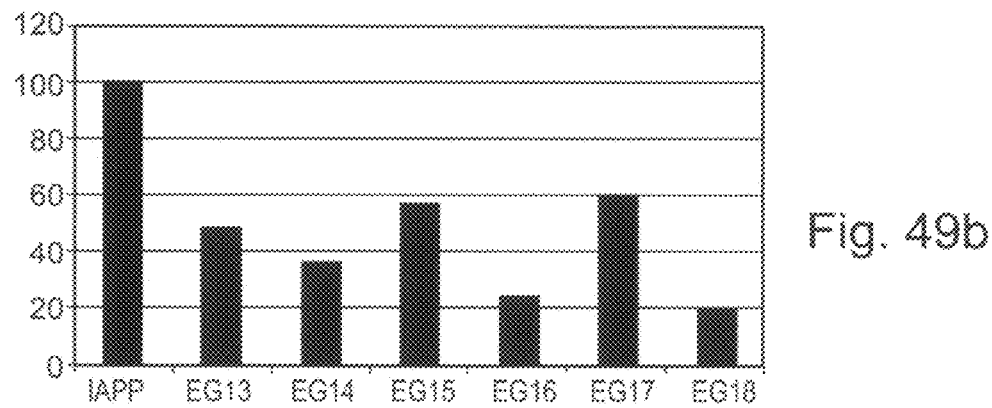
Figure 49C:
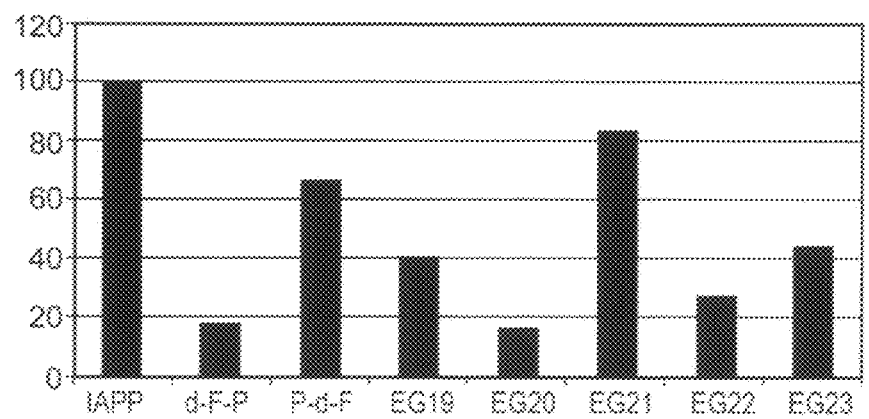
Figure 49D:
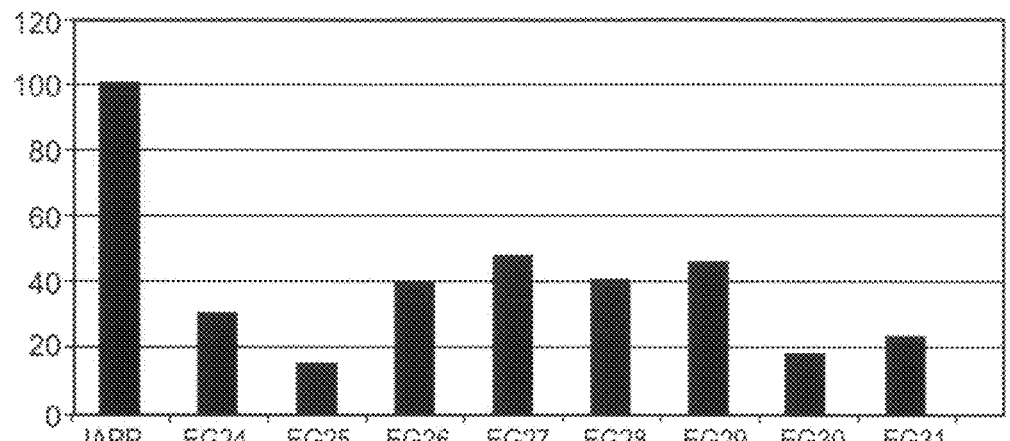

FIGS. 49a-d are graphs depicting iterative cycles of selection of IAPP fibrilization inhibitors. Fibrilization was monitored by ThT fluorescence assay. Fluorescence values of IAPP alone (4 µM) or in the presence of assayed compounds (40 µM) were tested. Measurements were taken once IAPP fluorescence reached a plateau. IAPP fluorescence was arbitrary set as 100. FIG. 49a shows the results of the first round of selection of IAPP fibrilization inhibitors. EG1=D-Phe-D-Phe-D-Pro (SEQ ID NO: 128); EG2=Aib-D-Phe-D-Asn-Aib (SEQ ID NO: 129); EG3=D-Phe-D-Asn-D-Pro (SEQ ID NO: 130); EG4 Aib-Asn-Phe-Aib (SEQ ID NO: 131); EG5=Gln-Lys-Leu-Val-Phe-Phe (SEQ ID NO: 132); EG6=Tyr-Tyr (SEQ ID NO: 133); EG7=Tyr-Tyr-NH2 (SEQ ID NO: 112); EG8=Aib-Phe-Phe (SEQ ID NO: 113). FIG. 49b shows the results of the second round of selection of IAPP fibrilization inhibitors. EG13=Asn-Tyr-Aib (SEQ ID NO: 118); EG14Asn-Tyr-Pro (SEQ ID NO: 119); EG15=D-Pro-D-Tyr-D-Asn (SEQ ID NO: 120); EG16=D-Tyr-Aib (SEQ ID NO: 121); EG17=D-Pro-D-Tyr (SEQ ID NO: 122); EG18=D-Tyr-D-Pro (SEQ ID NO: 123). FIG. 49c shows the results of the third round of selection of IAPP fibrilization inhibitors. d-F-P=D-Phe-Pro (SEQ ID NO: 147); P-d-F=Pro-D-Phe (SEQ ID NO: 148); EG19=Asn-Tyr-Tyr-Pro (SEQ ID NO: 134); EG20=Tyr-Tyr-Aib (SEQ ID NO: 135); EG21=Aib-Tyr-Tyr (SEQ ID NO: 136); EG22=Aib-Tyr-Tyr-Aib (SEQ ID NO: 137); EG23=D-Asn-Tyr-Tyr-D-Pro (SEQ ID NO: 138). FIG. 49d shows the results of the forth round of selection of IAPP fibrilization inhibitors. EG24=Pro-Tyr-Tyr (SEQ ID NO: 139); EG25=Tyr-Tyr-Pro (SEQ ID NO: 140); EG26=Pro-Tyr-Tyr-Pro (SEQ ID NO: 141); EG27=D-Tyr-D-Tyr (SEQ ID NO: 142); EG28=D-Pro-Aib (SEQ ID NO: 143); EG29=D-Phe-D-Pro (SEQ ID NO: 144); EG30D-Trp-Aib (SEQ ID NO: 145); EG31=D-Trp-D-Pro (SEQ ID NO: 146).

Figure 50:
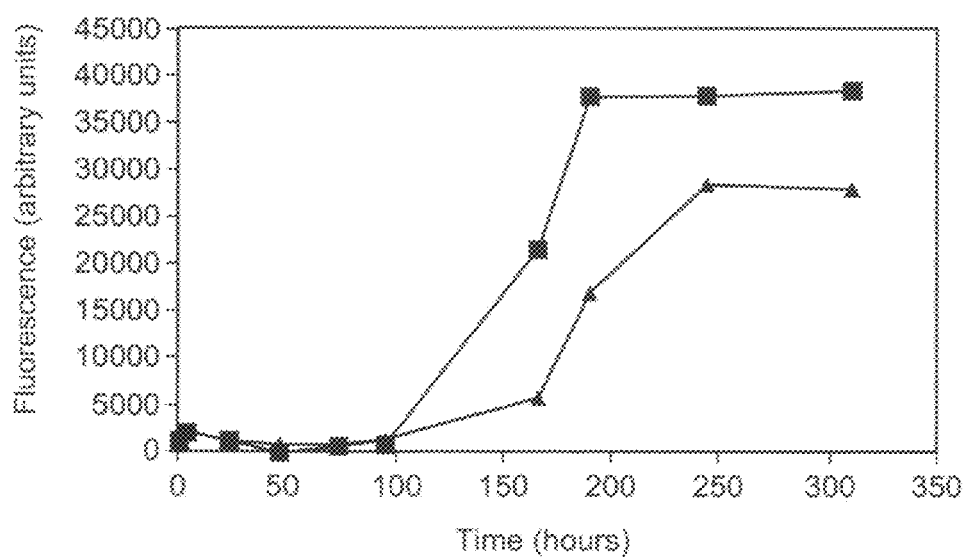

FIG. 50 is a graph depicting inhibition of Aβ (1-40) fibril formation by D-Trp-Aib (SEQ ID NO: 145). $A\beta_{1-40}$ stock solution was diluted to a final concentration of 5 µM in 100 mM NaCl, 10 mM sodium phosphate buffer (pH 7.4) with 10 µM D-Trp-Aib (triangles) or without any addition (squares). Fluorescence values were measured after addition of 0.3 µM ThT to each sample. The results represent the mean of two independent measurements.

Figure 51A:
Figure 51B:
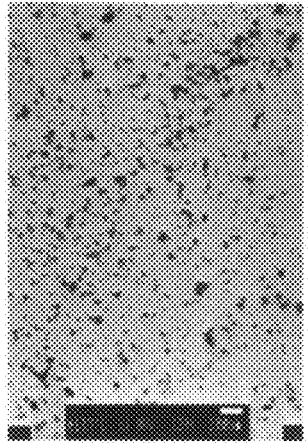
Figure 51C:
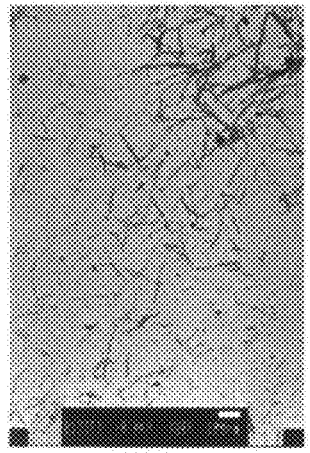

FIGS. 51a-c are photomicrographs depicting the inhibitory effect of D-Trp-Aib (SEQ ID NO: 145) on the fibrilization of Aβ as visualized by TEM. FIG. 51a shows Aβ alone. FIGS. 51b-c shows two different field of Aβ incubated in the presence of the inhibitor.

FIG. 52 is a gel image depicting the formation of a physical complex between D-Trp-Aib (SEQ ID NO: 145) and β-amyloid$_{1-42}$ intermediates, at an early stage of β-amyloid aggregation as evidenced by reduced electrophoretic migration. β-amyloid monomers (0.4 mM) were incubated alone (control) or with different concentrations of D-Trp-Aib: Lane 1, 1:2 molar ratio; lane 2, 1:10 molar ratio; lane 3, 1:20 molar ratio.

Figure 54:
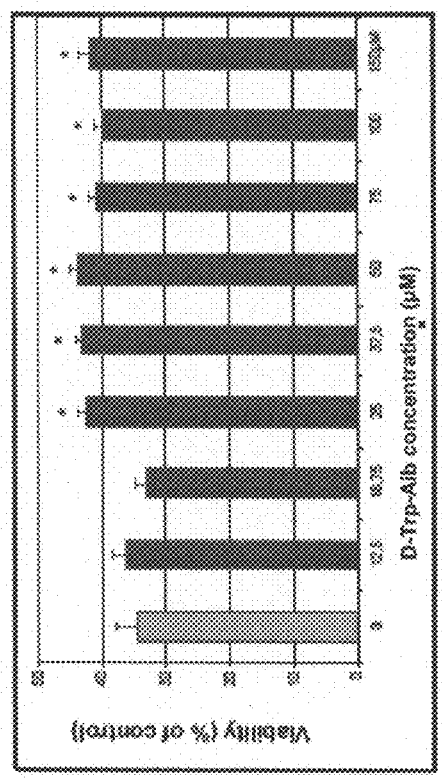

FIGS. 53a-b depict the ability of D-Trp-Aib (SEQ ID NO: 145) to block β-amyloid$_{1-42}$ globulomer formation. FIG. 53a is an immunoblot depicting a decrease of globulomer formation as a result of incubation with D-Trp-Aib. β-amyloid monomers were incubated (18 hours) with different concentrations of D-Trp-Aib as indicated, and immunoblotted with an anti β-amyloid monoclonal antibody (6E10). Lanes 1-3, control (β-amyloid 0.13 mM); lanes 4-6, β-amyloid and D-Trp-Aib, 1:5 molar ratio; lanes 7-9, β-amyloid and D-Trp-Aib, 1:10 molar ratio; lanes 10-12, β-amyloid and D-Trp-Aib, 1:20 molar ratio. FIG. 53b is a densitometer analysis bar graph of the western blot shown in FIG. 53a depicting dose dependent inhibition of globulomer formation FIG. 54 is a bar graph depicting the inhibition of f3-amyloid cytotoxicity to PC-12 cells by D-Trp-Aib (SEQ ID NO: 145). Mixture samples of concentrated $A\beta_{1-40}$ (25 µM) and a 5× concentration of indicated quantities of D-Trp-Aib, were incubated for 21 days. Thereafter PC-12 cells were incubated in the presence of the diluted above test samples. (end concentration 5 µM Aβ). At the end of a 24 hr incubation, an MIT reduction assay was effected. Viability was calculated by subtracting $A\beta_{1-40}$ samples absorbance from non-$A\beta_{1-40}$ controls containing the same D-Trp-Aib concentrations.

Figure 55:
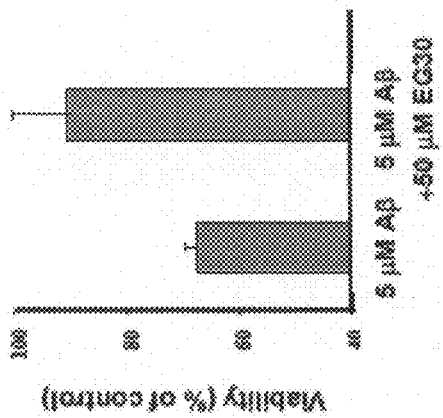

FIG. 55 is a bar graph depicting the inhibition of β-amyloid cytotoxicity to neuronal primary cells by D-Trp-Aib (SEQ ID NO: 145). Cells were incubated with Aβ (5 µM) and with or without D-Trp-Aib (50 µM), as indicated, and effects on β-amyloid$_{1-42}$ lesion were evaluated after 10 days by MIT. Results are shown as mean and s.e.m. of the data in percentages (unlesioned control is 100).

Figure 56A:
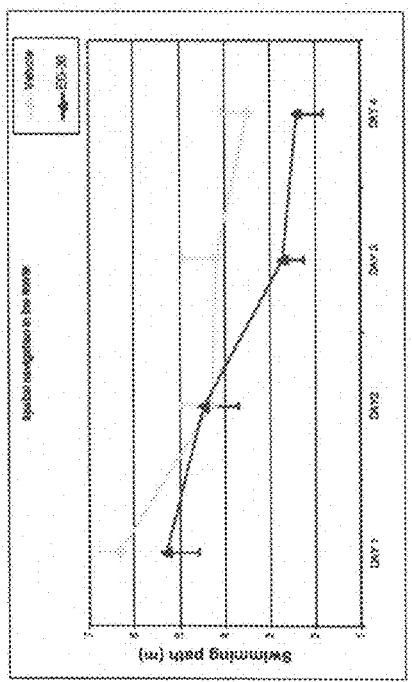
Figure 56B:
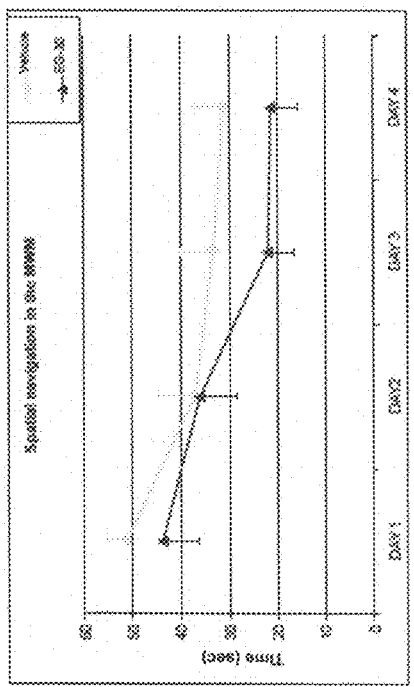

FIGS. 56a-b are graphs depicting D-Trp-Aib (SEQ ID NO: 145) had a beneficial effect on cognitive impairment in β-amyloid overproducing transgenic mice hAPP (751), as measured by the Morris water maze (MWM) test. FIG. 56a depicts a comparison of spatial navigation by means of swimming distance in the MWM test between mice treated (n=7) and not treated (n=6) with D-Trp-Aib (4 months treatment).

FIG. 56b depicts a comparison of spatial navigation by means of escape latency (in seconds) in the MWM test between mice treated with D-Trp-Aib and mice treated with vehicle (4 months treatment). Each point represents the mean+/−s.e.m. of 3 trials of all animals of a group/day, during 4 days. Competence in spatial navigation as depicted both in swimming distance and in time of escape is markedly improved in mice treated with the inhibitor. This is most notable in the last 2 days of the test (p<0.05 Mann-Whitney U-test), showing the retention of learning capabilities in treated mice, capabilities which were lost in amyloid producing non treated mice.

Figure 57A:
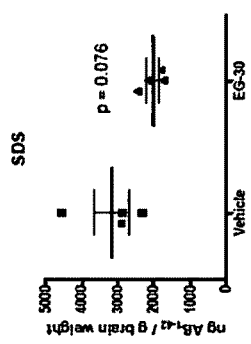
Figure 57B:
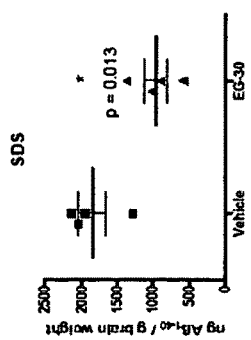
Figure 57C:
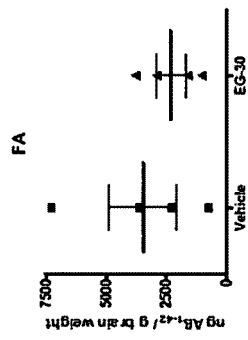
Figure 57D:
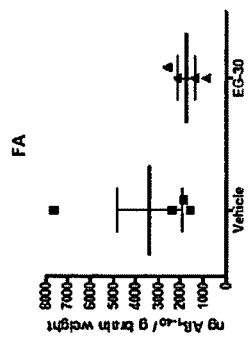

FIGS. 57a-d are graphs depicting the effect D-Trp-Aib (SEQ ID NO: 145) on β-amyloid concentrations in hAPP transgenic mice brain homogenates (ng Aβ per gr brain weight). FIGS. 57a-b depict the effect of D-Trp-Aib as compared to vehicle treated mice on levels of $A\beta_{1-40}$ (FIG. 57a) or $A\beta_{1-42}$ (FIG. 57b) in the SDS soluble fraction of brain homogenates. Levels of $hA\beta_{1-40}$ were significantly reduced in the SDS fraction by D-Trp-Aib treatment (FIG. 57a); the same was seen for $hA\beta_{1-42}$ albeit at a lower significance level. FIGS. 57c-d depict the effect of D-Trp-Aib as compared to vehicle treated mice on levels of insoluble (formic-acid treated) $A\beta_{1-40}$ (FIG. 57c) or $A\beta_{1-42}$ (FIG. 57d) in the Formic acid fraction of brain homogenates. Insoluble hAfβ in the FA fraction is not affected by D-Trp-Aib. Data are shown as single values and as mean±s.e.m.

Figure 58A:
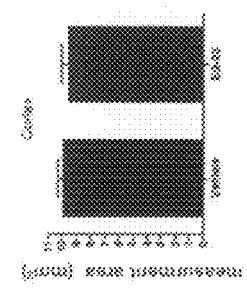
Figure 58B:
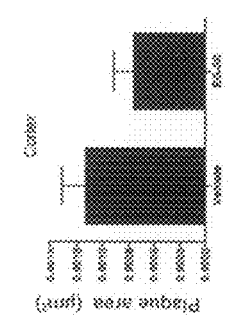
Figure 58C:
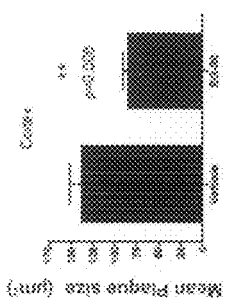
Figure 58D:
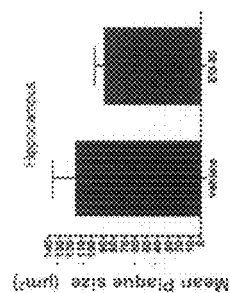
Figure 58E:
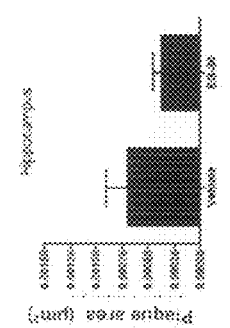
Figure 58F:
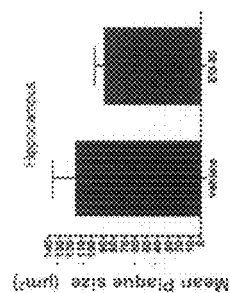

FIGS. 58a-f are bar graphs depicting the effect of D-Trp-Aib (SEQ ID NO: 145) on plaque load in hAPP transgenic mice brain cortex (FIGS. 58a-c) or Hippocampus (FIGS. 58d-f), as determined by ThioflavinS labeling. FIGS. 58a and d depict the effect of D-Trp-Aib as compared to vehicle treated mice on plaque region area. FIGS. 58b and e depict the effect of D-Trp-Aib as compared to vehicle treated mice on relative plaque area. FIGS. 58c and f depict the effect of D-Trp-Aib as compared to vehicle treated mice on mean plaque size. Data are presented as mean±s.e.m. Plaque area and mean size of n-sheet cores were reduced in the cortex and hippocampus of D-Trp-Aib treated mice. Reduction of mean plaque size was significant in the cortex of D-Trp-Aib treated mice.

FIGS. 59a-b are immunostaining micrographs depicting the effect of D-Trp-Aib treated (FIG. 59a. SEQ ID NO: 145), as compared to vehicle treated (FIG. 59b), hAPP transgenic mice on the ThioflavinS positive β-sheet cores of neuritic plaques in the cortex, as seen in an overlay of two consecutive slices, one immunostained with 6E10 and one stained with ThioflavinS, results of staining with ThioflavinS, 6E10 or both, as designated by arrows. A reduction of dense ThioS positive amyloid cores [stained in green (ThioflavinS) and yellow (6E10 and ThioflavinS)] is seen in D-Trp-Aib treated mice.

Figure 60A:
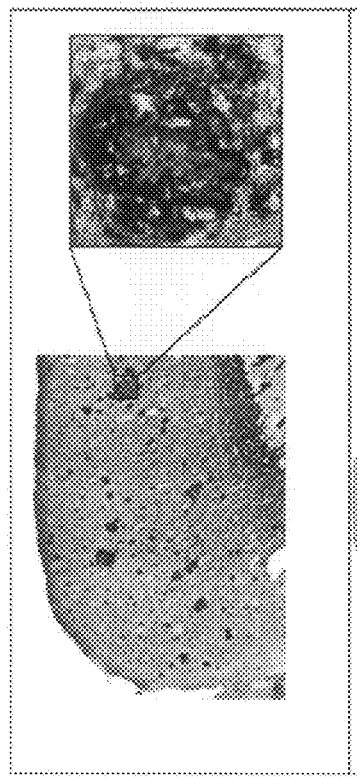
Figure 60B:
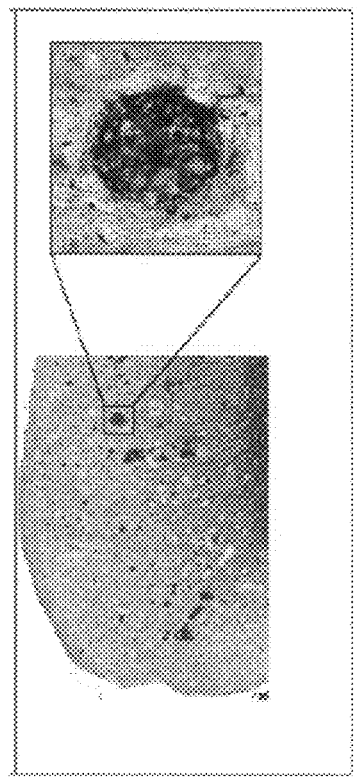

FIGS. 60a-b are micrographs showing Campbell-Switzer stain ED histological sections of hAPP transgenic mice frontal cortex with developing plaques, treated with vehicle (FIG. 60a) or D-Trp-Aib (FIG. 60b, SEQ ID NO: 145). The D-Trp-Aib treated cortex possesses fewer new, small-sized plaques, and mature plaques have sharply defined borders without the surrounding plaque seeds. Plaques in the vehicle-treated mice are framed by a number of additional newly built agglomerates, and more new plaques can be seen in the surrounding cortex area.

Figure 61:
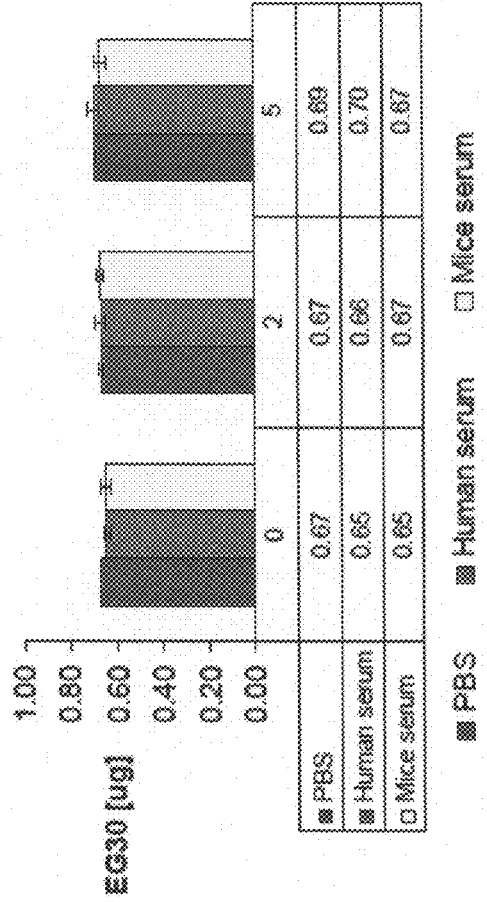

FIG. 61 is a bar graph depicting D-Trp-Aib (SEQ ID NO: 145) serum stability. D-Trp-Aib was incubated with mouse (depicted in white bars), human sera (depicted in purple bars) or PBS (depicted in magenta bars) at 37° C. and aliquots were analyzed at times 0, 2 and 5 hrs, by HPLC. Mean amounts of D-Trp-Aib (μg)±s.e.m. are presented, as calculated by an internal calibration curve.

Figures 62A, 62B:
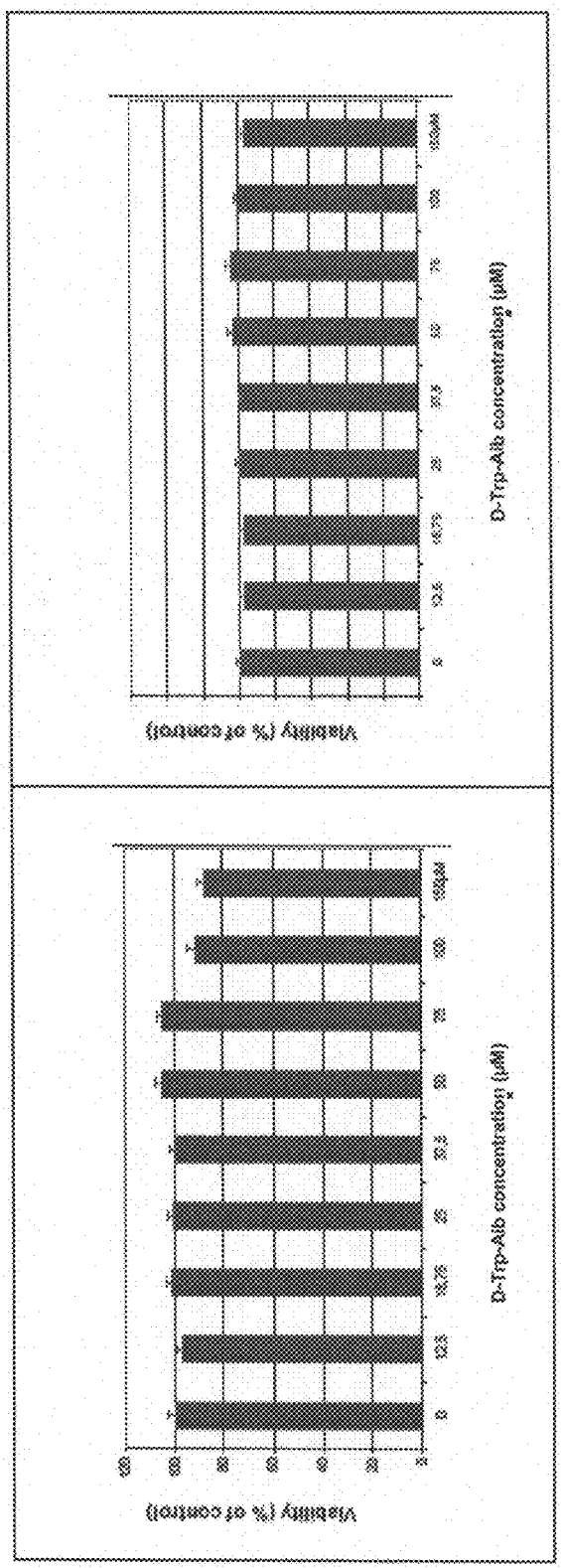
Figures 63A, 63B, 63C, 63D, 63E, 63F, 63G, 63H:
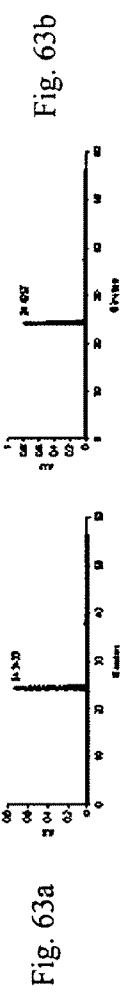

FIGS. 62a-b are bar graphs showing D-Trp-Aib (SEQ ID NO: 145) is noncytotoxic towards neuronal primary cell cultures. FIG. 62a depicts a neurotoxicity assay (5% assay) as determined by an MIT viability assay (ODs). FIG. 62b depicts a neurotoxicity assay (5% assay) as determined by an AM cacein assay. Results are presented as mean and s.e.m. of the data in percentages (control 0 μM is 100%).

FIGS. 63a-h are graphs showing D-Trp-Aib (SEQ ID NO: 145) temperature and pH stability, using analytical reversed phase high performance liquid chromatography (RP-HPLC). D-Trp-Aib was examined at different pH values: 3.1 (FIG. 63a), 7.2 (FIG. 63b), 10.7 (FIG. 63c), and at different temperatures 30° C. (FIG. 63d), 37° C. (FIG. 63e), 42° C. (FIG. 63g), 50° C. (FIG. 63g) 60° C. D-Trp-Aib remained stable at PH level range of 3.1-10.7 and at a temperature range of 30° C.-60° C.

Figure 64A:
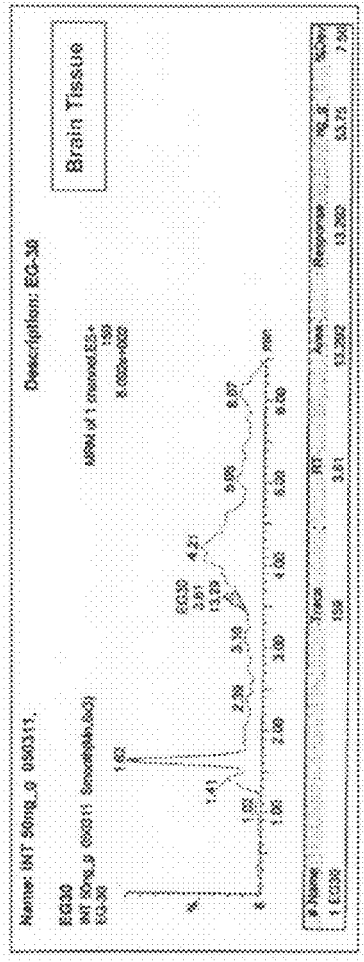
Figure 64B:
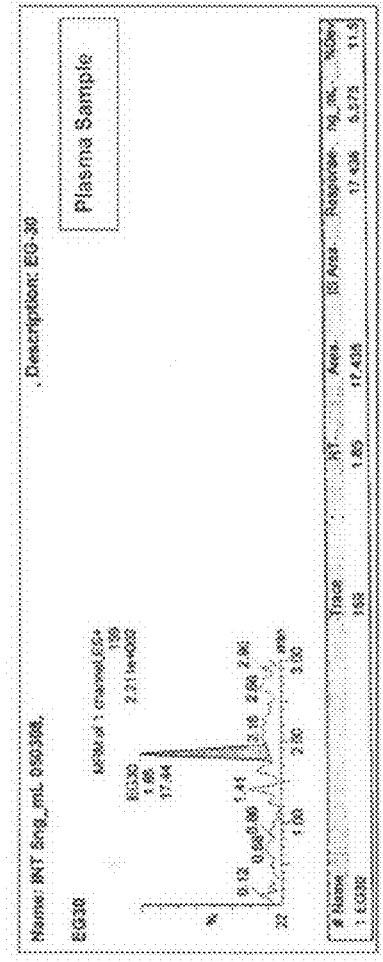

FIGS. 64a-b are graphs showing LC-MSIMS bioanalysis of brain tissue (FIG. 64a) and plasma samples (FIG. 64b) spiked with D-Trp-Aib (SEQ ID NO: 145). The amount of D-Trp-Aib is calculated from the area as identified by the mass-spectral analysis.

DESCRIPTION OF THE PREFERRED EMBODIMENTS

The present invention is of novel peptides, antibodies directed thereagainst, compositions including same and methods of utilizing each for diagnosing or treating amyloid associated diseases such as type II Diabetes mellitus.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Numerous therapeutic approaches for prevention of amyloid fibril formation or disaggregation of amyloid material have been described in the prior art. However, current therapeutic approaches are limited by cytotoxicity, non-specificity and delivery barriers.

While reducing the present invention to practice and while searching for a novel therapeutic modality to amyloid associated diseases, such as Type II diabetes mellitus, the present inventor has identified a sequence characteristic of amyloid forming peptides, which directs fibril formation. This finding suggests that ordered amyloidogenesis involves a specific pattern of molecular interactions rather than the previously described mechanism involving non-specific hydrophobic interactions [Petkova (2002) Proc. Natl. Acad. Sci. USA 99:16742-16747].

As is further illustrated hereinbelow and in the Examples section which follows, the present inventor attributed a pivotal role for aromatic residues in amyloid formation. The involvement of aromatic residues in the process of amyloid formation is in-line with the well-established role of π-stacking interactions in molecular recognition and self-assembly [Gillard et al (1997) Chem. Eur. J. 3: 1933-40; Claessens and Stoddart, (1997) J. Phys. Org. Chem. 10: 254-72; Shetty et al (1996) J. Am. Chem. Soc. 118: 1019-27; McGuaghey et al (1998) π-stacking interactions: Alive and well in proteins. J. Biol. Chem. 273, 15458-15463; Sun and Bernstein (1996) J. Phys. Chem. 100: 13348-66]. π-stacking interactions are non-bonded interactions which are formed between planar aromatic rings. The steric constrains associated with the formation of those ordered stacking structures have a fundamental role in self-assembly processes that lead to the formation of supramolecular structures. Such π-stacking interactions, which are probably entropy driven, play a central role in many biological processes such as stabilization of the double-helix structure of DNA, core-packing and stabilization of the tertiary structure of proteins, host-guest interactions, and porphyrin aggregation in solution [for further review on the possible role of π-stacking interaction in the self-assembly of amyloid fibrils see Gazit (2002) FASEB J. 16:77-83].

The present inventor demonstrated the ability of short aromatic peptide sequences, as short as di-peptides (see Example 45-47), to mediate molecular recognition, enabling for the first time, to generate highly efficient diagnostic, prophylactic and therapeutic peptides which can be utilized to treat or diagnose diseases characterized by amyloid plaque formation.

One such peptide, EG30 (SEQ ID NO: 145) showed an outstanding in-vitro activity as anti amyloidogenic peptide, pharmacologic properties and therapeutic efficacy as illustrated below and in the Examples section which follows. As is shown in Examples 47-51, D-Trp-Aib (also termed EG30; SEQ ID NO: 145), was found to hold all the desired chemical and structural properties of an amyloid aggregation inhibitor (i.e., it is a charged, hydrophobic, bulky, β-breaking, non-cleavable stable isomer, which inhibits amyloid aggregation). In vitro experimental results, presented in Examples 47-49, show an outstanding inhibiting effect of D-Trp-Aib on amyloid fibrilization both independently and in cell cultures (cell lines and primary cultures). In vivo results in β-amyloid overproducing transgenic mice, an animal model for Alzheimer's disease, shown in Example 50, illustrate a marked reduction in β-amyloid concentration and plaque formation in D-Trp-Aib treated mice, which had a substantial unprecedented therapeutic effect on the decline of mice cognitive abilities. The pharmaceutical properties of D-Trp-Aib presented in the results given in Example 51 show absolute pharmacokinetic characteristics D-Trp-Aib (in terms of bioavailability, transport through blood brain barrier, stability before and after administration, toxicity and therapeutic influence) that render this molecule to be not only a potential drug lead, but to have the potential to be administered independently as the drug itself.

Thus, according to one aspect of the present invention there is provided a peptide which includes the amino acid sequence X-Y or Y-X, wherein X is an aromatic amino acid and Y is any amino acid other than glycine. Examples of peptides that include this sequence are set forth in SEQ ID Nos. 4, 12-19, 27-45, 112-123, 125 and 127. As is shown by the results presented in Examples 36-39 of the Examples section which follows, the present inventor have uncovered that contrary to the teachings of the prior art, it is aromaticity rather than hydrophobicity which dictates amyloid self-assembly. Thus, the aromatic amino acid of the peptides of the present invention is pivotal to the formation of amyloid fibrils.

The aromatic amino acid can be any naturally occurring or synthetic aromatic residue including, but not limited to, phenylalanine, tyrosine, tryptophan, phenylglycine, or modificants, precursors or functional aromatic portions thereof. Examples of aromatic residues which can form a part of the peptides of present invention are provided in Table 2 below.

As is demonstrated by the results provided in the Examples section which follows, the present invention facilitates the design of peptides exhibiting varying degrees of self-aggregation kinetics and aggregate structure.

As used herein, the phrase "self-aggregation" refers to the capability of a peptide to form aggregates (e.g. fibrils) in an aqueous solution. The ability of a peptide to self-aggregate and the kinetics and type of such self-aggregation determines a use for the peptide in treating or diagnosing amyloid diseases.

Since aggregation kinetics and aggregate structures are largely determined by the specific residue composition and possibly the length of the peptides generated (see FIG. 1), the present invention encompasses both longer peptides (e.g., 10-50 amino acids), which include the sequences set forth in SEQ ID NOs: 4. 12-19, 27-45, 112-123, 125, 127, 128-147 or 148, or preferably shorter peptides (e.g., 2-15 amino acids, preferably at least 2, at least 3, at least 4, at least 5, at least 6, at least 8, at least-10, say 12 amino acids, preferably no more than 15 amino acids) including any of these sequences.

In order to enhance the rate of amyloid formation, the peptides of the present invention preferably include at least one polar and uncharged amino acid including but not limited to serine, threonine, asparagine, glutamine or natural or synthetic derivatives thereof (see Table 2).

According to one embodiment of this aspect of the present invention, amino acid residue Y is the polar and uncharged amino acid.

According to another embodiment of this aspect of the present invention, the peptide includes at least 3 amino acids, the X-Y/Y-X amino acid sequence described hereinabove and an additional polar and uncharged amino acid positioned either upstream (N-Terminal end) or downstream (C-Terminal end) of the X-Y/Y-X sequence.

The peptides of the present invention, can be at least 3 amino acid in length and may include at least one pair of positively charged (e.g., lysine and arginine) and negatively charged (e.g., aspartic acid and glutamic acid) amino acids (e.g., SEQ ID NOs. 27-29). Such amino acid composition may be preferable, since as shown in Examples 21 of the Examples section, it is likely that electrostatic interactions between opposing charges may direct the formation of ordered antiparallel structure.

Yet additionally, the peptide of the present invention can be 4 amino acids in length and include two serine residues at the C-terminal end of the X-Y/Y-X sequence.

Still additionally, the peptide of the present invention can be at least 3 amino acids in length and include a thiolated amino acid residue (i.e., including a sulfur ion), preferably at an N-terminal end thereof (e.g., SEQ ID NOs: 149 and 150, D-Cys-D-Trp-Aib and L-Cys-D-Trp-Aib, respectively as well as their acytelated and amidated forms). Such a peptide configuration is highly valuable since it provides reducing properties to the peptide and as such can serve both as a reducing agent and as an antioxidant both may be critical for neuroprotection [Offen et al. (2004) J Neurochem. 89:1241-51]; and as an amyloid inhibitor. Examples of thiolated amino acids include, but are not limited to, the naturally occurring amino acids cysteine and methionine and synthetic amino acids such as Tyr ($SO_3H$).

Since the present inventor has identified the sequence characteristics governing fibril formation, the teachings of the present invention also enable design of peptides which would not aggregate into fibrils and be capable of either preventing or reducing fibril formation or disrupting preformed fibrils and thus can be used as a therapeutic agents.

For example, a peptide encompassed by SEQ ID NO: 9, 10, 11, 17, 19, 25 or 30 can be utilized for therapy since as is shown in the Examples section which follows, such a peptide displays no aggregation (SEQ ID NO: 9) or slow aggregation kinetics as compared to the wild type peptide (SEQ ID NOs: 9 and 10). It is conceivable that since amyloid formation is a very slow process, these peptide sequences will completely inhibit or significantly delay amyloidosis under physiological conditions.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, Tic, naphtylalanine (Nal), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |

TABLE 2-continued

| Non-conventional amino acid | Code | Non-conventional amino acid | Code |
|---|---|---|---|
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 2-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

For therapeutic application, the peptides of the present invention preferably include at least one β-sheet breaker amino acid residue, which is positioned in the peptide sequence as described below. Peptides which include such β-sheet breaker amino acids retain recognition of amyloid polypeptides but prevent aggregation thereof (see Examples 40-45 of the Examples section which follows). According to one preferred embodiment of this aspect of the present invention, the β-sheet breaker amino acid is a naturally occurring amino acid such as proline (e.g., SEQ ID NOs. 45, 112, 119, 120, 122, 123, 128, 130, 134, 138, 139, 140, 141, 143, 144, 146, 147 and 148, see background section) which is characterized by a limited phi angle of about −60 to +25 rather than the typical beta sheet phi angle of about −120 to −140 degrees, thereby disrupting the beta sheet structure of the amyloid fibril. Other β-sheet breaker amino acid residues include, but are not limited to aspartic acid, glutamic acid, glycine, lysine and serine (according to Chou and Fasman (1978) Annu. Rev. Biochem. 47, 258).

According to another preferred embodiment of this aspect of the present invention, the β-sheet breaker amino acid residue is a synthetic amino acid such as a Cα-methylated amino acid, which conformational constrains are restricted [Balaram, (1999) J. Pept. Res. 54, 195-199]. Unlike natural amino acids, Cα-methylated amino acids have a hydrogen atom attached to the $C_\alpha$, which affects widely their sterical properties regarding the φ and ψ angels of the amide bond. Thus, while alanine has a wide range of allowed φ and ψ conformations, α-aminoisobutyric acid (Aib, see Table 2, above) has limited φ and ψ conformations. Hence, peptides of the present invention which are substituted with at least one Aib residue are capable of binding amyloid polypeptides but prevent aggregation thereof (see Examples 40-44). Such peptides are set forth in SEQ ID NOs: 113, 114, 117, 118, 121, 135, 136, 137, 143, 145, 149, 129 and 131.

The β-sheet breaker amino acid of this aspect of the present invention can be located at position Y of the X-Y/Y-X amino acid sequence of the peptide (see for Example SEQ ID NOs: 123, 143, 144, 145, 146, 147, 148). Alternatively, the peptides of this aspect of the present invention can be at least 3 amino acids and include the breaker amino acid in any position other than the X-Y/Y-X amino acid sequence (see for example SEQ ID NO: 117).

The β-sheet breaker amino acid may be positioned upstream of the aromatic residue (see SEQ ID NO: 122) or downstream thereto (see SEQ ID NO: 123).

According to one preferred embodiment of this aspect of the present invention the peptide is three amino acids in length, wherein Y is an aromatic amino acid and an amino acid residue attached to the amino acid sequence X-Y or Y-X is a β-sheet breaker amino acid, which is preferably attached at the C-terminus of the peptide (e.g., SEQ ID NOs: 135 and 140).

According to another preferred embodiment of this aspect of the present invention the peptide is two amino acids in length and Y is a β-sheet breaker amino acid (e.g., SEQ ID NOs: 121, 143-148).

According to a most preferred embodiment of this aspect of the present invention the peptide is a dipeptide having the following general formula:

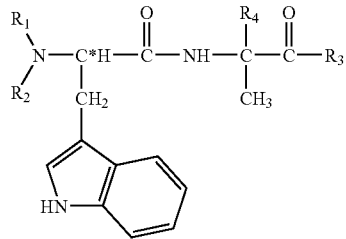

wherein:

C* is a chiral carbon having a D configuration (also referred to in the art as R-configuration).

$R_1$ and $R_2$ are each independently selected from the group consisting of hydrogen, alkyl, cycloalkyl, aryl, carboxy, thiocarboxy, C-carboxylate and C-thiocarboxylate;

$R_3$ is selected from the group consisting of hydroxy, alkoxy, aryloxy, thiohydroxy, thioalkoxy, thioaryloxy, halo and amine; and $R_4$ is alkyl.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, halo, hydroxy, cyano, nitro and amino.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, halo, hydroxy, cyano, nitro and amino.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, cycloalkyl, halo, hydroxy, alkoxy, thiohydroxy, thioalkoxy, cyano, nitro and amino.

A "hydroxy" group refers to an —OH group.

An "alkoxy" group refers to both an —O-alkyl and an —O-cycloalkyl group, as defined herein.

An "aryloxy" group refers to an —O-aryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to an —S-aryl group, as defined herein.

A "carboxy" group refers to a —C(=O)—R' group, where R' is hydrogen, halo, alkyl, cycloalkyl or aryl, as defined herein.

A "thiocarboxy" group refers to a —C(=S)—R' group, where R' is as defined herein for R'.

A "C-carboxylate" group refers to a —C(=O)—O—R' groups, where R' is as defined herein.

A "C-thiocarboxylate" group refers to a —C(=S)—O—R' groups, where R' is as defined herein.

A "halo" group refers to fluorine, chlorine, bromine or iodine.

An "amine" group refers to an —NR'R" group where R' is as defined herein and R" is as defined for R'.

A "nitro" group refers to an —NO$_2$ group.

A "cyano" group refers to a —C≡N group.

Preferably, R$_4$ is methyl, such that the compound above is D-tryptophane-alpha-aminobutyric acid (also referred to herein as D-Trp-Aib or D-tryptophane-alpha-methyl-alanine), or a derivative thereof.

It will be appreciated that unmodified di-peptides, peptides of L-configuration, peptides which are of a reversed configuration (i.e., C-to-N sequence of tryptophane (D/L) and alpha-methyl alanine), or alternatively, macromolecules (e.g., peptides, immobilized peptides) which encompass the above-described peptide sequence, are known (see e.g., WO 02/094857, WO 02/094857, EP Pat. No. 966,975, U.S. Pat. Nos. 6,255,286, 6,251,625, 6,162,828 and 5,304,470). However, such molecules are chemically and biologically different than the above described peptide, which unique activity is strictly dependent on its structure.

The peptides of the present invention are preferably utilized in a linear form, although it will be appreciated that in cases where cyclization does not severely interfere with peptide characteristics, cyclic forms of the peptide can also be utilized.

Cyclic peptides can either be synthesized in a cyclic form or configured so as to assume a cyclic form under desired conditions (e.g., physiological conditions).

For example, a peptide according to the teachings of the present invention can include at least two cysteine residues flanking the core peptide sequence. In this case, cyclization can be generated via formation of S—S bonds between the two Cys residues. Side-chain to side chain cyclization can also be generated via formation of an interaction bond of the formula —(—CH2-)n-S—CH2-C—, wherein n=1 or 2, which is possible, for example, through incorporation of Cys or homocys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH2)n-COOH)—C(R)H—COOH or H—N((CH2)n-COOH)—C(R)H—NH2, wherein n=1-4, and further wherein R is any natural or non-natural side chain of an amino acid.

Thus, the present invention provides conclusive data as to the identity of the structural determinant of amyloid peptides, which directs fibril assembly.

As such, the present invention enables design of a range of peptide sequences, which can be utilized for prevention/treatment or diagnosis of amyloidosis.

As is described in Examples 6-35, the present inventor identified the consensus aromatic sequence of the present invention (SEQ ID NO: 7) in numerous amyloid related proteins, thereby conclusively showing that the present invention enables accurate identification of amyloidogenic fragments in essentially all amyloidogenic proteins.

Furthermore, the fact that small aromatic molecules, such as Ro 47-1816/001 [Kuner et al. (2000) J. Biol. Chem. 275: 1673-8, see FIG. 2*a*] and 3-p-toluoyl-2-[4'-(3-diethylamino-propoxy)-phnyl]-benzofuran [Twyman (1999) Tetrahedron Letters 40:9383-9384] have been demonstrated effective in inhibiting the polymerization of the beta polypeptide of Alzheimer's disease [Findeis et al. (2000) Biochem. Biophys. Acta 1503:76-84], while amyloid specific dyes such as Congo-Red (FIG. 2*b*) and Thioflavin T (FIG. 2*c*), which contain aromatic elements are generic amyloid formation inhibitors, substantiate the recognition motif of the present invention as sufficient for amyloid self-assembly.

The availability of the peptides of the present invention allows for the generation of antibodies directed thereagainst, which may be used to dissociate or prevent the formation of amyloid plaques (U.S. Pat. No. 5,688,561).

The term "antibody" refers to intact antibody molecules as well as functional fragments thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (v) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

For human applications, the antibodies of the present invention are preferably humanized. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boemer et al. are also available for the preparation of human monoclonal antibodies (Cole et al., Monoclonal Antibodies and Cancer Therapy, Alan R. Liss, p. 77 (1985) and Boemer et al., J. Immunol., 147(1):86-95 (1991)].

Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

As is mentioned hereinabove, one specific use for the peptides of the present invention is prevention or treatment of diseases associated with amyloid plaque formation.

Thus, according to yet another aspect of the present invention, there is provided a method of treating an amyloid-associated disease in an individual. Preferred individual subjects according to the present invention are mammals such as canines, felines, ovines, porcines, equines, bovines, humans and the like.

The term "treating" refers to reducing or preventing amyloid plaque formation, or substantially decreasing plaque occurrence in the affected tissue. The phrase "amyloid plaque" refers to fibrillar amyloid as well as aggregated but not fibrillar amyloid, hereinafter "protofibrillar amyloid", which may be pathogenic as well. For example, an aggregated but not necessarily fibrillar form of IAPP was found to be toxic in culture. As shown by Anaguiano and co-workers [(2002) Biochemistry 41:11338-43] protofibrillar IAPP, like protofibrillar α-synucelin, which is implicated in Parkinson's disease pathogenesis, permeabilized synthetic vesicles by a pore-like mechanism. The formation of the IAPP amyloid pore was temporally correlated to the formation of early IAPP oligomers and disappearance thereof to the appearance of amyloid fibrils. These results suggest that protofibrillar IAPP may be critical to type II diabetes mellitus as other protofibrillar proteins are critical to the development of Alzheimer's and Parkinson's diseases.

Amyloid-associated diseases treated according to the present invention include, but are not limited to, type II diabetes mellitus, Alzheimer's disease (AD), early onset Alzheimer's disease, late onset Alzheimer's disease, presymptomatic Alzheimer's disease, Parkinson's disease, SAA amyloidosis, hereditary Icelandic syndrome, multiple myeloma, medullary carcinoma, aortic medical amyloid, Insulin injection amyloidosis, prion-systematic amyloidosis, chronic inflammation amyloidosis, Huntington's disease, senile systemic amyloidosis, pituitary gland amyloidosis, Hereditary renal amyloidosis, familial British dementia, Finnish hereditary amyloidosis, familial non-neuropathic amyloidosis [Gazit (2002) Curr. Med. Chem. 9:1667-1675] and prion diseases including scrapie of sheep and goats and bovine spongiform encephalopathy (BSE) of cattle [Wilesmith and Wells (1991) Curr Top Microbiol Immunol 172: 21-38] and human prion diseases including (i) Kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

The method includes providing to the individual a therapeutically effective amount of the peptide of the present invention. The peptide can be provided using any one of a variety of delivery methods. Delivery methods and suitable formulations are described hereinbelow with respect to pharmaceutical compositions.

It will be appreciated that when utilized for treatment of amyloid diseases, the peptide of the present invention includes an amino acid sequence suitable for preventing fibril formation, reducing fibril formation, or disaggregating formed aggregates by competitive destabilization of the preformed aggregate. For example, SEQ ID NOs: 45, 112-123, 125, 127, 128-149 and 150 can be utilized for treatment of amyloid diseases, particularly type II diabetes mellitus since as shown in Example 35 and in Example 45 of the Examples section which follows, such sequences interfere with IAPP self-assembly as demonstrated by the decreased ability of the amyloidogenic peptide to bind Thioflavin T in the presence of inhibitory peptides.

Alternatively, the peptides set forth in SEQ ID NOs: 10 or 11 can be used as potent inhibitors of type II diabetes since as shown in the Examples section which follows, substitution of either leucine or isoleucine in the peptide elicits very slow kinetics of aggregation. Since amyloid formation in vivo is a very slow process, it is conceivable that under physiological conditions no fibrilization will occur upon the substitution of isoleucine or leucine to alanine in the context of the full length IAPP.

Alternatively, self-aggregating peptides such as those set forth in SEQ ID NOs. 17, 19 and 28-30, can be used as potent inhibitors of amyloid fibrilization, since such peptides can form heteromolecular complexes which are not as ordered as the homomolecular assemblies formed by amyloid fragments.

It will be appreciated that since one of the main obstacles in using short peptide fragments in therapy is their proteolytic degradation by stereospecific cellular proteases, the peptides of the present invention are preferably synthesized from D-isomers of natural amino acids [i.e., inverso peptide analogues, Tjernberg (1997) J. Biol. Chem. 272:12601-5, Gazit (2002) Curr. Med. Chem. 9:1667-1675].

Additionally, the peptides of the present invention include retro, inverso and retro-inverso analogues thereof. It will be appreciated that complete or extended partial retro-inverso analogues of hormones have generally been found to retain or enhance biological activity. Retro-inversion has also found application in the area of rational design of enzyme inhibitors (see U.S. Pat. No. 6,261,569).

As used herein a "retro peptide" refers to peptides which are made up of L-amino acid residues which are assembled in opposite direction to the native peptide sequence.

Retro-inverso modification of naturally occurring polypeptides involves the synthetic assembly of amino acids with α-carbon stereochemistry opposite to that of the corresponding L-amino acids, i.e., D- or D-allo-amino acids in inverse order to the native peptide sequence. A rerto inverso analogue, thus, has reversed termini and reversed direction of peptide bonds, while essentially maintaining the topology of the side chains as in the native peptide sequence.

Additionally, since one of the main issues in amyloid fibril formation is the transition of the amyloid polypeptide from the native form to stacked β-strand structure, inhibitory peptides preferably include N-methylated amino acids which constrain peptide-backbone due to steric effects [Kapumiotu (2002) 315:339-350]. For example, aminoisobutyric acid (Aib or methyl alanine) is known to stabilize an α-helical structure in short natural peptides. Furthermore, the N-methylation also affects the intermolecular NH to CO H-bonding ability, thus suppressing the formation of multiplayer β-strands, which are stabilized by H-bonding interactions.

It will be further appreciated that addition of organic groups such as a cholyl groups to the N-terminal or C-terminal of the peptides of the present invention is preferred since it was shown to improve potency and bioavailability (e.g., crossing the blood brain barrier in the case of neurodegenerative diseases) of therapeutic peptides [Findeis (1999) Biochemistry 38:6791-6800]. Furthermore, introducing a charged amino acid to the recognition motif, may result in electrostatic repulsion which inhibits further growth of the amyloid fibrils [Lowe (2001) J. Mol. Biol. 40:7882-7889].

As mentioned hereinabove, the antibodies of the present invention may also be used to treat amyloid-associated diseases.

The peptides and/or antibodies of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide or antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the peptides or antibodies of the present invention can also be expressed from a nucleic acid construct administered to the individual employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the peptides or antibodies of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Because of the self-aggregating nature of the peptides of the present invention it is conceivable that such peptides can also be used as potent detectors of amyloid fibrils/plaques in biological samples. This is of a special significance to amyloid-associated diseases such as Alzheimer's disease wherein unequivocal diagnosis can only be made after postmortem examination of brain tissues for the hallmark neurofibrillary tangles (NFT) and neuritic plaques.

Thus, according to yet another aspect of the present invention there is provided a method of detecting a presence or an absence of an amyloid fibril in a biological sample.

The method is effected by incubating the biological sample with a peptide of the present invention capable of co-aggregating with the amyloid fibril and detecting the peptide, to thereby detect the presence or the absence of amyloid fibril in the biological sample. A variety of peptide reagents, which are capable of recognizing conformational ensembles are known in the art some of which are reviewed in Bursavich (2002) J. Med. Chem. 45(3): 541-58 and in Baltzer Chem Rev. 101(10):3153-63.

The biological sample utilized for detection can be any body sample such as blood (serum or plasma), sputum, ascites fluids, pleural effusions, urine, biopsy specimens, isolated cells and/or cell membrane preparation. Methods of obtaining tissue biopsies and body fluids from mammals are well known in the art.

The peptide of the present invention is contacted with the biological sample under conditions suitable for aggregate formation (i.e., buffer, temperature, incubation time etc.); suitable conditions are described in Example 2 of the Examples section. Measures are taken not to allow pre-aggregation of peptides prior to incubation with the biological sample. To this end freshly prepared peptide stocks are preferably used.

Protein complexes within a biological sample can be detected via any one of several methods known in the art, which methods can employ biochemical and/or optical detection schemes.

To facilitate complex detection, the peptides of the present invention are highlighted preferably by a tag or an antibody. It will be appreciated that highlighting can be effected prior to, concomitant with or following aggregate formation, depending on the highlighting method. As used herein the term "tag" refers to a molecule, which exhibits a quantifiable activity or characteristic. A tag can be a fluorescent molecule including chemical fluorescers such as fluorescein or polypeptide fluorescers such as the green fluorescent protein (GFP) or related proteins (wwwdotclontechdotcom). In such case, the tag can be quantified via its fluorescence, which is generated upon the application of a suitable excitatory light. Alternatively, a tag can be an epitope tag, a fairly unique polypeptide sequence to which a specific antibody can bind without substantially cross reacting with other cellular epitopes. Such epitope tags include a Myc tag, a Flag tag, a His tag, a leucine tag, an IgG tag, a streptavidin tag and the like.

Alternatively, aggregate detection can be effected by the antibodies of the present invention.

Thus, this aspect of the present invention provides a method of assaying or screening biological samples, such as body tissue or fluid suspected of including an amyloid fibril.

It will be appreciated that such a detection method can also be utilized in an assay for uncovering potential drugs useful in prevention or disaggregation of amyloid deposits. For example, the present invention may be used for high throughput screening of test compounds. Typically, the co-aggregating peptides of the present invention are radiolabeled, to reduce assay volume. A competition assay is then effected by monitoring displacement of the label by a test compound [Han (1996) J. Am. Chem. Soc. 118:4506-7 and Esler (1996) Chem. 271:8545-8].

It will be appreciated that the peptides of the present invention may also be used as potent detectors of amyloid deposits in-vivo. A designed peptide capable of binding amyloid deposits, labeled non-radioactively or with a radio-isotope, as is well known in the art can be administered to an individual to diagnose the onset or presence of amyloid-related disease, discussed hereinabove. The binding of such a labeled peptide after administration to amyloid or amyloid-like deposits can be detected by in vivo imaging techniques known in the art.

The peptides of the present invention can be included in a diagnostic or therapeutic kit. For example, peptide sets of specific disease related proteins or antibodies directed thereagainst can be packaged in a one or more containers with appropriate buffers and preservatives and used for diagnosis or for directing therapeutic treatment.

Thus, the peptides can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added.

The peptides of such kits can also be attached to a solid support, such as beads, array substrate (e.g., chips) and the like and used for diagnostic purposes.

Peptides included in kits or immobilized to substrates may be conjugated to a detectable label such as described hereinabove.

The kit can also include instructions for determining if the tested subject is suffering from, or is at risk of developing, a condition, disorder, or disease associated with amyloid polypeptide of interest.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Alanine Scan of the hIAPP Basic Amylodogenic Unit

Rational and Peptide Synthesis

Pancreatic amyloid is found in more than 95% of type II diabetes patients. Pancreatic amyloid is formed by the aggregation of a 37 amino acid long islet amyloid polypeptide (IAPP, GenBank Accession No. gi:4557655), the cytotoxicity thereof being directly associated with the development of the disease. IAPP amyloid formation follows a nucleation-dependent polymerization process, which proceeds through conformational transition of soluble IAPP into aggregated β-sheets. Recently it has been shown that a hexapeptide (22-27) (NFGAIL, SEQ ID NO: 111) of IAPP, also termed as the "basic amyloidogenic unit" is sufficient for the formation of β-sheet-containing amyloid fibrils [Konstantinos et al. (2000) J. Mol. Biol. 295:1055-1071].

To gain further insight into the specific role of the residues that compose "the "basic amyloidogenic unit", a systematic alanine scan was performed. Amino-acids were replaced with alanine in order to specifically change the molecular interface of the peptides, without significantly changing their hydrophobicity or tendency to form β-sheet structures. Alanine-scan was preformed in the context of the block that is unique to human IAPP (FIG. 3a). This block includes two serine residues that follow the NFGAIL motif in the full-length polypeptide. These eight amino-acid peptide sequences were used since the shorter peptides are hydrophobic and as s such less soluble. FIG. 3b shows a schematic representation of the chemical structure of the wild-type peptide while FIG. 3c indicates the amino-acid substitutions in the different mutant peptides that were generated.

Methods and Reagents—Peptide synthesis was performed by PeptidoGenic Research & Co. Inc (Livermore, Calif. USA). The sequence identity of the peptides was confirmed by ion spray mass-spectrometry using a Perkin Elmer Sciex API I spectrometer. The purity of the peptides was confirmed by reverse phase high-pressure liquid chromatography (RP-HPLC) on a $C_{18}$ column, using a linear gradient of 10 to 70% acetonitrile in water and 0.1% trifluoroacetic acid (TFA).

Example 2

Kinetics of Aggregation of L4PP Peptide Fragment and Mutant Derivatives as Monitored by Turbidity Measurements To study self-assembly of the IAPP peptide derived fragments, aggregation and insolubilization kinetics were monitored using turbidity measurements at 405 nm.

Kinetic aggregation assay—Fresh peptide stock solutions were prepared by dissolving lyophilized form of the peptides in DMSO, a disaggregating solvent, at a concentration of 100 mM. To avoid any pre-aggregation, fresh stock solutions were prepared prior to each and every experiment. Peptide stock solutions were diluted into assay buffer and plated in 96-well plates as follows: 2 µl of peptides stock solutions were added to 98 µl of 10 mM Tris pH 7.2, resulting in a 2 mM final concentration of the peptide in the presence of 2% DMSO. Turbidity data was measured at 405 nm. A buffer solution including 2% DMSO was used as a blank. Turbidity was measured at room temperature over several time points.

Results—As shown in FIG. 4a, wild-type peptide fragment (SEQ ID NO: 1) showed an aggregation kinetic profile that was very similar to those previously reported for non-seeded hIAPP hexapeptide [Tenidis et al. (2000) J. Mol. Biol. 295: 1055-71]. Such a profile is strongly indicative of a nucleation-dependent polymerization mechanism [Jarrett and Lansbury (1992) Biochemistry 31:6865-70]. Following a lag-time of 20 minutes, wild type peptide self-assembled into insoluble fibrils. Peptide G3A (SEQ ID NO: 4) showed essentially the same profile as that of wild type peptide. The N1A peptide (SEQ ID NO: 2) mediated higher kinetics of aggregation, albeit with different kinetic profile as compared to that of wild-type peptide. Interestingly, the aggregation of N1A seemed to be less nucleation-dependent. Substitution of the isoleucine or leucine to alanine (peptides I5A, SEQ ID NO: 5 and L6A, SEQ ID NO: 6 respectively) reduced the kinetics of aggregation but did not abolish it completely. Substitution of the phenylalanine residue to alanine (peptide F2A, SEQ ID NO:3) led to a total loss of peptide ability to aggregate. The F2A peptide was completely soluble in the aqueous assay buffer.

Altogether, kinetic aggregation studies of the amyloidogenic fragments suggested a major role to the phenylalanine residue in the process of amyloid formation by the IAPP active fragment.

Example 3

Measurement of Aggregate Mean Particle Size

While the turbidity assay provided an important estimate regarding the aggregation potential and kinetics of the various peptides, it did not provide information about the size of the actual aggregates formed. It will be appreciated that although the apparent hydrodynamic diameter of amyloid structures varies due to irregularity of the amyloid structure, it may still provide a clear indication about the order of magnitude of the structure formed and present a quantitative criterion for comparing the structures formed by the various peptides.

Therefore, the average size of the aggregates, formed by the various peptides, was determined using dynamic light scattering (DLS) experiments.

Method—Freshly prepared peptide stock solutions at a concentration of 10 mM were diluted in 10 mM Tris buffer pH 7.2 and further filtrated through a 0.2 μm filter to a final concentration of 100 μM peptide and 1% DMSO. Particle size measurement was conducted with a laser-powered ALV-NIBS/HPPS non-invasive backscattering instrument. Autocorrelation data was fitted using the ALV-NIBS/HPPS software to derive average apparent hydrodynamic diameters.

Results—The average apparent hydrodynamic diameters of the structures that were formed by the various peptides are presented in FIG. 5.

Altogether, the apparent hydrodynamic diameter of the structures formed by the various peptides seemed to be consistent with the results obtained by the turbidity assay. As with the turbidity assay, the wild-type peptide and G3A peptide formed particles of very similar hydrodynamic diameters. Smaller structures were observed with the derivative peptides: N1A, I5A and L6A. Thus, in accordance with the turbidity assay, the DLS experiments clearly illustrate that no large particles were formed by the F2A peptide under the indicated experimental conditions.

Example 4

Examination of Amyloidogenic Performance of Wild Type Peptide and Derivatives Through Congo Red (CR) Binding Assay Congo red (CR) staining combined with polarization microscopy was utilized to test amyloidogenicity of the peptides of the present invention. Amyloid fibrils in general, and fibrillar IAPP in particular, bind CR and exhibit gold/green birefringence under polarized light [Cooper (1974) Lab. Invest. 31:232-8; Lansbury (1992) Biochemistry 31:6865-70].

Method and reagents—Peptide solutions incubated in a 10 mM Tris buffer (pH 7) for four days were dried on a glass microscope slide. Staining was effected by the addition of 1 mM CR in 10 mM Tris buffer pH 7.2 followed by a 1 minute incubation. To remove excess CR, slides were rinsed with double-distilled water and dried. Saturated CR solutions solubilized in 80% ethanol (v/v) were used for poorly aggregating peptides. In such cases, staining was effected without rinsing. Birefringence was determined using a WILD Makroskop m420 (×70) equipped with a polarizing stage.

Results—Wild type, N1A and G3A peptides bound CR and exhibited the characteristic green/gold birefringence (see FIGS. 6g, 6a and 6e for normal field and FIGS. 6h, 6b and 6f for polarized light microscopy, respectively). Peptides I5A and L6A, bound CR and exhibited rare but characteristic birefringence (FIGS. 6i and 6k for normal field and FIGS. 6j and 6l for polarized light, respectively). Peptide F2A (NAGAIL) showed no capability of binding CR (FIG. 6c for normal field and FIG. 6d for polarized light). Dried buffer solution stained with CR was used as a negative control (see FIGS. 6m and 6n for normal and polarized light, respectively). Interestingly, no significant difference in binding was observed for the negative control and the F2A peptide.

To substantiate the inability of F2A peptide to form fibrils, a peptide solution incubated for 14 days was used in the binding assay. Although some degree of aggregation was visually observed following two weeks of peptide "aging", CR staining showed no amyloid structure (results not shown). Under the same conditions wild-type peptide incubation resulted in significant CR birefringence.

Example 5

Ultrastructural Analysis of Thiefibrillogenic Peptide and Mutants

The fibrillogenic potential of the various peptides was assessed by electron microscopy analysis.

Method—Peptide solutions (2 mM peptide in 10 mM Tris buffer pH 7.2), were incubated overnight at room temperature. Fibrils formation was assessed using 10 μl sample placed on 200-mesh copper grids, covered with carbon-stabilized formvar film (SPI Supplies, West Chester Pa.). Following 20-30 seconds of incubation, excess fluid was removed and the grids were negatively stained with 2% uranyl acetate in water. Samples were viewed in a JEOL 1200EX electron microscope operating at 80 kV.

Results—To further characterize the structures formed by the various peptides, negative staining electron microscopy analysis was effected. In accordance with previous results, filamentous structures were observed for all peptides (FIGS. 7a-f) but F2A which generated amorphous fibrils (FIG. 7b). Frequency of appearance of fibrils formed by the I5A and L6A peptides (FIGS. 7e and 7f, respectively) was lower in comparison to that of wild type (FIG. 7d), N1A, and G3A peptides (FIGS. 7a and 7c, respectively). Although the EM fields shown for peptides F2A, I5A and L6A, were rarely observed, the results presented by these images support the quantitative results presented in the previous sections and thus provide qualitative analysis of fibril morphology.

The tangled net-like structures that were observed for the wild-type, N1A, and G3A peptides could be explained by the fast kinetics of formation of these fibrils (see Example 2). More distinct structures and longer fibrils, albeit less frequent, were observed with peptides I5A and L6A. These longer fibrils may be a result of a slower kinetics, which allow for a more ordered fibril organization.

Taken together, the qualitative results of the electron microscopy and CR analyses strongly suggest that the phenylalanine residue in the hexaamyloid peptide is crucial for its amyloidogenic potential.

Example 6

Mapping Recognition Domains in the hIAPP Basic Amyloidogenic Unit

Rational and MBP-IAPP Fusion Protein Synthesis

To systematically map and compare potential recognition domains, the ability of hIAPP (GenBank Accession No. gi:4557655) to interact with an array of 28 membrane-spotted overlapping peptides that span the entire sequence of hIAPP (i.e., $hIAPP_{1-10}$, $hIAPP_{2-11}$ ..., $hIAPP_{28-37}$) was addressed [Mazor (2002) J. Mol. Biol. 322:1013-24].

Materials and Experimental Procedures

Bacterial strains—*E. coli* strain TG-1 (Amersham Pharmacia, Sweden) was used for molecular cloning and plasmid propagation. The bacterial strain BL21(DE3) (Novagen, USA) was used for protein overexpression.

Engineering synthetic IAPP and MBP-IAPP fusion proteins—A synthetic DNA sequence of human IAPP modified to include a bacterial codon usage (SEQ ID NO: 58) was generated by annealing 8 overlapping primers (SEQ ID NOs. 50-57). PCR was effected through 30 cycles of 1 minute at 95° C., one minute at 55° C., and one minute at 72° C. The annealing product was ligated and amplified using primers IAPP1 (SEQ ID NO: 50) and IAPP8 (SEQ ID NO: 57). An MBP-IAPP (MBP GenBank Accession No. gi:2654021) fusion sequence was then constructed using the IAPP synthetic template, which was amplified using primer YAR2 (SEQ ID NO: 60) and primer YAR1 (SEQ ID NO. 59), thereby introducing a V8 Ek cleavage site and a $(His)_6$ tag at the N-terminus of IAPP. The two primers included a Not I and an Nco I cloning sites, respectively. The resultant PCR product was digested with Nco I and Not I and ligated into the pMALc2x-NN expression vector. The pMALc2x-NN expression vector was constructed by cloning the polylinker site of pMALc-NN[19] into pMALc2x (New England Biolabs, USA) [BACH (2001) J. Mol. Biol. 312:79-93].

Protein expression and purification—*E. coli* BL21 cells transformed with expression plasmid pMALc2x-IAPP encoding MBP-IAPP under the strong Ptac promoter were grown in 200 ml of LB medium supplemented with 100 μg/ml ampicillin and 1% (W/N) glucose. Once reaching an optical density of $A_{600}$=0.8, protein expression was induced with 0.1 or 0.5 mM IPTG at 30° C. for 3 hours (h).

Cell extracts were prepared in 20 mM Tric-HCl (pH 7.4), 1 mM EDTA, 200 mM NaCl and a protease inhibitors cocktail (Sigma) using a freeze-thaw followed by a brief sonication as previously described [Gazit (1999) J. Biol. Chem. 274:2652-2657]. Protein extracts were clarified by centrifugation at 20,000 g and stored at 4° C. MBP-IAPP fusion protein was purified by passing the extract over an amylose resin column (New England Biolabs, USA) and recovered by elution with 20 mM maltose in the same buffer. Purified MBP-IAPP was stored at 4° C. Protein concentration was determined using the Pierce Coomassie plus reagent (Pierce, USA) with BSA as a standard. MBP and MBP-IAPP protein fractions were analyzed on SDS/12% polyacrylamide gels, which were stained with GelCode Blue (Pierce, USA).

To study whether the disulfide bond in the MBP-IAPP are oxidized, purified MBP and MBP-IAPP proteins were reacted with 5 equivalents of N-iodoacetyl-N'-(8-sulfo-1-naphthyl) ethylenediamine (IAEDANS) (Sigma, Rehovot, Israel) for overnight at room temperature in the dark. Free dye was separated from labeled protein by gel filtration chromatography on a QuickSpin G-25 Sephadex column. MBP and MBP-IAPP fluorescence was then determined. Only small fluorescence labeling was detected (on average less than 0.1 probe molecules per protein molecules) and there was no significant difference between the labeling of MBP and MBP-IAPP, which suggested that the disulfide bridge in the expressed IAPP molecules was predominantly oxidized.

Results

Expression and purification of recombinant MBP-IAPP—Since previous attempts to express the intact hIAPP in bacteria were unsuccessful, the protein was expressed as an MBP fusion, which protected hIAPP from undesirable aggregation during expression [Bach (2001) J. Mol. Biol. 312:79-93]. Synthesis of the fusion protein was effected using a bacterial codon usage as shown in FIG. 8*a*. The resulting fusion sequence was cloned into pMALc2x-NN as shown in FIG. 8*b* and introduced into *E. coli* BL21(DE3). Growth conditions, cell extract preparation and protein purification were effected as described hereinabove. IPTG induction resulted in the accumulation of high levels of MBP-IAPP in the soluble fraction with less then 5% of the MBP-IAPP fusion protein was found in the insoluble fraction of the cell extract (data not shown). Aliquots from typical purification steps of MBP and MBP-IAPP are shown in FIG. 9. As shown, the 48 kDa MBP-IAPP accumulated to 25% of the total soluble protein as calculated by densitometric scanning of GelCode Blue-stained SDS/Polyacrylamide gels. When induced at 30° C. in a shake flask ($A_{600}$=2.0), MBP-IAPP accumulated as soluble protein in the cytoplasm at a level of about 150 mg/l of cell culture. Despite losses during purification, MBP-IAPP was purified to near-homogeneity at a yield of 80 mg/l of cells. For future application and convenient homogeneity purification of IAPP, in addition to the factor Xa cleavage site for removal of the MBP tag, an additional His-Tag was also included (FIG. 8*b*). The His-Tag could be removed by Ek V8 cleavage at the N-terminal Lys residue of the IAPP sequence, resulting in the release of wild type IAPP.

Example 7

Identification of Molecular Recognition Sequences in the hIAPP Polypeptide

IAPP peptide array construction—Decamers corresponding to consecutive overlapping sequences of $hIAPP_{1-37}$ SEQ ID NOs. 61-88) were synthesizes on a cellulose membrane matrix using the SPOT technique (Jerini A G, Berlin, Germany). The peptides were covalently bound to a Whatman 50 cellulose support (Whatman, Maidstone, England) via the C-terminal amino-acids. N-terminal acetylation was used for peptide scanning because of higher stability to peptide degradation, and better representation of the native recognition motif.

Peptides Synthesis—Peptide synthesis was effected using solid-phase synthesis methods performed by Peptron, Inc. (Taejeon, Korea). Correct identity of the peptides was confirmed by ion spray mass-spectrometry using a HP 1100 series LC/MSD [Hewlett-Packard Company, Palo Alto, Calif.]. The purity of the peptides was confirmed by reverse phase high-pressure liquid chromatography (RP-HPLC) on a $C_{18}$ column, using a 30 minute linear gradient of 0 to 100% acetonitrile in water and 0.1% trifluoroacetic acid (TFA) at flow rate of 1 ml/min.

Binding studies—The cellulose peptide array was initially blocked with 5% (VN) non fat milk in Tris buffered saline (TBS, 20 mM Tris pH 7.5, 150 mM NaCl). Thereafter, cellulose membrane was incubated in the presence of 10 μg/ml MBP-IAPP$_{1-37}$ at 4° C. for 12 h in the same blocking buffer. The cellulose membrane was then washed repeatedly with 0.05% Tween 20 in TBS. MBP-IAPP$_{1-37}$ bound to the cellulose membrane was detected with an anti MBP monoclonal antibody (Sigma, Israel). HRP-conjugated goat anti mouse antibodies (Jackson Laboratories, USA) were used as a secondary antibody. Immunoblots were developed using the Renaissance western blot Chemiluminescence Reagent (NEN, USA) according to Manufacturer's instructions and signal was quantified using densitometry. Regeneration of the cellulose membrane for reuse was carried out by sequential washing with Regeneration buffer I including 62.5 mM Tris, 2% SDS, 100 Mm 2-mercaptoethanol, pH 6.7, and Regeneration buffer II including 8 M urea, 1% SDS, 0.1% 2-mercaptoethanol. Efficiency of the washing steps was monitored by contacting the membrane with the chemiluminescence reagent, as described.

Results

Identification of binding sequences in the LAPP polypeptide—To identify structural motifs in the IAPP molecule that mediates the intermolecular recognition between hIAPP molecules, 28 possible overlapping decamers corresponding to amino acids 1-10 up to 28-37 of the hIAPP$_{1-37}$ molecule were synthesized on a cellulose membrane matrix. Cellulose membrane-bound peptides were incubated with MBP-hIAPP$_{1-37}$ overnight. Following washing of the cellulose membrane in a high-salt buffer, immunoblots on the cellulose membrane were analyzed and binding was quantified by densitometry (FIG. 10b). It will be appreciated that the measured binding is semiquantitative, since peptide coupling efficiency during synthesis can vary.

As shown in FIGS. 10a-b, a number of peptide segments exhibited binding to MBP-IAPP; An amino acid sequence localized to the center of the IAPP polypeptide (i.e., hIAPP$_{7-16}$ to hIAPP$_{12-21}$) displayed the most prominent binding to MBP-hIAPP$_{1-37}$. Another binding region was identified at the C-terminal part of IAPP (hIAPP$_{19-28}$ to hIAPP$_{21-30}$), although binding in this case was considerably less prominent; A third binding spot was located to the N-terminal part of IAPP (hIAPP$_{2-11}$), however, no typical distribution around a central motif was evident in this case, suggesting that this result may be false. Even after overexposure of the blot (data not shown), no binding near this peptide (to either hIAPP$_{1-10}$ or hIAPP$_{3-12}$) was detected. Furthermore given the close proximity of the 2-11 region to the disulfide bridge may not allow the process of fibrillization under physiological conditions.

To rule out involvement of MBP itself in binding the arrayed peptides, the peptide coupled cellulose membrane was incubated with MBP alone and analyzed by immunobloting. No binding was identified after development of the membrane (not shown).

These results identified in addition to the previously defined binding motif of hIAPP [i.e., basic amyloidogenic unit, hIAPP20-29, Westermark (1990) Proc. Natl. Acad. Sci. 13:5036-40; Tenidis (2000) J. Mol. Biol. 295:1055-1071; Azriel and Gazit (2001) J. Biol. Chem. 276:34156-34161], a major central domain of molecular recognition within hIAPP.

The profile of the binding distribution of the peptide array (FIG. 10b), suggests that NFVLH (SEQ ID No. 17) may serve as the core recognition motif.

Example 8

Characterization of Aggregation Kinetics of hIAPP Peptide Fragments as Monitored by Turbidity Measurements Binding analysis of the recombinant MBP-hIAPP fusion protein to the hIAPP peptide array (Example 7), identified a putative self-assembly domain within the central part of the hIAPP protein.

In order to identify the minimal structural motif that is capable of forming amyloid fibrils, a series of peptides encompassed within the putative self-assembly domain were tested for aggregation as monitored using turbidity measurements at 405 nm.

Table 3 below, illustrates the examined peptides.

TABLE 3

| HIAPP peptide fragments (hIAPP coordinates) | SEQ ID NO: | Peptide sequence |
| --- | --- | --- |
| 14-22 | 14 | NFLVHSSNN |
| 14-20 | 15 | NFLVHSS |
| 15-20 | 16 | FLVHSS |
| 14-18 | 17 | NFLVH |
| 15-19 | 18 | FLVHS |
| 15-18 | 19 | FLVH |

Materials and Experimental Procedures

Kinetic Aggregation Assay—freshly prepared peptide stock solutions were generated by dissolving the lyophilized form of the peptides in dimethyl sulfoxide (DMSO) at a concentration of 100 mg/ml. To avoid any pre-aggregation, fresh stock solutions were prepared for each experiment. Peptide stock solutions were diluted into the assay buffer in enzyme-linked immunosorbent assay (ELISA) plate wells as follows: 8 μL of peptide stock solutions were added to 92 μL of 10 mM Tris, pH 7.2 (hence the final concentration of the peptide was 8 mg/ml in the presence of 8% DMSO). Turbidity data were collected at 405 nm. Buffer solution containing the same amount of DMSO as the tested samples was used as blank, which was subtracted from the results. Turbidity was measured continuously at room temperature using THERMOmax ELISA plate reader (Molecular Devices, Sunnyvale Calif.).

Results

Turbidity assay was performed in-order to determine the ability of the various peptides (Table 3) to aggregate in an aqueous medium. Fresh stock solutions of the different peptide fragments were made in DMSO, and then diluted into a Tris buffer solution and turbidity, as a hallmark of protein aggregation, was monitored for two hours. As shown in FIG. 11, the peptides NFLVHSS, FLVHSS and FLVHS exhibited high turbidity. It will be appreciated that the lag-time, as was previously reported for amyloid formation by the NFGAIL short peptide [Tenidis (2000) Supra], is very short or lacking at all and thus could not be detected under these experimental conditions, however the aggregation kinetic profiles were similar to those obtained for the hexapeptide hIAPP$_{22-27}$ (NF- GAIL). On the other hand, the peptide NFLVHSSNN exhibited very low turbidity, while NFLVH and FLVH have shown almost no turbidity at all. Even after significantly longer incubation no significant turbidity was observed with the latter two peptides. The lack of amyloid fibrils formation may be due to electrostatic repulsion of the partially charged histidine residues.

Example 9

Examination of hIAPP Peptide Amyloidogenic Through Congo Red (Cr) Binding Assay

Congo red (CR) staining combined with polarization microscopy was utilized to test amyloidogenicity of the peptides of the present invention. Amyloid fibrils bind CR and exhibit gold/green birefringence under polarized light [Puchtler (1966) J. Histochem. Cytochem. 10:355-364].

Materials and Experimental Procedures

Congo Red Staining and Birefringence—A 10 µL suspension of 8 mg/ml peptide solution in 10 mM Tris buffer, pH 7.2 aged for at least one day was allowed to dry overnight on a glass microscope slide. Staining was performed by the addition of a 10 µL suspension of saturated Congo Red (CR) and NaCl in 80% ethanol (v/v) solution as previously described [Puchtler (1966) Supra]. The solution was filtered via 0.45 µm filter. The slide was then dried for few hours. Birefringence was determined with a SZX-12 Stereoscope (Olympus, Hamburg, Germany) equipped with cross polarizers.

Results

Congo Red Staining and Birefringence—In order to determine any possible amyloidal nature of the aggregates formed at the turbidity assay (see Example 8), a CR birefringence assay was performed. Peptide fragments were tested for amyloidogenecity by staining with CR and examination under a light microscope equipped with cross-polarizers. Consistent with the kinetic assay results, and as shown in FIGS. 120*b-c* and 12*e*, the peptides NFLVHSS, FLVHSS and FLVHS exhibited a typical birefringence. On the other hand, peptides NFLVHSSNN, NFLVH and FLVH exhibited very weak birefringence or no birefringence at all (FIGS. 12*a*, 12*d* and 12*f*). Peptide NFLVHSSNN exhibited a weaker characteristic birefringence (FIG. 12*a*). The peptide NFLVH exhibited a powerful smear of birefringence at the edges of the sample (FIG. 12*d*). The peptide FLVH exhibited no birefringence (FIG. 12*f*). In order to test whether the FLVH peptide did not form amyloid fibrils due to a long lag-time, a sample of five days aged peptide solution was examined. The same peptide was also tested in aqueous solution and at very high concentrations (10 mg/ml), however no Birefringence was detected in all cases indicating the peptide did not form amyloid (data not shown).

Example 10

Ultrastructural Analysis of the Fibrillogenic hIAPP Peptides

The fibrillogenic potential of the various peptides was assessed by electron microscopy analysis.

Materials and Experimental Procedures

Transmission Electron Microscopy—A 10 µL sample of 8 mg/ml peptide solution in 10 mM Tris buffer, pH 7.2 aged for at least one day was placed on 400-mesh copper grids (SPI supplies, West Chester Pa.) covered by carbon-stabilized Formvar film. Following 1 minute, excess fluid was removed, and the grid was then negatively stained with 2% uranyl acetate in water for another two minutes. Samples were viewed in a JEOL 1200EX electron microscope operating at 80 kV.

Results

Figure 13A:
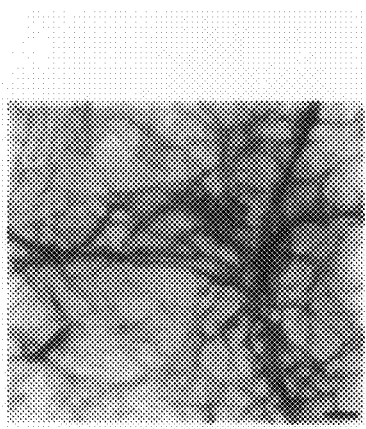
Figure 13B:
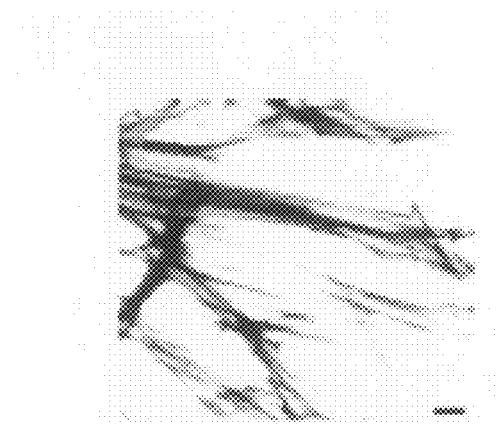
Figure 13C:
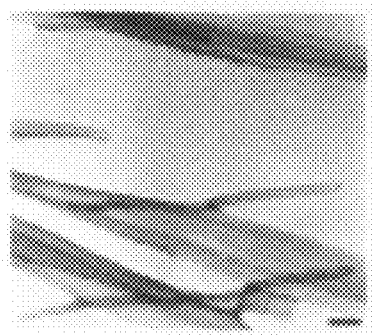
Figure 13D:
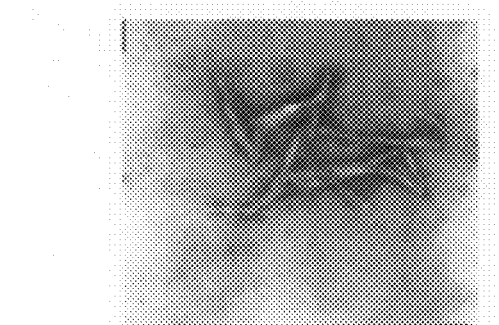
Figure 13E:
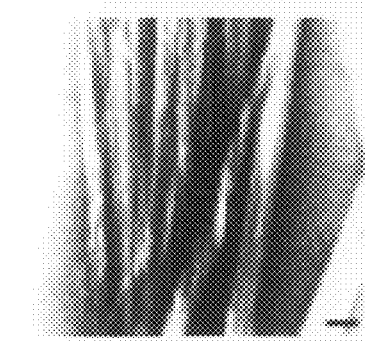
Figure 13F:
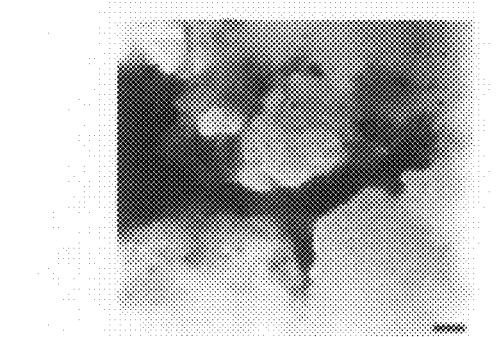

To further characterize the structures formed by the various peptides, negative staining electron microscopy analysis was effected. In accordance with previous results, all peptide fragments exhibited fibrillar structures except the FLVH peptide in which only amorphous aggregates were found (FIGS. 13*a-f*). NFLVHSSNN peptide exhibited long thin coiling filaments similar to those formed by the full-length peptide as described above (FIG. 13*a*). Peptides NFLVHSS, FLVHSS, FLVHS exhibited large broad ribbon-like fibrils as described for the NFGAIL fragment [Tenidis (2000) Supra., FIGS. 13*c-e*, respectively]. The fibrils formed by NFLVH peptide were thin and short and could be considered as protofilaments rather than filaments. Their appearance was at much lower frequency, and the EM picture does not represent the general fields but rather rare events (FIG. 13*d*). As shown in FIG. 13*f*, the FLVH peptide mediated the formation of amorphous aggregates.

Example 11

Secondary Structure Analysis of hIAPP Peptide Fragments

Fourier transform infrared spectroscopy (FT-IR) was effected to determine the secondary structure of the hIAPP amyloidogenic peptide fibrils and the non-fibrillar peptides.

Materials and Experimental Procedures

Fourier Transform Infrared Spectroscopy—Infrared spectra were recorded using a Nicolet Nexus 470 FT-IR spectrometer with a DTGS detector. Samples of aged peptide solutions, taken from turbidity assay, were suspended on a $CaF_2$ widows (Sigma)-plate and dried by vacuum. The peptide deposits were resuspended with double-distilled water and subsequently dried to form thin films. The resuspension procedure was repeated twice to ensure maximal hydrogen to deuterium exchange. The measurements were taken using a 4 $cm^{-1}$ resolution and 2000 scans averaging. The transmittance minima values were determined by the OMNIC analysis program (Nicolet).

Results

FT-IR studies—As shown in FIG. 14*a-f*, all the fibrillar peptides exhibited FT-IR spectra with a well-defined minimum bands typical for β-sheet structure around 1620-1640 $cm^{-1}$. On the other hand the spectrum of the tetrapeptide FLVH that has no appearance for fibrils according to the other methods, is typical for a random coil structure. The NFLVHSSNN peptide spectrum exhibited a transmittance minimum at 1621 $cm^{-1}$ indicating a large β-sheet content, as well as minima at 1640 $cm^{-1}$ and 1665 suggesting presence of non-β structures. Another minor minimum was observed at 1688 $cm^{-1}$ indicative for anti-parallel β-sheet (FIG. 14*a*). The NFLVHSS peptide spectrum exhibited major minimum band at 1929 $cm^{-1}$ 1675 $cm^{-1}$. this spectrum is classical for an anti-parallel β-sheet structure (FIG. 14*b*). A similar spectrum was observed for the peptide FLVHS with a major minimum at 1625 $cm^{-1}$ and a minor minimum at 1676 $cm^{-1}$ (FIG. 14*e*). The spectrum of FLVHSS peptide showed also a major minimum at 1626 $cm^{-1}$. The spectrum had also some minor minima around 1637-1676 $cm^{-1}$ but those were shaped more like noise than signal (FIG. 14*c*). The spectrum of NFLVH peptide showed a minimum at 1636 $cm^{-1}$ which was also indicative of β-sheet, however, in comparison with the other spectra, this band was shifted which could indicate presence of non-β structures, as well as observed minima at 1654 cm$^{-1}$ and 1669 cm$^{-1}$ (FIG. 14d). By contrast, the FLVH peptide spectrum exhibited no minimum at 1620-1640 cm$^{-1}$, but showed multiple minima around 1646-1675 cm$^{-1}$ typical to random coil structure (FIG. 14f).

To study whether the FLVH tetrapeptide could not form amyloid fibrils at all or the undetectable fibrils formation was a result of a slow kinetics, a solution of the peptide at the same experimental conditions was incubated for two months and the existence of fibrils was tested. However, no evidence for amyloid fibril formation was detected using EM microscopy, CR staining, or FT-IR spectroscopy. These results may suggest that tetrapeptides are incapable of forming fibrils due to energetic consideration. That is, the energetic contribution of the stacking of a strand composed of three peptide bonds is lower than the entropic cost of oligomerization.

Taken together, the ultrastructural observations are consistent with the findings as determined by the turbidity and Congo red birefringence assays. All together the experimental data identified a novel pentapeptide element within the hIAPP peptide, the FLVHS peptides, which has strong amyloid forming capability. Interestingly, an NFLVH peptide found in the same central domain of the hIAPP polypeptide was found to be amyloidogenic however, the ability thereof to form fibrils was somehow inferior.

Example 12

Identification of the Minimal Amyloidogenic Peptide Fragment of Medin

Background

Medin (GenBank Accession No. gi:5174557) is the main constitute of aortic medial amyloid deposits [Häggqvist (1999) Proc. Natl. Acad. Sci. USA. 96:8674-8669]. Previous studies found aortic medial amyloid in 97% of the subjects above the age of 50 [Mucchiano (1992) Am. J. Pathol. 140: 811-877]. However, the pathological role of those amyloid deposits is still unknown. It was suggested that these amyloid play a role in the diminished elasticity of aortic vessels that is related to old age [Mucchiano (1992) Supra; Häggqvist (1999) Supra]. While the study clearly identified a tryptic peptide NFGSVQFV as the medin amyloidogenic peptide, the minimal sequence of the peptide that is still amyloidogenic and the molecular determinants that mediate the amyloid formation process were not determined. Such information is critical for true understanding of the fibrillization process in the specific case of Medin but also as a paradigm for the process of amyloid fibrils formation in general.

The minimal active fragment of Medin was determined using functional and structural analyses of truncated analogues derived from the published octapeptide [Häggqvist (1999) Supra].

Materials and Experimental Procedures

Peptide synthesis is described in Example 7.

Table 4 below illustrates the studied peptides.

TABLE 4

| Peptide sequence | SEQ ID NO: |
|---|---|
| NH$_2$-NFGSVQVF-COOH | 20 |
| NH$_2$-NFGSVQ -COOH | 21 |
| NH$_2$-NFGSV -COOH | 22 |
| NH$_2$- FGSVQ -COOH | 23 |

TABLE 4-continued

| Peptide sequence | SEQ ID NO: |
|---|---|
| NH$_2$- GSVQ -COOH | 24 |
| NH$_2$- FGSV -COOH | 25 |
| NN$_2$-NAGSVQ -COOH | 26 |

Results

In order to get further insights into the structural elements of Medin that retain the molecular information needed to mediate a process of molecular recognition and self-assembly, the ability of short peptide fragments and analogues of Medin to form amyloid fibrils in vitro was studied. FIG. 15a shows a schematic representation of the chemical structure of the largest peptide fragment studied.

Example 13

Kinetics of Aggregation of Medin-Derived Peptide Fragments

Turbidity assay was effected as described in Example 8.

In order to get first insights regarding the aggregation potential of the various Medin derived peptides, turbidity assay was performed. Freshly made stocks of the amyloidogenic octapeptide and truncated analogues thereof were prepared in DMSO. The peptides were than diluted to aqueous solution and the turbidity was monitored by following the absorbance at 405 nm as a function of time. As shown in FIG. 16a, the NFGSV pentapeptide exhibited the highest degree of aggregation within minutes of incubation. Physical examination of the solution indicated that the peptide formed a gel structure. The kinetics of aggregation of the NFGSVQV octapeptide was too fast to be measured since turbidity was already observed immediately with the dilution into aqueous solution (FIGS. 16a-b). Similar fast kinetics were also observed with the GSVQ tetrapeptide. The truncated NFGSVQ, FGSVQ, and FGSV peptides showed a gradual increase in turbidity over ~30 minutes (FIG. 16b) which was followed by a slight decrease, which could be explained by sedimentation of large aggregates. Altogether, such kinetics and turbidity values were similar to those previously observed with amyloidogenic peptides of similar size (Azriel and Gazit, 2001).

Example 14

Ultrastructural Analysis of Medin-Derived Peptide Fragments

Electron microscopy analysis was effected as described in Example 10.

Figure 17A:
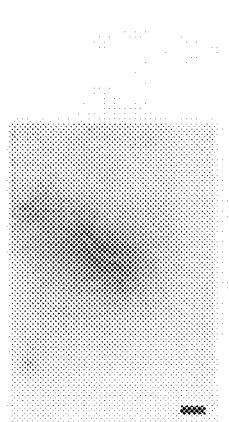
Figure 17B:
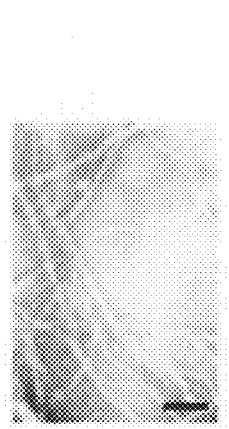
Figure 17C:
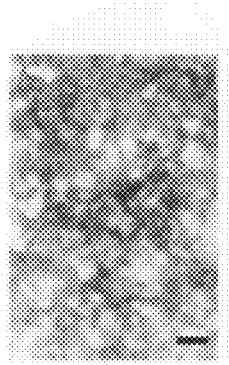
Figure 17D:
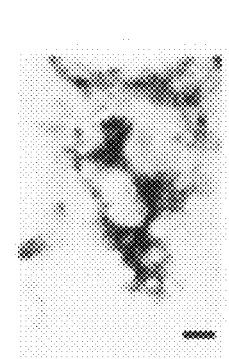
Figure 17E:
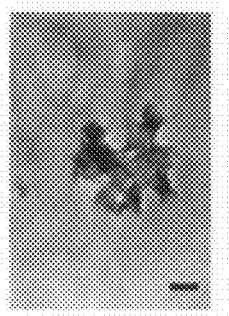
Figure 17F:
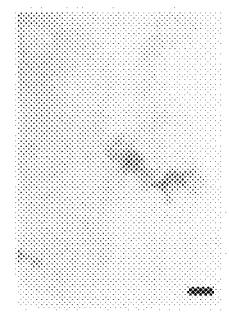

The fibrillization potential of Medin-derived peptide fragments was effected by electron microscopy (EM) using negative staining. Stock solutions of the peptide fragments were suspended and aged for 4 days. Fibrillar structures were clearly seen in solutions that contained both the NFGSVQFA octapeptide (FIG. 17a) and the truncated NFGSVQ (FIG. 17b). In both cases the structures were similar to those observed with much longer polypeptides, such the IAPP and the β-amyloid (Aβ) polypeptides. The shorter gel-forming NFGSV pentapeptide did not form a typical amyloid structure but a network of fibrous structures (FIG. 17c). It should be noted that fibrous networks were recently observed upon the gelation of the glutathione peptide [Lyon and Atkins, (2001) J. Am. Chem. Soc. 123:4408-4413]. No typical fibrils could be detected in solutions that contained the FGSVQ pentapeptide, the GSVQ tetrapeptide, or the FGSV tetrapeptide in spite of extensive search. While in the case of the FGSVQ peptide (FIG. 17d) somewhat fibrillar and ordered structure could be seen, although significantly different than those formed by typical amyloidogenic peptide), in the case of the GSVQ and the FGSV peptides, no fibrillar structures could be found (FIGS. 17e and 17f, respectively).

Example 15

Examination of Amyloidogenic Performance of Medin-Derived Peptides Through Congo Red (CR) Binding Assay CR staining was effected as described in Example 9.

Figure 18A:
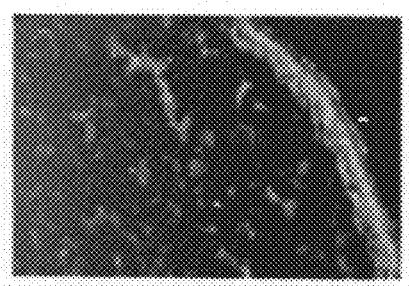
Figure 18B:
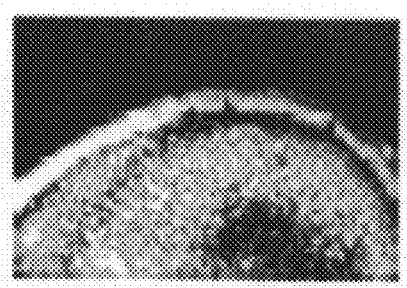
Figure 18C:
Figure 18D:
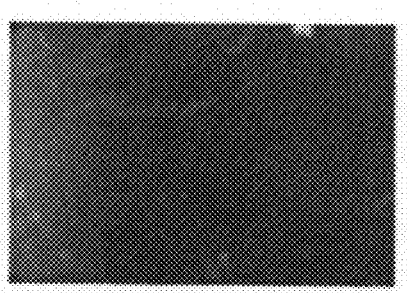
Figure 18E:
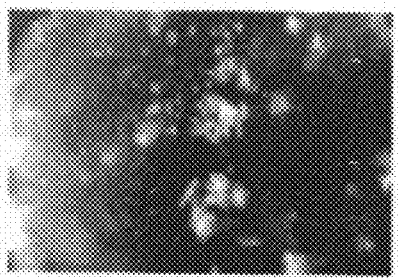
Figure 18F:
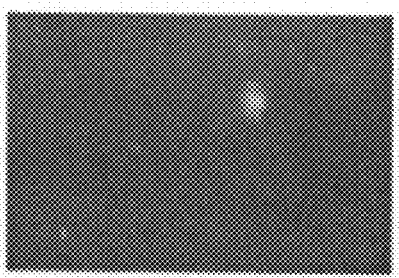

A CR staining was effected to determine whether the structures formed by the various Medin-derived peptides show a typical birefringence. As shown in FIG. 18b, the NFGSVQ hexapeptide bound CR and exhibited a characteristic bright and strong green-gold birefringence. The NFGSVQFV octapeptide also exhibited significant birefringence (FIG. 18a), although less typical than that observed with the hexapeptide. The gel-forming NFGSV peptide deposits exhibited very low degree of birefringence (FIG. 18c). The FGSVQ and FGSV peptide showed no birefringence upon staining with CR (FIGS. 18d and 18f, respectively). There was clearly no significant difference between those two peptides and a negative control (i.e., buffer solution with no peptide) Interestingly, unexpected high level of birefringence was observed with the GSVQ tetrapeptide (FIG. 18e), while the morphology of the structures formed therefrom (FIG. 18e) was clearly different from that of amyloid fibrils, indicating that these structures may have a significant degree of order that is reflected in strong birefringence.

Example 16

The Effect of Phenylalanine Substitution on the Self-Assembly of Medin

T elucidate a possible role for the phenylalanine residue in the process of amyloid fibrils formation by the minimal amyloid-forming hexapeptide, the phenylalanine amino acids was replaced with an alanine. The alanine-substituted peptide was prepared and examined in the same way as described for the various fragments of Medin. As shown in FIG. 19a, a significantly lower turbidity was observed with the alanine-substituted peptide as compared to the wild-type hexapeptide. When aged solution of the NAGSVQ peptide was visualized by EM, no clear fibrillar structures could be detected (FIG. 19b). This is in complete contrast to the high abundance fibrillar structures seen with the wild-type peptide (FIG. 17b). Furthermore, the structures that were visualized did not show any degree of order as observed with the NFGSV and FGSVQ peptides as described above, FIGS. 17c-d, but were very similar to the completely non-fibrillar structures as were observed with the FGSV tetrapeptide (FIG. 17e). Interestingly, some degree of birefringence could still be detected (FIG. 19c) with the alanine-substituted peptide (as was observed with the GSVQ peptide, FIG. 18e). These results raise further doubts regarding the use of CR staining as a sole indicator of amyloid formation [Khurana (2001) J. Biol. Chem. 276:22715-22721].

Altogether these results show that the truncated fragment of Medin which is capable of forming amyloid fibrils is the hexapeptide NFGSVQ (SEQ ID NO: 21), although a shorter pentapeptide fragment, NFGSV (SEQ ID NO: 22), exhibited a network of fibrous structures which were not typical of amyloids. The amyloid forming NFGSVQ hexapeptide is noticeably similar to the minimal amyloidogenic fragment of the islet amyloid polypeptide (IAPP, see Examples 1-5). Taken together, the results are consistent with the assumed role of stacking interactions in the self-assembly processes that lead to the formation of amyloid fibrils and the suggested correlation between amyloid fibrils and β-helix structures.

Example 17

Identification of the Minimal Amyloidogenic Peptide Fragment of Human Calcitonin Human Calcitonin (hCT, GenBank Accession No. gi:179880) is a 32 amino acid long polypeptide hormone that is being produced by the C-cells of the thyroid and is involve in calcium homeostasis [Austin and Health (1981) N. Engl. J. Med. 304:269-278; Copp (1970) Annu. Rev. Physiol. 32:61-86; Zaidi (2002) Bone 30:655-663]. Amyloid fibrils composed of hCT were found to be associated with medullary carcinoma of the thyroid [Kedar (1976) Isr. J. Sci. 12:1137; Berger (1988) Arch. A. Pathol. Anat. Histopathol. 412:543-551; Arvinte (1993) J. Biol. Chem. 268:6415-6422]. Interestingly, synthetic hCT was found to form amyloid fibrils in vitro with similar morphology to the deposits found in the thyroid [Kedar (1976) Supra; Berger (1988) Supra; Arvinte (1993) Supra; Benvenga (1994) J. Endocrinol. Invest. 17:119-122; Bauer (1994) Biochemistry 33:12276-12282; Kanaori (1995) Biochemistry 34:12138-43; Kamihara (2000) Protein Sci. 9:867-877]. The in vitro process of amyloid formation is affected by the pH of the medium [23]. Electron microscopy experiments have revealed that the fibrils formed by hCT are approximately 80 Å in diameter and up to several micrometers in length. The fibrils are often associated with one another and in vitro amyloid formation is affected by the pH of the medium [Kamihara (2000) Supra.].

Calcitonin has been used as a drug for various diseases including Paget's disease and osteoporosis. However, the tendency of hCT to associate and form amyloid fibrils in aqueous solutions at physiological pH is a significant limit for its efficient use as a drug [Austin (1981) Supra; Copp (1970) Supra; Zaidi (2002) Supra]. Salmon CT [Zaidi (2002) Supra], the clinically used alternative to hCT, causes immunogenic reaction in treated patients due to low sequence homology. Therefore, understanding the mechanism of amyloid formation by hCT and controlling this process is highly important not only in the context of amyloid formation mechanism but also as a step toward improved therapeutic use of Calcitonin.

Circular dichroism (CD) studies have shown that in water monomeric hCT has little ordered secondary structure at room temperature [Arvinte (1993) Supra]. However, studies of hCT fibrils using circular dichroism, fluorescence, and infrared spectroscopy revealed that fibrillated hCT molecules have both α-helical and β-sheet secondary structure components [Bauer (1994) Supra]. NMR spectroscopy studies have shown that in various structure promoting solvents like TFE/H$_2$O, hCT adopts an amphiphilic α-helical conformation, predominantly in the residue range 8-22 [Meadows (1991) Biochemistry 30:1247-1254; Motta (1991) Biochemistry 30:10444-10450]. In DMSO/H$_2$O, a short double-stranded antiparallel β-sheet form in the central region made by residues 16-21 [Motta (1991) Biochemistry 30:2364-71].

Based on this structural data and the proposed role of aromatic residues in the process of amyloid formation, the present inventor has identified a short peptide fragment, which is sufficient for mediating Calcitonin self-assembly [Reches (2002) J. Biol. Chem. 277:35475-80].

The studied peptides—Based on the previously reported susceptibility of amyloid formation to acidic pH [Kanaori (1995) Supra], it was suggested that negatively-charged amino-acids, which undergo protonation at low pH, may play a key role in the process of amyloid formation. The only negatively-charged amino-acid in hCT is Asp[15] (FIG. 20a). Furthermore, a critical role for residues Lys[18] and Phe[19] in the oligomerization state and bioactivity of hCT was recently shown [Kazantzis (269) Eur. J. Biochem. 269:780-91]. Together with the occurrence of two phenylalanine residues in the region focused the structural analysis of the amyloidogenic determinants in hCT to amino acids 15-19. FIG. 20b shows a schematic representation of the chemical structure of the longest peptide and Table 5 below, indicates the various peptide fragments that were used in the study.

TABLE 5

| Amino acid coordinates on hCT | Peptide sequence | SEQ ID NO: |
| --- | --- | --- |
| 15-19 | NH$_2$-DFNKF-COOH | 27 |
| 16-19 | NH$_2$- FNKF-COOH | 28 |
| 15-18 | NH$_2$-DFNK -COOH | 29 |
| 15-17 | NH$_2$-DFN  -COOH | 30 |
| F > A 15-19 | NH$_2$-DANKF-COOH | 31 |

Example 18

Ultrastructural Analysis of Calcitonin-Derived Peptide Fragments

Electron microscopy analysis was effected as described in Example 10.

Figure 21A:
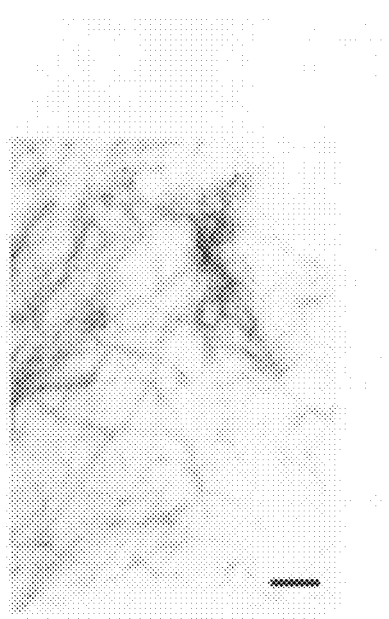
Figure 21B:
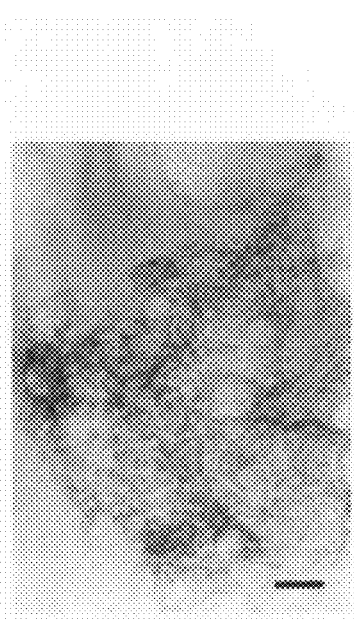
Figure 21C:
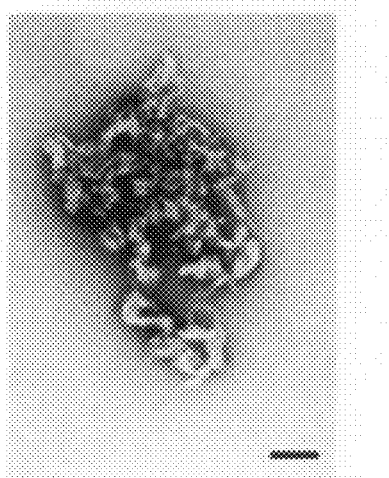
Figure 21D:
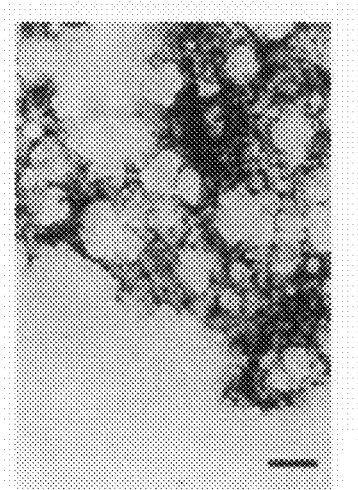

The fibrillization potential of Calcitonin-derived peptide fragments was effected by electron microscopy (EM) using negative staining. Stock solutions of the peptide fragments were suspended in 0.02M NaCl, 0.01M Tris pH 7.2, aged for 2 days and negatively stained. Fibrillar structures, similar to those formed by the full-length polypeptide [Arvinte (1993) Supra; Benvenga (1994) Supra; Bauer (1994) Supra; Kanaori (1995) Supra; Kamihara (2000) Supra], were clearly seen with high frequency in solutions that contained the DFNKF pentapeptide (FIG. 21a). The shorter DFNK tetrapeptide also formed fibrillar structures (FIG. 21b). However, the structures formed were less ordered as compared to those formed by the DFNKF pentapeptide. The amount of fibrillar structures formed by DFNK was also lower as compared to the DFNKF peptapeptide. No clear fibrils could be detected using solutions that contained the FNKF tetrapeptide and the DFN tripeptide, in spite of extensive search. In the case of the FNKF tetrapeptide only amorphous aggregates could be found (FIG. 21c). The DFN tripeptide formed more ordered structures (FIG. 21d) that resembled the structure formed by gel-forming tripeptide [Lyon (2001) Supra]. To study whether the FNKF tetrapeptide and the DFN tripeptide peptide cannot form fibrils whatsoever or the observation is a result of slow kinetics, a solution of the peptides at the same experimental conditions was incubated for two weeks. Also in this case no clear fibrillar structures could be detected (data not shown).

Example 19

Examination of Amyloidogenic Performance of Calcitonin-Derived Peptides Through Congo Red (CR) Binding Assay CR staining was effected as described in Example 9.

Figure 22A:
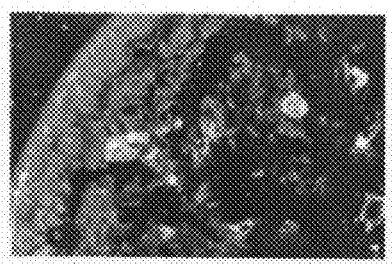
Figure 22B:
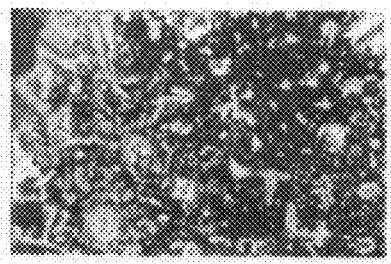
Figure 22C:
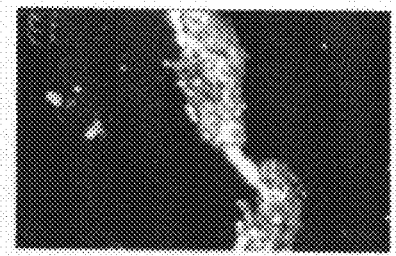
Figure 22D:
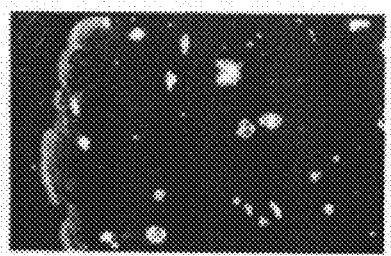

A CR staining was effected to determine whether the structures formed by the various hCT-derived peptides show a typical birefringence. As shown in FIGS. 22a-d, all the studies peptides showed some degree of birefringence. However, the green birefringence, which was observed with the DFNKF-pentapeptide was clear and strong (FIG. 22a). The level of birefringence that was observed with the other peptides was lower but significant since no birefringence could be detected using control solutions which did not contain the peptides. The lower level of birefringence of the DFNK tetrapeptide (FIG. 22b) was consistent with the lower extent of fibrillization as observed using EM (FIG. 21b). It will be appreciated, though, that the birefringence observed with the FNKF tetrapeptide and the DFN tripeptide might represent some degree of ordered structures [Lyon (2001) Supra].

Example 20

Secondary Structure of the Aggregated hCT-Derived Peptides

FT-IR spectroscopy was effected as described in Example 11.

Amyloid deposits are characteristic of fibrils rich with β-pleated sheet structures. To get a quantitative information regarding the secondary structures that were formed by the various peptide fragments FT-IR spectroscopy was used. Aged peptide solutions were dried on CaF$_2$ plates forming thin films as described in Example 11. As shown in FIG. 23, the DFNKF pentapeptide exhibited a double minima (at 1639 cm$^{-1}$ and 1669 cm$^{-1}$) an amide I FT-IR spectrum that is consistent with anti-parallel β-sheet structure and is remarkably similar to the spectrum of the amyloid-forming hexapeptide fragment of the islet amyloid polypeptide [Tenidis (2000) Supra]. The amide I spectrum observed with the DFNK tetrapeptide (FIG. 23) was less typical of a β-sheet structure. While it exhibited a minimum at 1666 cm-1 that may reflect an anti-parallel β-sheet it lacked the typical minimum around 1620-1640 cm$^{-1}$ that is typically observed with β-sheet structures. The FNKF tetrapeptide exhibited a FT-IR spectrum that is typical of a non-ordered structure (FIG. 23) and is similar to spectra of the short non-amyloidogenic fragments of the islet amyloid polypeptide [Tenidis (2000) Supra]. The DFN tripeptide exhibited a double minima (at 1642 cm$^{-1}$ and 1673 cm$^{-1}$, FIG. 23) amide I FT-IR spectrum that is consistent with a mixture of β-sheet and random structures. This may further indicate that the structures observed by EM visualization may represent some degree of ordered structure composed of predominantly β-sheet structural elements.

Example 21

The Effect of Phenylalanine Substitution on the Self-Assembly of Calcitonin-Derived Peptides In order to get insight into a possible role for the phenylalanine residues in the process of Calcitonin self-assembly, the phenylalanine amino acids were replaced with alanine in the context of the pentapeptide (SEQ ID NO: 31). When aged solution of the DANKF pentapeptide was visualized by EM, no clear fibrillar structures could be detected (FIG. 24a). Structures that were visualized exhibited some degree of order (as compared to the amorphous aggregates seen with the FNKF tetrapeptide), however, no green-gold birefringence could be observed (FIG. 24b). The FT-IR spectrum of the DANKA pentapeptide was similar to that of the FNKF tetrapeptide and other short non-amyloidogenic peptide, typical of non-ordered structures [Tenidis (2000) Supra]. Taken together, the effect of the phenylalanine to alanine substitution is very similar to the effect of such a change in the context of a short amyloid-forming fragment of the islet amyloid polypeptide [Azriel (2001) Supra].

Altogether, the ability of an hCT-derived pentapeptide (SEQ ID NO: 27) to form well-ordered amyloid fibrils was demonstrated. The typical fibrillar structure as seen by electron microscopy visualization (FIG. 21a), the very strong green birefringence upon staining with CR (FIG. 22a), and the typical anti-parallel β-sheet structure (FIG. 23a), all indicate that the DFNKF pentapeptide is a very potent amyloid forming agent. Other pentapeptides capable of self-assembling were shown in hereinabove. Yet, in terms of the degree of birefringence and electron microscopy morphology, the hCT fragment seems to be the pentapeptide with the highest amyloidogenic potential similar to the potent amyloidogenic fragment of the β-amyloid (Aβ) polypeptide, KLVFFAE [Balbach (2000) Biochemistry 39:13748-59]. It is possible that electrostatic interactions between the opposing charges on the lysine and aspartic acids direct the formation of ordered antiparallel structure. Interestingly, the DFNK polypeptide exhibited a significantly lower amyloidogenic potential as compared to the DFNKF peptide. It is possible that a pentapeptide is a lower limit for potent amyloid former. This is consistent with recent results that demonstrate that two pentapeptides of IAPP, NFLVH and FLVHS, can form amyloid fibrils, but their common denominator, the tetrapeptide FLVH, could not form such fibrils (see Examples 1-5).

Example 22

Identification of an Amyloidogenic Peptide from Lactotransferrin

Amyloid fibril formation by lactotransferrin (GenBank Accession No. gi:24895280) is associated familial subepithelial corneal amyloid formation [Sacchettini and Kelly (2002) Nat Rev Drug Discov 1:267-75]. Based on the proposed role of aromatic residues in amyloid self-assembly, the amyloidogenic features of a Lactotransferrin-derived peptide, LFNQTG (SEQ ID NO: 32) were studied.

Materials and Experimental Procedures—Described in Examples 7 and 10.

Results—To characterize the ability of the Lactotransferrin-derived peptide to form fibrillar supramolecular ultrastructures, negative staining electron microscopy analysis was effected. As shown in FIG. 25, under mild conditions, filamentous structures were observed for the selected peptide, suggesting that LFNQTG of Lactotransferrin is important for the polypeptide self-assembly. These results further substantiate the ability of the present invention to predict amyloidogenic peptide sequences.

Example 23

Identification of an Amyloidogenic Peptide from Serum Amyloid A Protein

Fragments of Serum amyloid A proteins (GenBank Accession No. gi:134167) were found in amyloid-state in cases of Chronic inflammation amyloidosis [Westermark et al. (1992) Biochem. Biophys. Res. Commun. 182: 27-33]. Based on the proposed role of aromatic residues in amyloid self-assembly, the amyloidogenic features of a Serum amyloid A protein-derived peptide, SFFSFL (SEQ ID NO: 33) were studied.

Materials and Experimental Procedures—Described in Examples 7 and 10.

Results—To characterize the ability of the Serum amyloid A protein-derived peptide to form fibrillar supramolecular ultrastructures, negative staining electron microscopy analysis was effected. As shown in FIG. 26, under mild conditions, filamentous structures were observed for the selected peptide, suggesting that SFFSFL of serum amyloid A protein is important for the polypeptide self-assembly. These results further substantiate the ability of the present invention to predict amyloidogenic peptide sequences.

Example 24

Identification of an Amyloidogenic Peptide from BriL

The human BRI gene is located on chromosome 13. The amyloid fibrils of the BriL gene product (GenBank Accession No. gi: 12643343) are associated with neuronal dysfunction and dementia (Vidal et al (1999) Nature 399, 776-781). Based on the proposed role of aromatic residues in amyloid self-assembly, the amyloidogenic features of a BriL-derived peptide, FENKF (SEQ ID NO: 34) were studied.

Materials and Experimental Procedures—Described in Examples 7 and 10.

Results—To characterize the ability of the BriL-derived peptide to form fibrillar supramolecular ultrastructures, negative staining electron microscopy analysis was effected. As shown in FIG. 27, under mild conditions, filamentous structures were observed for the selected peptide, suggesting that FENKF of BriL is important for the polypeptide self-assembly. These results further substantiate the ability of the present invention to predict amyloidogenic peptide sequences.

Example 25

Identification of an Amyloidogenic Peptide from Gelsolin

Fragments of Gelsolin proteins (GenBank Accession No. gi:4504165) were found in amyloid-state in cases of Finnish hereditary amyloidosis [Maury and Nurmiaho-Lassila (1992) Biochem. Biophys. Res. Commun. 183: 227-31]. Based on the proposed role of aromatic residues in amyloid self-assembly, the amyloidogenic features of a Gelsolin-derived peptide, SFNNG (SEQ ID NO: 35) were studied.

Materials and Experimental Procedures—Described in Examples 7 and 10.

Results—To characterize the ability of the Gelsolin-derived peptide to form fibrillar supramolecular ultrastructures, negative staining electron microscopy analysis was effected. As shown in FIG. 28, under mild conditions, filamentous structures were observed for the selected peptide, suggesting that SFNNG of BriL is important for the polypeptide self-assembly. These results further substantiate the ability of the present invention to predict amyloidogenic peptide sequences.

Example 26

Identification of an Amyloidogenic Peptide from Serum Amyloid P

Amyloid fibril formation by beta-amyloid is promoted by interaction with serum amyloid-P (GenBank Accession No. gi:2144884). Based on the proposed role of aromatic residues in amyloid self-assembly, the amyloidogenic features of a Serum amyloid P-derived peptide, LQNFTL (SEQ ID NO: 36) were studied.

Materials and Experimental Procedures—Described in Examples 7 and 10.

Results—To characterize the ability of the Serum amyloid P-derived peptide to form fibrillar supramolecular ultrastructures, negative staining electron microscopy analysis was effected. As shown in FIG. 29, under mild conditions, filamentous structures were observed for the selected peptide, suggesting that LQNFTL of Serum amyloid P is important for the polypeptide self-assembly. These results further substantiate the ability of the present invention to predict amyloidogenic peptide sequences.

Example 27

Identification of an Amyloidogenic Peptide from Immunoglobulin Light Chain

Amyloid fibrils formation by Immunoglobulin light chain (GenBank Accession No. gi:625508) is associated with primary systemic amyloidosis [Sacchettini and Kelly (2002) Nat Rev Drug Discov 1:267-75]. Based on the proposed role of aromatic residues in amyloid self-assembly, the amyloidogenic features of an Immunoglobulin light chain-derived peptide, TLIFGG (SEQ ID NO: 37) were studied.

Materials and Experimental Procedures—Described in Examples 7 and 10.

Results—To characterize the ability of the immunoglobulins light chain-derived peptide to form fibrillar supramolecular ultrastructures, negative staining electron microscopy analysis was effected. As shown in FIG. 30, under mild conditions, filamentous structures were observed for the selected peptide, suggesting that TLIFGG of the immunoglobulin light chain is important for the polypeptide self-assembly. These results further substantiate the ability of the present invention to predict amyloidogenic peptide sequences.

Example 28

Identification of an Amyloidogenic Peptide from Cystatin C

Amyloid fibril formation by Cystatin C (GenBank Accession No. gi:4490944) is associated with hereditary cerebral amyloid angiopathy [Sacchettini and Kelly (2002) Nat Rev Drug Discov 1:267-75]. Based on the proposed role of aromatic residues in amyloid self-assembly, the amyloidogenic features of a Cystatin C-derived peptide, RALDFA (SEQ ID NO: 38) were studied.

Materials and Experimental Procedures—Described in Examples 7 and 10.

Results—To characterize the ability of the Cystatin C-derived peptide to form fibrillar supramolecular ultrastructures, negative staining electron microscopy analysis was effected. As shown in FIG. 31, under mild conditions, filamentous structures were observed for the selected peptide, suggesting that RALDFA of the Cystatin C is important for the polypeptide self-assembly. These results further substantiate the ability of the present invention to predict amyloidogenic peptide sequences.

Example 29

Identification of an Amyloidogenic Peptide from Transthyretin

Amyloid fibril formation by Transthyretin (GenBank Accession No. gi:72095) is associated with familial amyloid polyneuropathy (Sacchettini and Kelly (2002) Nat Rev Drug Discov 1:267-75). Based on the proposed role of aromatic residues in amyloid self-assembly, the amyloidogenic features of an Transthyretin-derived peptide, GLVFVS (SEQ ID NO: 39) were studied.

Materials and Experimental Procedures—Described in Examples 7 and 10.

Results—To characterize the ability of the Transthyretin-derived peptide to form fibrillar supramolecular ultrastructures, negative staining electron microscopy analysis was effected. As shown in FIG. 32, under mild conditions, filamentous structures were observed for the selected peptide, suggesting that GLVFVS of Transthyretin is important for the polypeptide self-assembly. These results further substantiate the ability of the present invention to predict amyloidogenic peptide sequences.

Example 30

Identification of an Amyloidogenic Peptide from Lysozyme

Amyloid fibril formation by Lysozyme (GenBank Accession No. gi:299033) is associated with familial non-neuropathic amyloidosis [Sacchettini and Kelly (2002) Nat Rev Drug Discov 1:267-75]. Based on the proposed role of aromatic residues in amyloid self-assembly, the amyloidogenic features of a Lysozyme-derived peptide, GTFQIN (SEQ ID NO: 40) were studied.

Materials and Experimental Procedures—Described in Examples 7 and 10.

Results—To characterize the ability of the Lysozyme-derived peptide to form fibrillar supramolecular ultrastructures, negative staining electron microscopy analysis was effected. As shown in FIG. 33, under mild conditions, filamentous structures were observed for the selected peptide, suggesting that GTFQIN of Lysozyme is important for the polypeptide self-assembly. These results further substantiate the ability of the present invention to predict amyloidogenic peptide sequences.

Example 31

Identification of an Amyloidogenic Peptide from Fibrinogen

Amyloid fibril formation by Fibrinogen (GenBank Accession No. gi:11761629) is associated with hereditary renal amyloidosis (Sacchettini and Kelly (2002) Nat Rev Drug Discov 1:267-75). Based on the proposed role of aromatic residues in amyloid self-assembly, the amyloidogenic features of a Fibrinogen-derived peptide, SGIFTN (SEQ ID NO: 41) were studied.

Materials and Experimental Procedures—Described in Examples 7 and 10.

Results—To characterize the ability of the Fibrinogen-derived peptide to form fibrillar supramolecular ultrastructures, negative staining electron microscopy analysis was effected. As shown in FIG. 34, under mild conditions, filamentous structures were observed for the selected peptide, suggesting that SGIFTN of Fibrinogen is important for the polypeptide self-assembly. These results further substantiate the ability of the present invention to predict amyloidogenic peptide sequences.

Example 32

Identification of an Amyloidogenic Peptide from Insulin

Amyloid fibril formation by Insulin (GenBank Accession No. gi:229122) is associated with injection-localized amyloidosis [Sacchettini and Kelly (2002) Nat Rev Drug Discov 1:267-75]. Based on the proposed role of aromatic residues in amyloid self-assembly, the amyloidogenic features of an insulin-derived peptide, ERGFF (SEQ ID NO: 42) were studied.

Materials and Experimental Procedures—Described in Examples 7 and 10.

Results—To characterize the ability of the Insulin-derived peptide to form fibrillar supramolecular ultrastructures, negative staining electron microscopy analysis was effected. As shown in FIG. 35, under mild conditions, filamentous structures were observed for the selected peptide, suggesting that ERGFF of insulin is important for the polypeptide self-assembly. These results further substantiate the ability of the present invention to predict amyloidogenic peptide sequences.

Example 33

Identification of an Amyloidogenic Peptide from Prolactin

Amyloid fibrils formation by prolactin (GenBank Accession No. gi:4506105) is associated with pituitary-gland amyloidosis (Sacchettini and Kelly (2002) Nat Rev Drug Discov 1:267-75). Based on the proposed role of aromatic residues in amyloid self-assembly, the amyloidogenic features of a prolactin-derived peptide, RDFLDR (SEQ ID NO: 43) were studied.

Materials and Experimental Procedures—Described in Examples 7 and 10.

Results—To characterize the ability of the prolactin-derived peptide to form fibrillar supramolecular ultrastructures, negative staining electron microscopy analysis was effected. As shown in FIG. 36, under mild conditions, filamentous structures were observed for the selected peptide, suggesting that RDFLDR of prolactin is important for the polypeptide self-assembly. These results further substantiate the ability of the present invention to predict amyloidogenic peptide sequences.

Example 34

Identification of an Amyloidogenic Peptide from Beta-2-Microglobulin

Amyloid fibrils formation by beta-2-microtublin (GenBank Accession No. gi:70065) is associated haemodialysis-related amyloidosis (Sacchettini and Kelly (2002) Nat Rev Drug Discov 1:267-75). Based on the proposed role of aromatic residues in amyloid self-assembly, the amyloidogenic features of a beta-2-microtublin-derived peptide, SNFLN (SEQ ID NO: 44) were studied.

Materials and Experimental Procedures—Described in Examples 7 and 10.

Results—To characterize the ability of the beta-2-microtublin-derived peptide to form fibrillar supramolecular ultrastructures, negative staining electron microscopy analysis was effected. As shown in FIG. 37, under mild conditions, filamentous structures were observed for the selected peptide, suggesting that SNFLN of beta-2-microtublin is important for the polypeptide self-assembly. These results further substantiate the ability of the present invention to predict amyloidogenic peptide sequences.

Example 35

Inhibition of Amyloid Formation an Amyloidogenic Peptide Identified According to the Teachings of the Present Invention The ability of amyloidogenic peptides of IAPP, identified according to the teachings of the present invention to inhibit amyloid formation by the full-length polypeptide was tested by the addition of beta-breaker proline residues to the recognition sequence as set forth in the peptide sequence NFLVHPP (SEQ ID NO: 45). The degree of amyloid fibrils formation with and without the inhibitor was assessed using Thioflavin T (ThT) as molecular indicator. The degree of fluorescence of the ThT dye is directly correlated with the amount of amyloid fibrils in the solution [LeVine H 3rd. (1993) Protein Sci. 2:404-410. IAPP solutions (hIAPPin 10 mM Tris buffer pH 7.2), were incubated in the presence or absence of 40 of the modified peptide (i.e., NFLVHPP) at room temperature. Fibril formation was determined by a ten fold dilution of the solutions into a solution that contained 3 thioflavin T (ThT) in 50 mM sodium phosphate pH 6.0 and determination of fluorescence at 480 nm with excitation at 450 nm using a LS50B spectroflurimeter (Perkin Elmar, Wellesley, Mass.). As a control 10 mM Tris buffer pH 7.2 were diluted into the ThT solution and fluorescence was determined as described.

Result—As shown in FIG. 38, while the IAPP alone showed high levels of ThT fluorescence as expected for amyloidogenic protein, there was a significant increase in fluorescence in the presence of the inhibitory peptide. Thus, these results validate the NFLVH sequence as the amyloidogenic determinant in the IAPP polypeptide.

Example 36

Significance of Hydrophobic Residues in Amyloid Assembly

The significance of an aromatic residue in the basic amyloidogenic unit of IAPP has been demonstrated in Examples 1-5. As described, substitution of a phenylalanine to an alanine abolished the ability of an amyloidogenic fragment (NAGAIL, SEQ ID NO: 9) to form amyloid fibrils in vitro. Based on this observation, the remarkable occurrence of aromatic residues in other short amyloid related sequences (Examples 12-35), and the well-known role of π-stacking in processes of self-assembly in chemistry and biochemistry, it was suggested that stacking of aromatic residues may play a role in the process of amyloid fibrils formation [Gazit (2002) FASEB J. 16:77-83].

The study was further extended to indicate whether the phenylalanine residue is critical due to aromaticity thereof, or rather due to its hydrophobic nature. The effect of phenylalanine substitution with hydrophobic residues on the self assembly of the basic amyloidogenic unit of IAPP (i.e., NFGAIL peptide) was addressed.

The list of peptides used in the study and designation thereof is presented in Table 6, below.

TABLE 6

| Amino acid substitution and coordinates on hIAPP | Peptide sequence | SEQ ID NO: |
|---|---|---|
| WT 22-29 | NH$_2$-NFGAILSS-COOH | 46 |
| F > I 22-29 | NH$_2$-NIGAILSS-COOH | 47 |
| F > L 22-29 | NH$_2$-NLGAILSS-COOH | 48 |
| F > V 22-29 | NH$_2$-NVGAILSS-COOH | 49 |
| F > A 22-29 | NH$_2$-NAGAILSS-COOH | 89 |

It will be appreciated that while these hydrophobic amino acids are similar or even slightly more hydrophobic than phenylalanine [Wolfenden (1981) Biochemistry 20:849-855; Kyte (1982) J. Mol. Biol. 157:105-132; Radzicka (1988)], they are not aromatic. Furthermore, valine and isoleucine, are considered to be very strong β-sheet formers [Chou (1974) Biochemistry 13:211-222; Chou (1978) Annu. Rev. Biochem. 47:251-276], which is assumed to be important to the formation of β-sheet rich amyloid fibrils.

Example 37

Characterization of the Aggregation Kinetics of Hydrophobically Modified hIAPP Peptide Fragments as Monitored by Turbidity Measurements Experimental Procedures—Effected as described in Example 8.

Results

To get insight into the aggregation potential of the hydrophobically-modified IAPP-derived peptide analogues, turbidity assay was performed. Freshly made stock solutions of the wild-type peptide and the various peptide mutants were made in DMSO. The peptides were then diluted to a buffer solution and the turbidity was monitored by following the absorbance at 405 nm as a function of time. As shown in FIG. 39, significant increase in turbidity was observed for the wild-type NFGAILSS octapeptide within minutes following dilution thereof into the aqueous solution. The shape of the aggregation curve resembled that of a saturation curve, with a rapid increase in turbidity in the first hour, followed by a much slower increase in turbidity over the entire incubation time monitored. This probably reflects a rapid aggregation process, with the number of free building blocks as the rate limiting factor. In contrast, none of the analogue peptides revealed any significant aggregative behavior and the turbidity of all the hydrophobic analogues as well as the alanine-substituted analogues remained very low for at least 24 hours (FIG. 39).

To determine whether the non-aggregative behavior of the hydrophobic analogues is a result of extremely slow kinetics, peptide analogue solutions were incubated for 1 week in the same experimental conditions and endpoint turbidity values were determined. As shown in FIG. 30, some low degree of turbidity was observed with the NIGAILSS, and lower extent for the NLGAILSS, NAGAILSS, and NVGAILSS peptides in decreasing order of turbidity. However, even for the NIGAILSS, the degree of turbidity was significantly lower as compared to the wild-type NFGAILSS protein (FIG. 40). Moreover, there was no correlation between aggregation potential and hydrophobicity or β-sheet forming tendency, since the lower degree of aggregation was observed with the substitution to the highly hydrophobic and β-sheet former, valine. The slight decrease in the endpoint turbidity value of the NFGAILSS wild-type peptide, as compared to the values obtained after 24 hours incubation, could reflect the formation of very large aggregates that adhere to the cuvette surface.

Example 38

Ultrastructural Analysis of Hydrophobically Modified hIAPP Peptide Fragments Electron microscopy analysis was effected as described in Example 10.

Figure 41A:
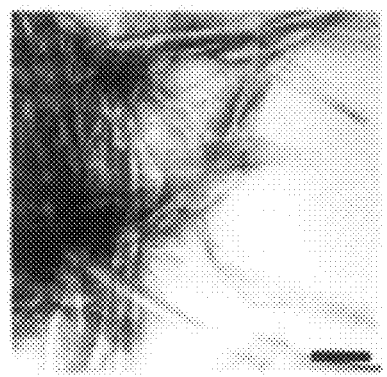
Figure 41B:
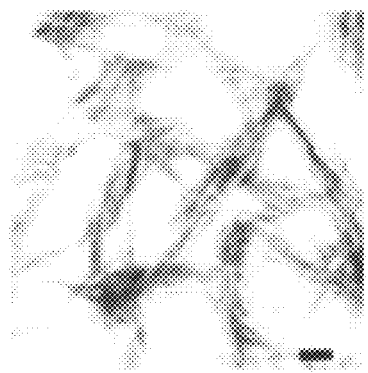
Figure 41C:
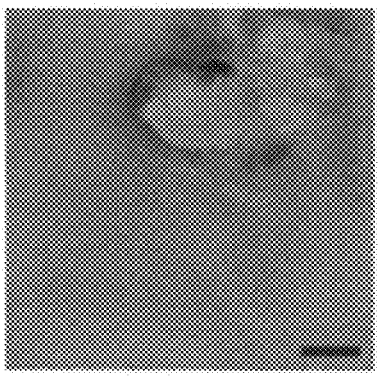
Figure 41D:
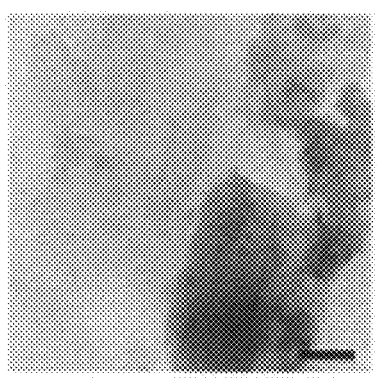
Figure 41E:
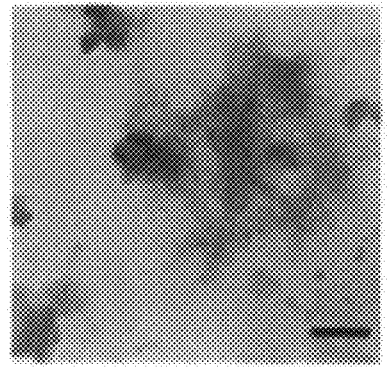
Figure 41F:
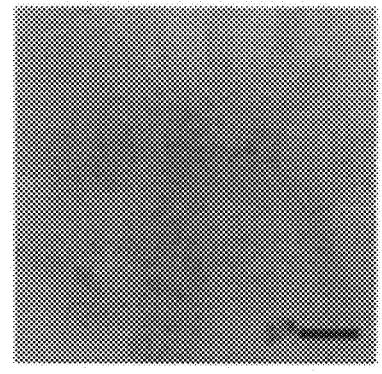

An ultrastructural visualization of any possible structures formed by the various analogous peptides was effected following five days of incubation. This structural analysis represents the most sensitive method since various aggregates were visualized individually. For that aim, the occurrence and characteristics of the formed structures were studied by electron microscopy using negative staining, with the same of peptide solution which were incubated in the aggregation assay (Example 32). As expected, well-ordered fibrils were observed with the wild-type peptide NFGAILSS peptide fragment (FIGS. 41a-b). Some amorphous aggregates could be also seen with the modified fragments (FIGS. 41c-f). However, those structures were significantly less abundant on the microscope grid. Larger aggregative structures were observed with the more hydrophobic substitutions as compared to the alanine analogues. Yet, unlike the ordered fibrillar structures that were seen with the NFGAILSS peptide, as mentioned above, these aggregates were quite rare and did not have ordered structures (FIGS. 41c-f). Those irregular and sporadic structures are consistent with some degree of non-specific aggregation as expected after long incubation of rather hydrophobic molecules.

Example 39

Determination of the Specific Function of Phenylalanine in the IAPP Self Assembly To determine the specific role of the phenylalanine residue in IAPP-self assembly, a membrane-based binding assay was preformed in order to systematically explore the molecular determinants that facilitate the ability of the full-length hIAPP to recognize the "basic amyloidogenic unit". To this end, the ability of MBP-IAPP (see Example 6) to interact with an array of peptides in which the phenylalanine position was systematically altered (SEQ ID NOs. 91-110), was addressed.

Materials and Experimental Procedures—See Examples 6-7.

Results

A peptide array corresponding to the SNNXGAILSS motif (SEQ ID NO: 90), where X is any natural amino-acid but cysteine was constructed. As shown in FIG. 42a, binding of MBP-IAPP was clearly observed to peptides which contained the aromatic tryptophan and phenylalanine residues at the X position (FIG. 42a). Interestingly, binding was also observed upon substitution of phenylalanine with basic amino acids such as arginine and lysine. In contrast, no binding was observed with any of the hydrophobic substitutions of the position, even after long exposure of the membrane (FIG. 42b).

The short exposure binding was assessed using densitometry (FIG. 42c). It will be appreciated though, that the measured binding should be interpreted as semiquantitative since the coupling efficiency during synthesis and therefore the amount of peptide per spot may vary. In this case, however, the marked difference in binding between the various peptide variants was very clear.

Taken together, all these observations substantiate the role of aromatic residues in the acceleration of amyloid formation processes.

Example 40

Design and Configuration of α-Aminoisobutyric Acid (Aib) Substituted Amyloid Forming Peptides The minimal amyloid forming region of IAPP polypeptide (i.e., IAPP 14-20, see Table 3 above) was selected as the target sequence for designing inhibitors which are able to bind thereto, block it and prevent aggregation thereof.

Experimental Approach

To abolish the aggregation ability of amyloid forming peptides, β-sheet breakers are incorporated into the target sequence, such that the peptides cannot display a β-sheet conformation by which the monomers are stacked together to form fibrils. α-aminoisobutyric acid (Aib) is an unnatural amino acid which contains two methyl residues attached to $C_\alpha$ of the carboxylic group. Unlike natural amino acids, this molecule does not have a hydrogen atom attached to the $C_\alpha$. This affects widely the sterical properties of the amino acid especially with respect to the φ and ψ angels of the amide bond. While alanine has a wide range of allowed φ and ψ conformations, Aib, which is a α-methylated alanine has limited φ and ψ conformations. FIG. 43a shows the conformational map of Aib derived from the superposition of the Ramachandran plots of L-alanine and D-alanine. As is evident for FIG. 43a, the allowed angels are limited to small regions and the overall structure is much more suitable for an α-helix conformation rather than a β-strand conformation.

Hence, Aib can be used to prevent β-sheet conformation which is central to amyloid aggregation. Notably, a comparison between the Ramachandran plots of Aib and proline shows that Aib is a more potent β-sheet breaker than proline (FIG. 43a).

Two peptides including IAPP amyloid forming regions (i.e., ANFLVH and ANFLV, SEQ ID NOs: 124 and 126, respectively) were synthesized to include Aib substituting the alanine and the leucine residues. The newly synthesized peptides included the following amino acid sequences Aib-NF-Aib-VH (SEQ ID NO: 125-) and Aib-NF-Aib-V (SEQ ID NO: 127) wild type ANFLVH and the synthesized Aib-NF-Aib-VH are illustrated in FIGS. 43b and c respectively.

Peptides Synthesis—Peptides were synthesized by Peptron, Inc. (Taejeon, Korea) using solid-phase techniques. The correct identity of the peptides was confirmed by ion spray mass-spectrometry using a HP 1100 series LC/MSD. The purity of the peptides was confirmed by reverse phase high-pressure liquid chromatography (RP-HPLC) on a $C_{18}$ column, using a 30 minutes linear gradient of 0 to 100% acetonitrile in water and 0.1% trifluoroacetic acid (TFA) at flow rate of 1 ml/min.

Peptide solutions—freshly prepared stock solutions were prepared by dissolving the lyophilized form of the peptides in dimethyl sulfoxide (DMSO) at a concentration of 100 mM. To avoid any pre-aggregation, fresh stock solutions were prepared for each experiment. Peptide stock solutions were diluted into microtubes as follows: 5 μL of peptides stock solutions added to 95 μL of 10 mM Tris, pH 7.2 (hence the final concentration of the peptide was 5 mM in the presence of 5% DMSO).

Example 41

Ultrastructural Analysis of Wild-Type and Aib Modified hIAPP Peptides

The fibrillogenic potential of the peptides described in Example 40 above, was assessed by electron microscopy analysis.

Materials and Experimental Procedures

Transmission Electron Microscopy—a 10 μL sample of 5 mM peptide solution in 10 mM Tris buffer, pH 7.2 aged for 4 days (for wt peptides) and for 10 days (for modified peptides) was placed on 400-mesh copper grids (SPI supplies, West Chester Pa.) covered by carbon-stabilized Formvar film. After 1 minute, excess fluid was removed, and the grid was then negatively stained with 2% uranyl acetate in water for another 2 minutes. Samples were viewed in a JEOL 1200EX electron microscope operating at 80 kV.

Results

The ability of Aib containing peptides to form amyloid fibrils was examined in comparison to native IAPP peptides. Aged solutions of the Aib-modified and wild-type peptides were examined under electronic microscope (EM) using negative staining. As is shown in FIGS. 44a-b, both native peptides, ANFLVH (FIG. 44a) and ANFLV (FIG. 44b), formed fibrillar structures with high resemblance to the fibrils formed by the full-length IAPP protein. On the other hand, no fibrillar structures were evident for the Aib containing peptides, Aib-NF-Aib-VH (FIG. 44c) and Aib-NF-Aib-V (FIG. 44d), even after longer periods of incubation, while amorphous aggregates were still evident, suggesting that the Aib substituted peptides of the present invention are incapable of fibril formation.

Example 42

Examination of the Amyloidogenic Properties of Wild-Type and Aib Substituted IAPP Peptides by Congo Red Binding Assay Materials and Experimental Procedures Congo Red Staining and Birefringence—A 10 μL suspension of 5 mM peptide solution in 10 mM Tris buffer, pH 7.2 aged for 10 days was allowed to dry overnight on a glass microscope slide. Staining was performed by the addition of a 10 μL suspension of saturated Congo Red (CR) and NaCl in 80% ethanol (v/v) solution. The solution was filtered via 0.2 μm filter. The slide was then dried for a few hours. Birefringence was determined with a SZX-12 Stereoscope (Olympus, Hamburg, Germany) equipped with cross polarizers. 100× magnification is shown.

Results

Congo red staining was used to assess the amyloidogenic properties of Aib modified peptides. Slides were examined under the microscope using cross-polarizers. FIGS. 45a-b show a typical yellow-green birefringence for both ANFLVH and ANFLV peptides (FIGS. 45a and b, respectively). However, in accordance with the EM studies, the Aib-modified peptides, Aib-NF-Aib-VH and Aib-NF-Aib-V, exhibited no birefringence suggesting that Aib modified peptides can not form amyloid fibrils (FIGS. 45c-d).

Example 43

Secondary Structure Analysis of Aib-Modified IAPP Peptide Fragments

Fourier transform infrared spectroscopy (FT-IR) was effected to determine the secondary structure of the Aib-modified hIAPP.

Materials and Experimental Procedures

Fourier Transform Infrared Spectroscopy—Infrared spectra were recorded using a Nicolet Nexus 470 FT-IR spectrometer with a DTGS detector. Samples of two week aged peptide solutions, were suspended on a $CaF_2$ plate and dried by vacuum. The peptide deposits were resuspended with $D_2O$ and subsequently dried to form thin films. The resuspension procedure was repeated twice to ensure maximal hydrogen to deuterium exchange. The measurements were taken using a 4 $cm^{-1}$ resolution and 2000 scans averaging. The transmittance minima values were determined by the OMNIC analysis program (Nicolet).

Results

FT-IR spectroscopy was used to elucidate the internal conformation of the observed structures (see Examples 42 and 43, above). As shown in FIGS. 46a-b upon incorporation of Aib, IAPP peptides displayed a sharp change in the IR spectra. Whereas the ANFLVH and ANFLV peptides spectra were typical of β-sheet spectra, with minima at 1630 $cm^{-1}$ and 1632 $cm^{-1}$ respectively, the Aib-NF-Aib-VH and Aib-NF-Aib-V peptides displayed minima at 1670 $cm^{-1}$ and 1666 $cm^{-1}$, respectively, which are characteristic to a random coil conformation.

Taken together, these results suggest a fundamental difference between the native IAPP peptide and the Aib containing peptides. Whereas the native peptides are highly amyloidogenic, the modified Aib containing peptides are not able to form amyloid fibrils (Examples 41-43).

Example 44

Aib Modified Peptides Inhibit Amyloid Formation by IAPP Polypeptide

The degree of amyloid fibril formation with and without the Aib inhibitor was assessed using thioflavin T (ThT) as molecular indicator. The degree of fluorescence of the ThT dye is directly correlated with the amount of amyloid fibrils in the solution [LeVine H 3rd. (1993) Protein Sci. 2:404410].

Materials and Experimental Procedures

Fourier Transform Infrared Spectroscopy—IAPP solutions (4 μM peptide in 10 mM Tris buffer pH 7.2), were incubated with or without 40 μM of the various peptide solutions at room temperature. Fibril formation was assessed by a ten fold diluation of the solutions into a solution which contained 3 μM thioflavin T (ThT) in 50 mM sodium phosphate pH 6.0 and determination of fluorescence at 480 nm with excitation at 450 nm using a Perkin Elmar LS50B spectroflurimeter. As a control a 10 mM Tris buffer pH 7.2 was diluted into the ThT solution and fluorescence was determined as described.

Results

As shown in FIG. 47, all Aib-modified peptides were able to inhibit the assembly of full-length IAPP polypeptide, suggesting that Aib modification of amyloid forming peptides can serve as strong inhibitory tool in various therapeutic applications.

Example 45

Di- and Tri-Aromatic Peptides can Inhibit Aggregation of IAPP Polypeptide

In order to study the ability of short aromatic amino acid sequences to inhibit the assembly of amyloid polypeptides and to address the ability of β-sheet breaker amino acids to facilitate such inhibition, an array of tetra-, tri- and dipeptides was synthesized and assayed.

Experimental Procedures

Peptide synthesis—The list of peptides used in the present and Examples 46-47, which follow and designation thereof is presented in Table 7, below. Peptide synthesis is described in Examples 46-47, which follow.

TABLE 7

| Identification | Amino acid sequence | SEQ ID NO: |
|---|---|---|
| EG01 | D-Phe-D-Phe-D-Pro | 128 |
| EG02 | Aib-D-Phe-D-Asn-Aib | 129 |
| EG03 | D-Phe-D-Asn-D-Pro | 130 |
| EG04 | Aib-Asn-Phe-Aib | 131 |
| EG05 | Gln-Lys-Leu-Val-Phe-Phe | 132 |
| EG06 | Tyr-Tyr | 133 |
| EG07 | D-Phe-D-Phe-D-Pro | 112 |
| EG08 | Aib-D-Phe-D-Asn-Aib | 113 |
| EG09 | Aib-Asn-Phe-Aib | 114 |
| EG10 | Tyr-Tyr | 115 |
| EG11 | Tyr-Tyr-NH2 | 116 |
| EG12 | Aib-Phe-Phe | 117 |
| EG13 | Asn-Tyr-Aib | 118 |
| EG14 | Asn-Tyr-Pro | 119 |
| EG15 β-aminoisobutyric acid (Aib) | D-Pro-D-Tyr-D-Asn | 120 |
| EG16 | D-Tyr-Aib | 121 |

TABLE 7-continued

| Identification | Amino acid sequence | SEQ ID NO: |
|---|---|---|
| EG17 | D-Pro-D-Tyr | 122 |
| EG18 | D-Tyr-D-Pro | 123 |
| EG19 | Asn-Tyr-Tyr-Pro | 134 |
| EG20 | Tyr-Tyr-Aib | 135 |
| EG21 | Aib-Tyr-Tyr | 136 |
| EG22 | Aib-Tyr-Tyr-Aib | 137 |
| EG23 | D-Asn-Tyr-Tyr-D-Pro | 138 |
| EG24 | Pro-Tyr-Tyr | 139 |
| EG25 | Tyr-Tyr-Pro | 140 |
| EG26 | Pro-Tyr-Tyr-Pro | 141 |
| EG27 | D-Tyr-D-Tyr | 142 |
| EG28 | D-Pro-Aib | 143 |
| EG29 | D-Phe-D-Pro | 144 |
| EG30 | D-Trp-Aib | 145 |
| EG31 | D-Trp-D-Pro | 146 |
| d-F-P | D-Phe-Pro | 147 |
| P-d-F | Pro-D-Phe | 148 |

ThT Fluorescence Assay—See Example 44 Above.

Results

The inhibitory peptides were assayed using standard ThT fluorescence assay (as described). FIG. 48 shows endpoint values after IAPP aggregation reaches a plateau, following 142 hours of incubation. The aggregation assay was preformed in the presence of IAPP polypeptide (4 µM) and the inhibitory peptides (40 µM).

As is clearly shown in FIG. 48, short aromatic amino acid sequences mediate recognition to IAPP polypeptide while inhibiting aggregation thereof. The best inhibitor was the Aib-Phe-Phe peptide (EG12) in which the Aib residue is conjugated to the shortest recognition element which can form amyloid-related structures [Reches and Gazit, Science (2003) 300(2619):625-7]. D-Tyr-D-Pro (EG18) and D-Tyr-D-Aib (EG16) displayed a significant inhibitory effect on IAPP aggregation substantiating the ability of a single aromatic residue to mediate molecular-recognition. Interestingly, Aib displayed a higher inhibitory activity than Proline. Furthermore, the significant difference in activity between peptide EG17 and EG 18 which differ in the position of the β-sheet breaker amino acid relatively to the aromatic amino acid, suggests a role for the order and not only the composition of the peptides.

Example 46

Selection of Best Performing IAPP Fibrilization Inhibitors and Criteria for Selecting Same Peptides Synthesis—Peptide synthesis (excluding EG5, EG6, and EG7, D-Phe-Pro, and D-Pro-Phe), was effected by using solid-phase synthesis (Peptron, Inc., Taejeon, Korea). Peptide identity was confirmed by ion spray mass-spectrometry. Peptide purity was confirmed by reverse phase high-pressure liquid chromatography (RP-HPLC). EG5, EG6, and EG7, D-Phe-Pro, and D-Pro-Phe were purchased from Bachem (Bubendorf, Switzerland). Islet amyloid polypeptide (IAPP) was purchased from CalBiochem (La Jolla Calif., USA).

Thioflavin T fluorescence assay—hIAPP fibrillization was monitored by Thioflavin T dye binding assay. $hIAPP_{1-37}$ stock solution was diluted to a final concentration of 4 µM in 10 mM sodium acetate buffer (pH 6.5) with or without inhibitors (40 µM), and a final concentration of HFIP of 1% (vol). Immediately after dilution, sample was centrifuged for 20 minutes in 20,000×g at 4° C. and the supernatant fraction was used for fluorescence measurements. In every measurement ThT was added to a 1 ml sample at a final concentration of 3 µM and measurements were effected by using Perkin-Elmer (excitation 450 nm, 2.5 nm slit; emission 480 nm 10 nm slit). Background was subtracted from all samples.

Results

Identification of potent inhibitors and rules for inhibitor design—In order to identify small peptide inhibitors of IAPP fibrillization and to optimize a minimal length of the inhibitors and maximal stability thereof, iterative cycles of peptide selection were effected using D-amino acids analogues.

The first round of selection shown in FIG. 49*a* demonstrated that peptides as short as tripeptides can efficiently inhibit the formation of amyloid by IAPP. Comparison of EG01 and EG03 suggests that presence of Asn residue within the short peptide does not contribute to the inhibition of amyloid formation and further supports the use of aromatic moieties along with beta-breakers for optimal inhibition. The effective inhibition of IAPP fibrillization by EG05, a known inhibitor of amyloid formation [Tjernberg et al. (1996) J. Biol. Chem. 271: 8545-854], suggests a generic inhibition of amyloid formation by aromatic residues. Indeed, the similar activity of the EG05 and the much shorter EG08 (Aib conjugated to the Phe-Phe) element clearly suggest that the generic inhibition of EG05 stems from its aromatic nature.

The second round of selection shown in FIG. 49*b* demonstrated that effective inhibition could be achieved not only by tripeptide but also by dipeptides (EG16, EG17, EG18). In all cases the conjugation of a D-isomer to an aromatic moiety was used. The difference between EG16 and EG17 was further studied in the next round to establish rules for the design of inhibitors. FIG. 49*c* shows the results of a third round of selection. The comparison in the third round (FIG. 49*c*) of EG20 vs. EG21 (d-F-P vs. P-d-F) along with the results obtained by comparing EG16 and EG17 in the second round, and the results obtained by comparing EG24 and EG35 (in the forth round—FIG. 1*d*), suggest a general formula for the design of dipeptide inhibitors as set forth in: (Aromatic D or L)-(beta-breaker). These selection steps further provided a general formula for tripeptide inhibitors as set forth in: (Aromatic D or L)-(Aromatic D or L)-(beta-breaker).

The forth round also demonstrated the inhibition potential of four putauvely metabolically stable dipeptides EG28, EG29, EG30, EG31. Again, stressing the value of beta-breakers and aromatic amino acids for the inhibitory sequences.

Example 47

Inhibition of β-Amyloid Polypeptide Fibril Formation by D-Trp-Aib

Peptides Synthesis—See Example 46 above. Recombinant β-amyloid (Aβ 1-40,>98% pure) was purchase from rPeptide (Athens Ga., USA).

Thioflavin T fluorescence assay—Fibrillization of Aβ 1-40 was monitored by Thioflavin T dye binding assay. AP 1-40 stock solution was diluted to a final concentration of 5 µM in 100 mM NaCl, 10 mM sodium phosphate buffer (pH 7.4) with or without inhibitors. In every measurement ThT was added to 0.1 ml sample to a final concentration of 0.3 µM ThT and 0.4 µM polypeptide. Measurements were effected using Jobin Yvon FluroMax-3 (excitation 450 nm, 2.5 nm slit; emission 480 nm 5 nm slit, integration time 1 second). Background was subtracted from all samples.

Transmission Electron Microscopy—10 µL samples were placed on 400-mesh copper grids (SPI supplies, West Chester Pa.) covered with carbon-stabilized Formvar film. Following 1 minute, excess fluid was removed, and the grids were negatively stained with 2% uranyl acetate in water for another two minutes. Samples were viewed by a JEOL 1200EX electron microscope operating at 80 kV.

Results

Fluorescence measurements of inhibition—To test whether the D-Trp-Aib can inhibit amyloid formation by molecules other than IAPP, Alzheimer's β-amyloid 1-40 (Aβ) was served as a model system. As shown in FIG. 50, in the absence of inhibitor, Aβ displayed a lag phase in fibrilization of about 100 hours which was followed by a fast enhancement in fluorescent levels. In the presence of 10 µM of D-Trp-Aib, the lag time was significantly increased and the overall fluorescence upon reaching a plateau was significantly lower than that observed without the inhibitor.

This further suggests that aromatic inhibitors may serve as generic amyloid inhibitors and a common mechanism of assembly [Gazit (2002) FASEB J. 16, 77-83].

Ultrastructural analysis—To get information on the mechanism of inhibition, samples taken from the fluorescence assay upon its termination assay were viewed by electron microscopy (FIG. 51a-c). Distinct and well-defined amyloid fibers were present in samples of Aβ not including the inhibitor (FIG. 51a). In contrast, in the presence of D-Trp-Aib, Aβ was detected mostly as amorphous aggregates (FIG. 51b) or as fragmented fibrils (FIG. 51c). This suggests that even those fibrils generated in the presence of the inhibitor were short and probably dysfunctional.

Thus, the D-Trp-Aib (also termed EG30; SEQ ID NO: 145) compound offers a unique combination of pharmaceutical properties in an extremely small molecule:

1. Hetero-aromatic interactions: The interaction between the tryptophan indole and the aromatic recognition interfaces of the growing amyloid fibrils (Gazit, 2002) allows specific and oriented binding that directly and precisely blocks further homo-molecular self-assembly of the growing chain.

2. The Aib conformational restriction: The conjugation of the β-aminoisobutyric acid (Aib), an amino acid with exceptional geometrical constrain, induce a very strong β-sheet breakage effect, a key measure to halt the growing of amyloid fibrils. This β-breakage strategy shows a clear advantage as compared to prior art (proline introduction) in terms of size and complexity of the molecule.

3. A stable D-isomer conformation: The inhibitor is built of a D-amino acid and a non-chiral Aib moiety. This results in the formation of a non-cleavable peptide bond and thus with a presumably high physiological stability.

4. Peptide bond stacking: In spite of its small size, a typical peptide bond (although isomerically stable one) is retained within the molecule. The unique planar characteristic of such a peptide bond allows a specific and geometrically-constrained stacking of the molecule on the growing amyloid chain, due to their partially planar resonating structures with the exact geometry that is consistent with β-strand interaction.

5. Electrostatic repulsion: The existence of charged terimi results in electrostatic repulsion of further binding monomers. Such repulsion is achieved by introduction of a charged aspartic acid in other peptide inhibitors [Soto et al. (2003) J. Biol. Chem 278:13905] as there is a need to block the termini of these peptides to decrease proteolytic degradation. The non-native stable isomeric configuration of the D-Trp-Aib allows the retention of charged termini within the minimal framework resulting in a significantly small molecule.

6. Bulky hydrophobic moiety: The trypotophan indole group offers a unique bulkiness and hydrophobic nature in a very small molecular system. It is well established that tryptophan moieties have among the highest membrane partition coefficients. It is speculated that this property should have a key advantage for oral bioavailability and blood brain barrier (BBB) transfer.

7. Antioxidant activity: The indole group is also known to act as antioxidant by the scavenging of free-radicals. Indeed, some of the drug candidates for treating AD are based on this property (e.g. indole-3-propionic acid of MindSet). However, while such molecules are effective in the protection of neural cells from AD related oxidation stress, they lack the unique fibrillization inhibitory properties of the D-Trp-Aib molecular frame.

8. Small size: D-Trp-Aib is a remarkably small active molecule. All the unique properties that were described in the previous paragraphs (1-7) are maintained within a molecule of less than 300 Da. The small size of this non-cleavable molecule suggests an oral bioavailability, long half-life, and transfer of the BBB, while maintaining low immunogenic potential.

Example 48

Interaction of D-Trp-Aib with Early Amyloid Intermediates and Inhibition of β-Amyloid Globuolmer Formation by D-Trp-Aib To study the ability of D-Trp-Aib to bind early amyloid intermediates and inhibit globulomer formation, β-amyloid$_{1-42}$ (Aβ$_{1-42}$) intermediates and globulomers were produced in the presence of D-Trp-Aib.

Experimental Procedures

Aggregation of Aβ-amyloid$_{1-42}$—Synthetic A$_{1-42}$ β (Bachem, Bubendorf Switzerland) was freshly dissolved from the lyophilized powder in DMSO at a concentration of 100 µM. To avoid pre-aggregation, fresh stock solutions were sonicated for 1 min and prepared before each experiment. The stock solutions were diluted in phosphate-buffered saline (10 mM PBS, 100 mM NaCl, 0.5 mM EDTA, pH 7.4) to a concentration of 10 µM. To generate inhibitor stock solutions, the indicated inhibitors were dissolved in DMSO at a concentration of 20 mM. These inhibitor stock solutions were diluted in PBS to the indicated concentrations. For interaction with the inhibitor, β-amyloid monomers (0.4 mM) were produced by dissolving the 1-42 peptide in 1,1,1,3,3,3-hexafluoroisopropanol (HFIP), and were incubated in the presence of different concentrations of D-Trp-Aib (1:2, 1:10, and 1:20 β-amyloid and D-Trp-Aib molar ratio, or β-amyloid alone), at 37° C. for 6 hours, according to Barghorn et al. [Journal of Neurochemistry. 95, 834-847(2005)]. β amyloid intermediates were then separated using a 15% Tris-Tricine gel, and transferred to a PVDF membrane, which was screened with mouse anti-β-amyloid monoclonal antibody (6E10) [Jung S S et al. *Neurobiol Aging* 20:249-57 (1999)].

Globulomer production—β-amyloid monomers (0.13 mM) were incubated with different concentrations of D-Trp-Aib (1:5, 1:10, and 1:20 β-amyloid and D-Trp-Aib molar ratio, or β-amyloid alone) at 37° C. for 24 hours. Solutions were then separated using a 15% Tris-Tricine gel, and transferred to a PVDF membrane, which was screened with a mouse anti β-amyloid monoclonal antibody (6E10; Signet, Dedham, Mass.)

Results

Formation of a D-Trp-Aib-amyloid complex—The addition of D-Trp-Aib to forming β-amyloid$_{1-42}$ intermediates slightly increased the molecular weight of the intermediates compared to the control, and appeared as a higher band in the gel (FIG. 52). This band shift indicates the presence of a D-Trp-Aib-amyloid complex, formed already at this early stage of aggregation.

D-Trp-Aib blocks globulomer formation—β-amyloid$_{1-42}$ were allowed to form globulomers in the presence of different concentrations of D-Trp-Aib. Since no globulomers could be detected after 6 hour of β-amyloid incubation, the solution was incubated for 18 hours at 37° C. Western blot results showed a decrease in the band intensity of globulomers in the presence of increasing concentrations of D-Trp-Aib (FIG. 53*a*). Moreover, densitometer analysis (FIG. 53*b*) demonstrated a dose-dependent inhibition, evidenced by a decrease in the amount of globulomers to about 45% of the control. Altogether these results further suggest that D-Trp-Aib may serve as a potent and generic amyloid inhibitor.

Example 49

D-Trp-Aib Inhibits the Cytotoxic Effect of Amyloid in Cell Cultures (In Vitro)

Efficacy of D-Trp-Aib as an inhibitor of amyloid toxicity was evaluated in cell cultures using the MTT cell viability assay Experimental Procedures Incubation of PC-12 cells with β-amyloids and the inhibitor—PC-12 cells (ATCC Accession no: CRL-1721) were grown in 96 well plates in the presence of 5 μM Aβ$_{1-40}$, with growing concentrations (6.5 μM-150 μM as indicated in FIG. 54, or without) D-Trp-Aib, for 24 hr at 37° C. Prior to incubation with the PC-12 cells, 5 X concentrated Aβ$_{1-40}$ (25 μM) and 5× concentrated D-Trp-Aib were pre-incubated for 21 days.

Aggregation of β-amyloids in the presence of the inhibitor—preparation of β-amyloids and inhibitor was conducted as described in Example 48

Incubation of neuronal cells with β-amyloids and the inhibitor—One-day-old fertilized Lohman Brown chicken eggs were purchased from a local chicken breeder (Schropper Geflügel GmbH, Austria) and kept at 12° C. and 80% humidity. At embryonic day 0 eggs were transferred into a breeding incubator and stored under permanent turning at 37.8° C. and 55% humidity, until embryonic day 8, at which the embryos reach a specific developmental stage, when the brain almost exclusively contains nerve cells and less than 5% Glia [Pettmann, B., et al., Nature 281:378-380 (1979)]. Thereafter, neurons were isolated from 4 to 8 chicken embryos per experiment. Isolated cells were then lesioned with 15 μM β-amyloid$_{1-42}$. Prior to incubation, β-amyloids were incubated with D-Trp-Aib (50 μM) or with vehicle (bi-distilled water), for 7 days. Effects of D-Trp-Aib, as compared to control, on β-amyloid$_{1-42}$ lesion were evaluated on day 10 by MTT to establish cell viability (see below).

Cell viability—The MTT-assay is a very sensitive assay measuring the mitochondrial dehydrogenase activity in viable cells. Following incubation, MTT reduction assay was undertaken according to the method described by Mosmann, [J. Immunol. Meth, 55-63 (1983)], cell viability was calculated by subtracting Aβ$_{1-40}$ samples absorbance from non-Aβ$_{1-40}$ controls containing the same D-Trp-Aib concentrations.

Results

Inhibition of amyloid cytotoxicity by D-Trp-Aib in PC-12 cells—D-Trp-Aib was found to be highly effective in inhibiting the cytotoxicity of β-amyloid towards PC-12 cells in culture. The inhibition is dose responsive at the low micro molar range (FIG. 54).

Inhibition of amyloid cytotoxicity by D-Trp-Aib in primary neuronal cells—D-Trp-Aib was found to be highly potent in counteracting the neurotoxic effect of β-amyloid towards primary cultures of neuronal cells (FIG. 55).

Given together, the present results show that D-Trp-Aib clearly inhibits the cyctotoxic effect of beta amyloid both in cell lines and in primary cultures supporting its use as an in vivo inhibitor of amyloid mediated cytotoxicity.

Example 50

Efficacy of D-Trp-Aib Inhibition of Amyloid Cytotoxicity in hAPP (751) Transgenic Mice (In Vivo)

The efficacy of D-Trp-Aib in reducing brain β-amyloid aggregation and consequent cognitive decline was evaluated in β-amyloid overexpressing transgenic mice, as a model of Alzheimer's disease.

Materials and Experimental Procedures

Animal Model—hAPP (751) transgenic (tg) mice express the human β-amyloid Swedish double mutations (K670M/N671L) and the London mutation (V7171). Over-expression of the mutated genes results in the development of typical β-amyloid deposits in the form of amyloid plaques in the animals' neocortex and hippocampus. Amyloid deposition is detectable as early as 3-6 months of age. The hAPP (751) tg animals also exhibit clearly impaired learning and memory as early as 6 months. Moreover, there is a correlation between the increasing learning deficits and the increasing plaque load (Source—JSW Research).

Study design—Animals 4.5 months of age were treated with D-Trp-Aib for 4 months at which time β-amyloid deposition and learning deficits were evaluated.

Experimental design—20 (+3 reserves) 4.5 month (±1 week) old male hAPP (751) transgenic mice were divided into 2 treatment groups, a control group—treated with vehicle and an experimental group—treated with D-Trp-Aib. Animals were treated for 120 days with 3 intraperitoneal (i.p.) injections of 1 mg per animal per day. 7 of the original 20 animals died during the 4-month experimental period, 4 of them from the control group.

Cognitive performance test—4 months treated, 8-9 month old hAPP tg mice were evaluated for cognitive abilities. Cognitive performance was evaluated by the hippocampus dependent spatial navigation task, the Morris water maze test (MWM). This task was carried out in a circular pool (1m diameter) filled with constantly controlled 22±1° C. warm, clear water. The pool was virtually divided into four quadrants, in one of which (the southwest of the pool), a diaphanous—for an animal invisible—platform was placed 1 cm beneath the surface of the water. Within each 60 second trial, a mouse was allowed to reach the platform. During the experiments the location of the platform in the pool was not changed, however, the starting point to place a mouse in the pool randomly changed. For each trial, the escape latency (seconds to reach the platform) and the length of swimming path (way in meters to reach the platform; length) were measured. Trials were performed for 4 consecutive days, where each animal performed 3 training trials, with a 10-minute interval between trials.

Evaluation of β-amyloid assembly—β amyloid aggregation and deposition in the cortex and hippocampus was effected by immunohistochemical evaluation of plaque load using the monoclonal Anti-β amyloid-antibody 6E10 (Signet, Dedham, Mass.) with secondary Cy3 (Chemicon International Inc. Temecula, Calif.) as well as ThioflavinS staining for evaluation of beta-sheet structures in the plaques. Soluble and insoluble (formic-acid requiring) β-amyloid deposition was determined in the cerebrospinal fluid and in four brain fractions. For the evaluation of plaque load, brain region areas, number, size and area of plaques were measured and counted with ImageProPlus software (Version 4.5.1.29).

Results

D-Trp-Aib had a beneficial effect on cognitive impairment as measured by the MWW test—Significant differences in spatial navigation as depicted both in swimming distance and in time of escape were observed between the D-Trp-Aib and vehicle-treated animals, with clear improvement in the performance of the mice treated with D-Trp-Aib (FIG. 56). This is most notable in the last 2 days of the test (p<0.05 Mann-Whitney U-test), showing the retention of learning capabilities in treated mice, capabilities which were lost in amyloid producing non treated mice.

D-Trp-Aib significantly reduced β-amyloid concentrations in brain and cerebrospinalfluid (CSF)—Evaluation $A\beta_{1-42}$ and $A\beta_{1-40}$ concentrations in the SDS and formic acid (FA) fractions of brain homogenates of hAPP tg animals, showed that treatment with D-Trp-Aib greatly reduced the Aβ concentrations in the brains of HAPP tg animals in comparison to the vehicle control group, as evaluated by the soluble and insoluble β-amyloid deposition in the cerebrospinal fluid in four brain fractions and plaque load (FIG. 57). $hA\beta_{1-40}$ levels were significantly reduced in the SDS fraction following D-Trp-Aib treatment (FIG. 57a); the same was seen for $hA\beta_{1-42}$ albeit at a lower significance level (FIG. 57b). Insoluble (formic-acid requiring) hAβ in the FA fraction was not affected by D-Trp-Aib (FIGS. 57 c and d).

D-Trp-Aib treatment resulted in reduction of β-amyloid plaques—treatment with D-Trp-Aib resulted in reduction of the plaque load in comparison to vehicle treated mice. ThioflavinS labeling showed that plaque region area (FIGS. 58a and d), relative plaque area (FIGS. 58b and e) and mean plaque size (FIGS. 58c and f) were reduced in hAPP tg animals treated with D-Trp-Aib. Notably, the mean size of β-sheet cores was significantly reduced by D-Trp-Aib in the cortex (FIG. 58c). There was a clear tendency (although not statistically significant) of D-Trp-Aib to reduce the total area of β-sheet cores (FIGS. 58b and e). In an overlay of two consecutive slices of the cortex, one stained with 6E10 and one with ThioflavinS, the effect of D-Trp-Aib (FIG. 59a) on the ThioflavinS positive β-sheet cores of neuritic plaques is clearly seen when compared to vehicle treated controls (FIG. 59b).

Histological sections from the frontal section of the brain cortex of hAPP (751) transgenic mice, which show the development of plaques in a Campbell-Switzer stain, also displayed a significant reduction in the size and surface area of the plaque cores of D-Trp-Aib treated animals (FIG. 60b) when compared to vehicle-treated control (FIG. 60a). Plaques in the vehicle-treated mice were usually framed by a number of additional newly built agglomerates, while those in the D-Trp-Aib treated group frequently had sharply defined borders without the surrounding plaque seeds. In addition, a markedly smaller number of new, small-sized plaques in the tissue between mature plaques were seen in the D-Trp-Aib group.

D-Trp-Aib showed no long-term toxicity: 7 of the original 20 animals died during the 4-month experimental period, 4 of them from the control group, suggesting that the deaths were not drug related.

Given together, in vivo results strengthen the view that D-Trp-Aib affects the early molecular recognition and self-assembly process that leads to the formation of toxic amyloidal species. Without being bound by theory, treatment with D-Trp-Aib most likely affects the ability of Aβ monomers to form well-ordered and toxic amyloidal assemblies. This is evidenced by the significant reduction in the toxic ThioflavinS positive species compared to non-ordered and probably non-toxic amyloidal assemblies (FIGS. 58 and 59). Thus, it appears that, unlike other compounds, D-Trp-Aib does not break down formed assemblies that may cause new aggregation of toxic assemblies, but rather alters the recognition and assembly processes, precluding the formation of toxic species. The restricted aromatic-geometry and the non-β-sheet structures of the altered assembly, which are not consistent with the growth of the amyloid structures, suggest a mechanism of action that is superior to any previously described model compounds. This is strongly reflected in the improvement in the cognitive performance of the treated mice (FIG. 56).

Example 51

The Pharmaceutical and Pharmacokinetic Profile of D-Trp-Aib

Methods

D-Trp-Aib serum stability—Regardless of administration route, all drugs penetrate and distribute in the body via the blood system. This milieu is based not only on cells and buffering compounds, but also on proteins, carbohydrates, lipid-protein micelles, etc. Serum proteins mainly contain carrier proteins, such as albumin, but also contain many enzymes that might treat the drug as a substrate. Thus, the susceptibility of any drug entering this environment should be evaluated. The stability of D-Trp-Aib spiked into serum was evaluated by analysis of intact sample concentrations at different time points. D-Trp-Aib (250 µg/ml PBS) was incubated with mouse (Harlan Biotech, Israel) or human (obtained from Sheba medical center, Tel Hashomer, Israel) sera or PBS (1:1, 37° C.), and aliquots were analyzed by HPLC analysis at times 0, 2 and 5 hrs. The reaction was stopped and precipitation was effected by the addition of acetonitrile (Baker, Phillipsburg N.J.) and 10% TCA. Following centrifugation (10,000 g, 5 min), Supernatant was transferred to HPLC analysis. Mean amounts of D-Trp-Aib (μg)±s.e.m. were calculated by an internal calibration curve.

Membrane permeability of D-Trp-Aib as studied in Caco-2 cells—The CaCo-2 system is based on the intestinal properties of the Caco-2 cells (ATCC Accession No. HTB-37), which preserved the polarity that is seen in the intestinal wall—an apical brush border that faces the intestinal lumen and a basolateral side that faces the body. After initial culturing (37° C. in an atmosphere of 5% $CO_2$ and 100% humidity; medium: D-glucose DMEM supplemented with 1% Lglutamine, 1% nonessential amino acids, 1% sodium pyruvate, 1% penicillin streptomycin, and 10% fetal bovine serum), cells were harvested and grown (14 days) on polycarbonate membranes, on which they formed a tight monolayer, (width of one cell, as in the intestine) allowing specific compounds to penetrate. Generally, large compounds do not penetrate, but a small compound might penetrate, either in hydrophilic route between the cells (paracellular permeability) or in hydrophobic route (transcellular permeability). D-Trp-Aib membrane permeability of the Caco-2 cell monolayer was assessed at concentrations of 0.2 mM and 1 mM, and compared to the standards propranolol (1 mM/apical buffer-see below) and $^3$H-mannitol (5.26 Ci/mmole apical buffer-see below), known to pass via transcellular and paracellular routes, respectively. Test substances transport across Caco-2 monolayers was investigated in 'apical to basolateral' direction (n=2), at two time points (45 and 90 minutes). Prior to the experiment, the culture medium was removed; cells were washed twice with 150 μl apical buffer (25 mM D-glucose, 20 mM MES biological buffer, 1.25 mM CaCl2, 0.5 mM MgCl2, adjusted to pH 6.5 with KOH) and 600 μl basolateral buffer (25 mM D-glucose, 20 mM HEPES, 1.25 mM $CaCl_2$, 0.5 mM MgCl2, adjusted to pH 7.4 with KOH) and incubated for 30 min at 37° C., 45 RPM, with the same buffers. At time 0, 30 μl buffer were removed from the apical chamber and 5-fold concentrated stock solutions of D-Trp-Aib were loaded. Transport studies were performed at 37° C., with shaking at 45 RPM with either test substances or standards (n=2). Substance samples and Propranolol standard were analyzed using HPLC. $^3$H-Mannitol samples were subjected to analysis by liquid scintillation counting in a Packard TopCount NXT. The results were obtained in CPM.

HPLC analysis for serum stability and membrane permeability—An HPLC procedure was developed for D-Trp-Aib samples spiked into serum for serum stability assays: HPLC system (Waters 2790 HPLC system, with PDA 996 detector) was used with solvents A: 0.1% TFA and B: Acetonitrile, 0.1% TFA; Solid phase was: LichroCART C-18 250-4, particle size 5 μm, 250-4 mm (Merck, Whitehouse Station, N.J.; Cat No. 150212) at RT. The data was processed using Millennium software. Processing wavelength was set to 280 nm. Conditions are presented in Table 8, below.

TABLE 8

| Time [minutes] | A | B |
|---|---|---|
| 1 | 95 | 5 |
| 15 | 50 | 50 |
| 20 | 5 | 95 |
| 22 | 95 | 5 |

Pharmacokinetics in Mice—In order to assess D-Trp-Aib pharmacokinetics, bioavailability upon oral and/or nasal administration in CD-1 model mice (56 mice weighing 30-40 gr) was effected. D-Trp-Aib was administered at a single oral dose of 50 mg/kg bw (dissolved in Aqua B. Braun to a concentration of 5 mg/mL; 10 mL/kg bw); an intravenous bolus dose of 50 mg/kg bw (dissolved in physiological saline to a concentration of 5 mg/mL; 10 mL/kg bw) or an intranasal administration of 20 mg/kg bw (dissolved in a physiological saline at a drug concentration of 10 mg/mL, given in 3 applications to each nostril using a micropipette). Animals were treated following a 4 hour fast, with water ad libitum, and fed 2 hours after administration. Thereafter, animals were sacrificed at different time intervals (5 minutes-8 hours; 3 animals in each group, at every time interval were sacrificed by sodium pentobarbital anesthesia followed by exanguination) and blood (plasma), brain, liver, kidney and pancreas were collected and later analyzed. Plasma and brain tissue samples were analyzed by high-performance liquid chromatography with tandem mass spectrometry (LC-MS/MS).

Based on the D-Trp-Aib concentrations obtained after each administration, the calculation of the following parameters was performed: Co (extrapolated maximum concentration intravenous route), Cmax (maximum concentration) and tmax (time taken to reach maximum concentration) for the oral rout, calculated from the experimental data; Elimination of half life, calculated by linear regression using slope of the terminal segment of the concentration-time curve; $AUC_{0-4}$ (area under the concentration-time curve from 0 to the last measurable concentration, calculated using the trapezoidal rule); V (the apparent volume of distribution based on AUC trapezoid calculation and elimination rate, calculated by v=Dose/AUC.λz); Cl (the systemic clearance, based on trapezoid area and calculated by Cl=Dose/AUC). In case of brain tissue, only $AUC_{0-4}$ was calculated. All parameters were calculated using the software PK solutions Version 2.0 for Non-compartmental Pharmacokinetics Data analysis (Summit Research Services, Montrose, Colo.).

Chromatographic Conditions for Plasma and Brain Tissue Samples—

| | |
|---|---|
| Column | HPLC column (X-Terra RP18, 3.5 μm particle size, 100 mm × 4.6 mm ID, Waters, Milford USA) |
| Pre-column | HPLC pre-column (X-Terra RP18, Waters, Milford USA) |
| Column temp. | 30° C. |
| Injector temp. | 4° C. |
| Run time | 3 min for plasma; 6.5 min for brain tissue |
| Injection Vol. | 45 μL |
| Column flow rate | 1.0 mL/min |

-continued

| | |
|---|---|
| Mobile phase | Isocratic elution used for plasma samples:<br>0.1% TFA in Milli-Q grade water/0.1% TFA in CAN (70:30 v/v)<br>Gradient elution used for brain tissue samples:<br>t 0.00 ammonium acetate 10 mM pH 3.5: 85% ACN 15% flow rate: 1.0 ml/min<br>t 3.00 ammonium acetate 10 mM pH 3.5: 60% ACN 40% flow rate: 1.0 ml/min<br>t 4.50 ammonium acetate 10 mM pH 3.5: 60% ACN 40% flow rate: 1.0 ml/min<br>t 4.51 ammonium acetate 10 mM pH 3.5: 85% ACN 15% flow rate: 1.0 ml/min<br>t 6.50 ammonium acetate 10 mM pH 3.5: 85% ACN 15% flow rate: 1.0 ml/min |

Mass Spectroscopic Conditions—

| | |
|---|---|
| Ionization mode | Electrospray using a heated nebulizer interface in the positive ion mode |
| Desolvation gas | Nitrogen |
| Cone gas flow | 50 L/Hr |
| Desolvation gas flow | 350 L/hr |
| Collision gas | Argon |
| Source Temp. | 120° C. |
| Desolvation Temp. | 250° C. |
| Cone voltage | 15.00 V |
| Capillary voltage | 3.00 kV |
| Collision energy | 21 e |
| Multiple Reaction Monitoring of one mass pair | D-Trp-Aib m/z 290 > m/z 159.00 |

Cytotoxicity assay in hepatocytes—Following culture (37° C. in an atmosphere of 5% $CO_2$ and 100% humidity), HepG2 cells (ATCC Accession No: HB-8065) were seeded at a density of 5000 cells/well in 96 well optical plate (Nunc, Rochester, N.Y.). Culture was maintained in the logarithmic phase throughout the experiment. One day after seeding, peptides were dissolved in DMSO (1:10) and added to the wells to achieve final concentrations of $2.5 \times 10^{-4}$-$1 \times 10^{-8}$. Each plate column (8 wells) was used to test one peptide in one concentration. A day following peptide addition, $^3$H-Thymidine was added to the cell culture, and two days following addition cells were harvested. $^3$H-Thymidine incorporation to the DNA of proliferating cells was measured in Top Count NTX counter (Packard, Quebec, Canada). For viability assay, cells were supplemented with 10% (v/v) Alamar Blue indicator in fresh medium, one day prior to harvesting. The indicator was incubated for 18 hours and fluorescence was measured with 544 nm excitation/590 nm emission wavelengths. Data was presented as the mean amount of Alamar-Blue fluorescence or $^3$H-Thymidine CPM monitored per well. Average was calculated per plate column. For Alamar-Blue signals standard deviation (SD) was calculated, while for $^3$H Thymidine signal, standard error (SE) was calculated. Outliers (one out of 8 replicates) were rejected according to the formula: Q=|suspected outlier−closest value|/|maximum value−minimum value| If Q is larger than 0.47 (for n=8) the outlier was discarded with 90% confidence. Equivocal results were analyzed using oneway (ANOVA) with Dunnett Multiple comparison Test.

Neurotoxicity (5% assay)—Neural cells were grown in Poly-D-Lysine coated 96-well plates. Eighty μl medium containing 48.000 cells/well were added to each well plate containing 80 μl T.I. in the appropriate concentrations, or nutrition medium (control). Plates were kept at 37° C., 95% humidity and 5% CO2. Neurons, which begin to extend processes after a few hours in culture, were maintained in the same medium without change or addition of media for 8 days, until the end of the experiments. For Neurotoxicity, the MTT-assay was effected using a plate-reader (570 nm) for determining the culture viability, as described in Example 49. The MTT assay is based on the ability of a dehydrogenase enzyme from an active mitochondiria to produce a dark blue formazan product from the pale yellow MTT substrate, by cleaving the MTT tetrazolium rings. Since in the MTT-assay sometimes interference between the substance/drug applied and the generation of formazane crystals can be seen, it is necessary to introduce a second evaluation system. Therefore, the viability of cultures was determined with the Calcein-AM assay as well, as described in Neri et al., [Clin. Diagn. Lab Immunol. 1131-1135 (2001)], using an automated fluorescence plate-reader (485/535 nm). Calcein AM is a widely used green fluorescent cell marker, which is membrane-permeant and thus can be introduced into cells via incubation. This assay is less sensitive than the MTT-assay but its strength is that it measures not only the mitochondrial activity in viable cells but the overall viability of the remaining cells.

Functional HERG assay—Compounds were tested in duplicate in a 3-point dose response curve on HEK cells stably expressing the hERG potassium channel (GenBank Accession No. AAD01946). Potassium current was measured using the patch clamp technique on a Molecular Devices Patch Express 7000. hERG channels were activated by 2 second pulses to +20 mV from a holding potential of −80 mV, and $K^+$ currents were recorded upon repolarization to −50 mV. This voltage-clamp pulse protocol was performed continuously during the experiment (vehicle control, test compound, washout, and positive control additions). An inter-pulse interval of 15 seconds allowed recovery from any residual inactivation. Compounds were incubated with cells between 3-8 minutes until the current reached a steady state level. After compounds were tested, they were washed out with continuous perfusion for 3 minutes, followed by application of positive control (10 uM Cisparide).

Specificity (HitProfiling) and Metabolic Stability (CYP-450)—D-Trp-Aib activity was evaluated in enzyme profiling screens, as the percent of inhibition of specific binding or activity of enzymes including receptors for adenosine, adrenergic, calcium channel L-type, dopamine, GABA, muscarinic, nicotinic, acetylcholine and potassium channel. $IC_{50}$ values were determined by a non-linear, least squares regression analysis using Data Analysis Toolbox (MDL Information Systems, San Leandro, Calif., USA). K¾ values were calculated using the equation of Cheng and Prusoff[Cheng, Y., Prusoff, W. H., Biochem. Pharmacol. 22:3099-3108 (1973)] using the observed $IC_{50}$ of the tested compound, the concentration of radioligand employed in the assay, and the historical values for the $K^1$ of the ligand (obtained experimentally at MDS Pharma Services, Taipei, Taiwan). The Hill coefficient (n½), defining the slope of the competitive binding curve, was calculated using Data Analysis Toolbox. $IC_{50}$, K¾, and/or n½ data were presented with Standard Error of the Mean (SEM), unless data were insufficient to be quantitative.

For the metabolic stability assay, Human cytochrom P450 (CYP450) screens were used. The cytochrom P450 isoenzymes, which are located in the intestines, liver, lung, kidney and brain, are involved in important drug interactions. Drug metabolism occurs in two phases—Phase I involves oxidation, reduction, and hydrolysis. Phase II involves synthesis and conjugation. The CYP 450 isoenzymes are involved in Phase I oxidative reactions. CYP 450 interactions generally result from one of two processes—Induction, where a substance stimulates the synthesis of the enzyme and metabolic capacity is increased, and inhibition, where competitive binding at an enzyme's binding site(s) occurs. A drug with a high affinity for an enzyme will slow the metabolism of any low affinity drug. CYP 3A3/4 is the most abundant CYP 450 isoenzyme in humans and is responsible for the metabolism of the widest range of drugs/substances. (CYP450) screens used were 1A2, 2C9, 2C19, 2D6 and 3A4.

Acute Toxicity in Mice—Single dose $LD_{50}$ or maximal tolerated dose (MTD) of D-Trp-Aib was evaluated by i.v. administration in mice (Harlan Biotech Israel). The sequential method applied in a stepwise procedure, using a minimum amount of animals. At a preliminary phase, an initial single target dose of 250 mg/kg was administered to a group of one male and one female. Further higher dose levels of 500, 1,000 and 750 mg/kg were administered in view of presence or absence of lethality incidence and/or severe adverse reactions at each applied level. The time intervals between the test groups dosing sessions were at least 24 hours. Following termination of the preliminary phase and based on its findings, a main phase was conducted where 5 males & 5 females were administered the jointly selected dose of 750 mg/kg, the highest dose level that was suspected to produce no mortality.

Results

Serum Stability—The stability of D-Trp-Aib spiked into serum was evaluated by HPLC analysis of samples incubated at 37° C. for different time periods. No decrease was observed in D-Trp-Aib concentration after 2 and 5 hours of incubation in mouse or human serum. D-Trp-Aib was found to be highly stable in human and mouse sera (FIG. 61). This is consistent with the design of the D-Trp-Aib compound library using metabolically stable building blocks (D-amino acids).

Potential for membrane barrier permeability, in vitro studies in Caco-2 cells—D-Trp-Aib membrane permeability was assessed using Caco-2 cells monolayer and compared to the standards propranolol and $^3$H-mannitol, known to pass via transcellular and paracellular routes, respectively. Recovery of D-Trp-Aib at the experimental end point (90 min) was 19.30%±6.5% and 37.9%±18.6% for the 1 mM and 0.2 mM concentrations, respectively. This is similar to the efflux value of mannitol, a marker of paracellular transport.

HPLC analytical method—An HPLC procedure was developed for D-Trp-Aib samples. The method shows good sensitivity with a detection limit of 0.2 mM.

LC-MS/MS bioanalysis—An LC-MS/MS procedure was developed for D-Trp-Aib biological samples. Table 9 shows linearity and sensitivity of the LC-MS/MS bioanalytical method for D-Trp-Aib. The D-Trp-Aib method shows good linearity with a sensitivity of detection limit of 5 ng/ml and 50 ng/g for serum and brain samples, respectively (FIGS. 64*a-b*).

TABLE 9

D-Trp-Aib in mouse plasma

Back calculated concentrations (ng/ml)
Calibration level (ng/ml)

| Batch | 5.00 | 10.00 | 20.0 | 50 | 100 | 500 | 1000 | 5000 | 10000 | 50000 |
|---|---|---|---|---|---|---|---|---|---|---|
| RUN 1 | 5.575 | 10.801 | 17.872 | 39.465 | 95.068 | 453.537 | 936.299 | 5690.436 | 9659.942 | 52340.505 |
| Accuracy (%) | 11.5 | 8.0 | −10.6 | −21.1 (OA) | −4.9 | −9.3 | −6.4 | 13.8 | −3.4 | 4/7 |

Calibration curve: y = 0.945367x + 0.536037 (r = 0.999605)

D-Trp-Aib in brain tissue

Back calculated concentrations (ng/ml)
Calibration level (ng/ml)

| Batch | 50 | 100 | 200 | 500 | 1000 | 5000 |
|---|---|---|---|---|---|---|
| RUN 1 | 53.750 | 101.690 | 197.780 | 473.510 | 862.97 | 5659.650 |
| Accuracy (%) | 7.5 | 1.7 | −1.1 | −5.3 | −13.7 | 13.2 |

Calibration curve: y = 1.00503x − 0.615482 (r = 0.998368)

Pharmacokinetics in mice—D-Trp-Aib shows excellent bioavailability upon oral and/or nasal administration in CD-1 model mice. D-Trp-Aib concentrations were assessed in plasma and brain homogenates of animals treated by the intravenous, oral (by gavage) and intranasal administration routes. Results obtained by LC-MS/MS analysis are summarized in Table 10, which shows oral and nasal bioavailability of the compound as well as blood-brain barrier entrance.

TABLE 10

| | | Oral route (50 mg/kg; aqua B. Braun) | Intravenous route (50 mg/kg; physiological saline) | Intranasal route (~20 mg/kg; physiological saline) |
|---|---|---|---|---|
| EG30 in plasma | | | | |
| Elimination half-life | hr | 1.07 | 1.22 | 1.29 |
| $C_{max}$ (po) | ng/mL | 9810.73 | n/a | n/a |
| $t_{max}$ | hr | 1.00 | n/a | n/a |
| $AUC_{(0-t)}$ (OBS area) | ng-hr/mL | 15689.31 | 40582.72 | 10637.23 |
| $AUC_\infty$ (area) | ng-hr/mL | 15726.36 | 40625.69 | 11379.87 |
| $AUC_{extra}$ | % | 0.24 | 0.11 | 6.98 |
| MRT (area) | hr | 1.29 | 0.44 | 0.98 |
| Vd (area)/kg* | mL/kg | 1905.81 | 2162.91 | 2144.74 |
| Cl (area)/kg* | mL/hr/kg | 1229.14 | 1230.75 | 1151.68 |
| Bioavailability (F) | % | 38.66 | 100.00 | 65.53 |
| EG30 in brain tissue | | | | |
| AUC (0-t) (obs area) | | 453.91 | 2173.55 | 943.85 | n/a: not applicable
*Corrected by F

Cytotoxicity assay in hepatocytes—D-Trp-Aib was found to have no cytotoxic effect on HepG2 cells in the tested concentration range of $1 \times 10^{-8}$-$2.5 \times 10^{-4}$ M as determined by $^3$H-Thymidine incorporation assay and Alamar-Blue™ Assay, Neurotoxicity assay (5% assay)—D-Trp-Aib was found to be noncytotoxic towards neuronal primary cell cultures as determined by MTT viability assay (ODs, FIG. 62a) and Calcein AM assay (FIG. 62b). Fluorescent counts have shown that D-Trp-Aib did not alter neuronal viability compared to the untreated control in a concentration of up to 150 μM.

Functional hERG assay—D-Trp-Aib did not show any effect on potassium channels in a functional hERG potassium channel assay, suggesting that it would not have adverse cardiac effects. D-Trp-Aib does not inhibit the potassium current within the pharmaceutical concentration range ($IC_{50}$>50 mM).

Specificity (HitProfiling)—D-Trp-Aib activity was evaluated in enzyme profiling screens including receptors for adenosine, adrenergic, calcium channel L-type, dopamine, GABA, muscarinic, nicotinic, acetylcholine and potassium channel. None of the results met significance criteria at concentrations and/or doses tested.

Metabolic Stability—CYP450-D-Trp-Aib activity was evaluated in enzyme profiling and CYP450 screens. Human CYP450 screens used were 1A2, 2C9, and 3A4. None of the results met significance criteria at concentrations and/or doses tested.

Acute Toxicity in Mice—Single dose $LD_{50}$ or maximal tolerated dose (MTD) of D-Trp-Aib was evaluated by i.v. administration in mice. D-Trp-Aib's MTD level is above 750 mg/kg but below 1,000 mg/kg. However, it must be stressed that all the male mice and most of the female mice showed no adverse signs upon intravenous administration of 1,000 mg/kg D-Trp-Aib.

PH and temperature stability of D-Trp-Aib—The stability of D-Trp-Aib was examined at different pH values, and at different temperatures, using analytical reversed phase high performance liquid chromatography (RP-HPLC), Stability was found to be maintained at various pH values and temperatures as high as 60° C. (FIG. 63).

Thus, the D-Trp-Aib compound has unusual potential to be used as a pharmaceutical because of its positive pharmacokinetic properties:

1. D-Trp-Aib has a half-life on the order of 1.1-1.2 hours
2. D-Trp-Aib is rapidly absorbed after oral administration as evidenced by detection as early as 15 min post-dosing.
3. D-Trp-Aib is efficiently absorbed by the vascular nasal epithelium after three consecutive applications of the formulation into each nostril. Nasal bioavailability is 65.53%.
4. The oral bioavailability of D-Trp-Aib is 38.66%, suggesting a first pass metabolism of the drug after oral administration.
5. D-Trp-Aib is detected in all the assayed brain tissue samples, confirming its efficient transport through the blood-brain barrier irrespective of the administration route
6. Intranasal administration produces a higher exposure of the brain to D-Trp-Aib compared to the oral administration route, suggesting direct access of the drug to the brain, perhaps via the olfactory region.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A synthetic dipeptide as set forth in SEQ ID NO: 145 (D-Trp-Aib).

2. A pharmaceutical composition comprising as an active ingredient a synthetic dipeptide as set forth in SEQ ID NO: 145 (D-Trp-Aib) and a pharmaceutically acceptable carrier or diluent.

* * * * *

SEQUENCE LISTING

<160> NUMBER OF SEQ ID NOS: 166

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Asn Phe Gly Ala Ile Leu Ser Ser
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ala Phe Gly Ala Ile Leu Ser Ser
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Asn Ala Gly Ala Ile Leu Ser Ser
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Asn Phe Ala Ala Ile Leu Ser Ser
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Asn Phe Gly Ala Ala Leu Ser Ser
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Asn Phe Gly Ala Ile Ala Ser Ser
1               5

<210> SEQ ID NO 7
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Any aromatic amino acid
<220> FEATURE:
<221> NAME/KEY: misc_feature
<222> LOCATION: (2)..(2)
<223> OTHER INFORMATION: Any amino acid, but glycine
<220> FEATURE:
<221> NAME/KEY: misc_feature
<222> LOCATION: (3)..(5)
<223> OTHER INFORMATION: Any amino acid

<400> SEQUENCE: 7

Xaa Xaa Xaa Xaa Xaa
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Ala Phe Gly Ala Ile Leu
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Asn Ala Gly Ala Ile Leu
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Asn Phe Gly Ala Ala Leu
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Asn Phe Gly Ala Ile Ala
1               5

```
<210> SEQ ID NO 12
<211> LENGTH: 6
<212> TYPE: PRT
<213> ORGANISM: Artificial sequence
<220> FEATURE:
<223> OTHER INFORMATION: Synthetic peptide

<400> SEQUENCE: 12

Asn Phe Ala Ala Ile Leu
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Phe Ala Ala Ile Leu
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Asn Phe Leu Val His Ser Ser Asn Asn
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Asn Phe Leu Val His Ser Ser
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Phe Leu Val His Ser Ser
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide

<400> SEQUENCE: 17

Asn Phe Leu Val His
1               5
```

```
<210> SEQ ID NO 18
<211> LENGTH: 5
<212> TYPE: PRT
<213> ORGANISM: Artificial sequence
<220> FEATURE:
<223> OTHER INFORMATION: Synthetic peptide

<400> SEQUENCE: 18

Phe Leu Val His Ser
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic peptide

<400> SEQUENCE: 19

Phe Leu Val His
1

<210> SEQ ID NO 20
<211> LENGTH: 8
<212> TYPE: PRT
<213> ORGANISM: Artificial sequence
<220> FEATURE:
<223> OTHER INFORMATION: Synthetic peptide

<400> SEQUENCE: 20

Asn Phe Gly Ser Val Gln Val Phe
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic peptide

<400> SEQUENCE: 21

Asn Phe Gly Ser Val Gln
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide

<400> SEQUENCE: 22

Asn Phe Gly Ser Val
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic peptide

<400> SEQUENCE: 23

Phe Gly Ser Val Gln
1               5
```

```
<210> SEQ ID NO 24
<211> LENGTH: 4
<212> TYPE: PRT
<213> ORGANISM: Artificial sequence
<220> FEATURE:
<223> OTHER INFORMATION: Synthetic peptide

<400> SEQUENCE: 24

Gly Ser Val Gln
1

<210> SEQ ID NO 25
<211> LENGTH: 4
<212> TYPE: PRT
<213> ORGANISM: Artificial sequence
<220> FEATURE:
<223> OTHER INFORMATION: Synthetic peptide

<400> SEQUENCE: 25

Phe Gly Ser Val
1

<210> SEQ ID NO 26
<211> LENGTH: 6
<212> TYPE: PRT
<213> ORGANISM: Artificial sequence
<220> FEATURE:
<223> OTHER INFORMATION: Synthetic peptide

<400> SEQUENCE: 26

Asn Ala Gly Ser Val Gln
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic peptide

<400> SEQUENCE: 27

Asp Phe Asn Lys Phe
1               5

<210> SEQ ID NO 28
<211> LENGTH: 4
<212> TYPE: PRT
<213> ORGANISM: Artificial sequence
<220> FEATURE:
<223> OTHER INFORMATION: Synthetic peptide

<400> SEQUENCE: 28

Phe Asn Lys Phe
1

<210> SEQ ID NO 29
<211> LENGTH: 4
<212> TYPE: PRT
<213> ORGANISM: Artificial sequence
<220> FEATURE:
<223> OTHER INFORMATION: Synthetic peptide

<400> SEQUENCE: 29

Asp Phe Asn Lys
1

<210> SEQ ID NO 30
```

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 30

Asp Phe Asn
1

<210> SEQ ID NO 31
<211> LENGTH: 5
<212> TYPE: PRT
<213> ORGANISM: Artificial sequence
<220> FEATURE:
<223> OTHER INFORMATION: Synthetic peptide

<400> SEQUENCE: 31

Asp Ala Asn Lys Phe
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic peptide

<400> SEQUENCE: 32

Leu Phe Asn Gln Thr Gly
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic peptide

<400> SEQUENCE: 33

Ser Phe Phe Ser Phe Leu
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide

<400> SEQUENCE: 34

Phe Glu Asn Lys Phe
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide

<400> SEQUENCE: 35

Ser Phe Asn Asn Gly
1               5

<210> SEQ ID NO 36
<211> LENGTH: 6
```

```
<212> TYPE: PRT
<213> ORGANISM: Artificial sequence
<220> FEATURE:
<223> OTHER INFORMATION: Synthetic peptide

<400> SEQUENCE: 36

Leu Gln Asn Phe Thr Leu
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic peptide

<400> SEQUENCE: 37

Thr Leu Ile Phe Gly Gly
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic peptide

<400> SEQUENCE: 38

Arg Ala Leu Asp Phe Ala
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic peptide

<400> SEQUENCE: 39

Gly Leu Val Phe Val Ser
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic peptide

<400> SEQUENCE: 40

Gly Thr Phe Gln Ile Asn
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

Ser Gly Ile Phe Thr Asn
1               5

<210> SEQ ID NO 42
<211> LENGTH: 5
<212> TYPE: PRT
```

```
<213> ORGANISM: Artificial sequence
<220> FEATURE:
<223> OTHER INFORMATION: Synthetic peptide

<400> SEQUENCE: 42

Glu Arg Gly Phe Phe
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic peptide

<400> SEQUENCE: 43

Arg Asp Phe Leu Asp Arg
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic peptide

<400> SEQUENCE: 44

Ser Asn Phe Leu Asn
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic peptide

<400> SEQUENCE: 45

Asn Phe Leu Val His Pro Pro
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic peptide

<400> SEQUENCE: 46

Asn Phe Gly Ala Ile Leu Ser Ser
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47

Asn Ile Gly Ala Ile Leu Ser Ser
1               5

<210> SEQ ID NO 48
<211> LENGTH: 8
<212> TYPE: PRT
<213> ORGANISM: Artificial sequence
```

-continued

```
<220> FEATURE:
<223> OTHER INFORMATION: Synthetic peptide

<400> SEQUENCE: 48

Asn Leu Gly Ala Ile Leu Ser Ser
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic peptide

<400> SEQUENCE: 49

Asn Val Gly Ala Ile Leu Ser Ser
1               5

<210> SEQ ID NO 50
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 50
aaatgcaaca ccgcgacctg cgcg                                          24

<210> SEQ ID NO 51
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 51
acccagcgcc tggcgaactt tctggtgcat                                    30

<210> SEQ ID NO 52
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 52
agcagcaaca actttggcgc gattctgagc                                    30

<210> SEQ ID NO 53
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 53
agcaccaacg tgggcagcaa cacctattaa tga                                33

<210> SEQ ID NO 54
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 54
```

```
tcgttgtgca taattact                                                     18

<210> SEQ ID NO 55
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 55
ccgcgctaag actcgtcgtg cttgcacccg                                        30

<210> SEQ ID NO 56
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 56
cgcttgaaag accacgtatc gtcgttgttg aaa                                    33

<210> SEQ ID NO 57
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 57
tttacgttgt ggcgctggac gcgctgggtc gcggac                                 36

<210> SEQ ID NO 58
<211> LENGTH: 114
<212> TYPE: DNA
<213> ORGANISM: Artificial sequence
<220> FEATURE:
<223> OTHER INFORMATION: Modified IAPP cDNA for expression in bacteria

<400> SEQUENCE: 58
atgaaatgca acaccgcgac ctgcgcgacc cagcgcctgg cgaactttct ggtgcatagc       60
agcaacaact tggcgcgcat tctgagcagc accaacgtgg gcagcaacac ctat            114

<210> SEQ ID NO 59
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 59
gggtttccat gggccatcac catcaccatc acgaaaaatg caacaccgcg acctgc           56

<210> SEQ ID NO 60
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 60
gggtttgcgg ccgctcatta ataggtgttg ctgcc                                  35

<210> SEQ ID NO 61
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 61

Lys Cys Asn Thr Ala Thr Cys Ala Thr Gln
1               5                   10

<210> SEQ ID NO 62
<211> LENGTH: 10
<212> TYPE: PRT
<213> ORGANISM: Artificial sequence
<220> FEATURE:
<223> OTHER INFORMATION: Synthetic peptide

<400> SEQUENCE: 62

Cys Asn Thr Ala Thr Cys Ala Thr Gln Arg
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic peptide

<400> SEQUENCE: 63

Asn Thr Ala Thr Cys Ala Thr Gln Arg Leu
1               5                   10

<210> SEQ ID NO 64
<211> LENGTH: 10
<212> TYPE: PRT
<213> ORGANISM: Artificial sequence
<220> FEATURE:
<223> OTHER INFORMATION: Synthetic peptide

<400> SEQUENCE: 64

Thr Ala Thr Cys Ala Thr Gln Arg Leu Ala
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic peptide

<400> SEQUENCE: 65

Ala Thr Cys Ala Thr Gln Arg Leu Ala Asn
1               5                   10

<210> SEQ ID NO 66
<211> LENGTH: 10
<212> TYPE: PRT
<213> ORGANISM: Artificial sequence
<220> FEATURE:
<223> OTHER INFORMATION: Synthetic peptide

<400> SEQUENCE: 66

Thr Cys Ala Thr Gln Arg Leu Ala Asn Phe
1               5                   10

<210> SEQ ID NO 67
<211> LENGTH: 10
<212> TYPE: PRT
```

```
<213> ORGANISM: Artificial sequence
<220> FEATURE:
<223> OTHER INFORMATION: Synthetic peptide

<400> SEQUENCE: 67

Cys Ala Thr Gln Arg Leu Ala Asn Phe Leu
1               5                   10

<210> SEQ ID NO 68
<211> LENGTH: 10
<212> TYPE: PRT
<213> ORGANISM: Artificial sequence
<220> FEATURE:
<223> OTHER INFORMATION: Synthetic peptide

<400> SEQUENCE: 68

Ala Thr Gln Arg Leu Ala Asn Phe Leu Val
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic peptide

<400> SEQUENCE: 69

Thr Gln Arg Leu Ala Asn Phe Leu Val His
1               5                   10

<210> SEQ ID NO 70
<211> LENGTH: 10
<212> TYPE: PRT
<213> ORGANISM: Artificial sequence
<220> FEATURE:
<223> OTHER INFORMATION: Synthetic peptide

<400> SEQUENCE: 70

Gln Arg Leu Ala Asn Phe Leu Val His Ser
1               5                   10

<210> SEQ ID NO 71
<211> LENGTH: 10
<212> TYPE: PRT
<213> ORGANISM: Artificial sequence
<220> FEATURE:
<223> OTHER INFORMATION: Synthetic peptide

<400> SEQUENCE: 71

Arg Leu Ala Asn Phe Leu Val His Ser Ser
1               5                   10

<210> SEQ ID NO 72
<211> LENGTH: 10
<212> TYPE: PRT
<213> ORGANISM: Artificial sequence
<220> FEATURE:
<223> OTHER INFORMATION: Synthetic peptide

<400> SEQUENCE: 72

Leu Ala Asn Phe Leu Val His Ser Ser Asn
1               5                   10

<210> SEQ ID NO 73
<211> LENGTH: 10
<212> TYPE: PRT
<213> ORGANISM: Artificial sequence
```

<220> FEATURE:
<223> OTHER INFORMATION: Synthetic peptide

<400> SEQUENCE: 73

Ala Asn Phe Leu Val His Ser Ser Asn Asn
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic peptide

<400> SEQUENCE: 74

Asn Phe Leu Val His Ser Ser Asn Asn Phe
1               5                   10

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

Phe Leu Val His Ser Ser Asn Asn Phe Gly
1               5                   10

<210> SEQ ID NO 76
<211> LENGTH: 10
<212> TYPE: PRT
<213> ORGANISM: Artificial sequence
<220> FEATURE:
<223> OTHER INFORMATION: Synthetic peptide

<400> SEQUENCE: 76

Leu Val His Ser Ser Asn Asn Phe Gly Ala
1               5                   10

<210> SEQ ID NO 77
<211> LENGTH: 10
<212> TYPE: PRT
<213> ORGANISM: Artificial sequence
<220> FEATURE:
<223> OTHER INFORMATION: Synthetic peptide

<400> SEQUENCE: 77

Val His Ser Ser Asn Asn Phe Gly Ala Ile
1               5                   10

<210> SEQ ID NO 78
<211> LENGTH: 10
<212> TYPE: PRT
<213> ORGANISM: Artificial sequence
<220> FEATURE:
<223> OTHER INFORMATION: Synthetic peptide

<400> SEQUENCE: 78

His Ser Ser Asn Asn Phe Gly Ala Ile Leu
1               5                   10

<210> SEQ ID NO 79
<211> LENGTH: 10
<212> TYPE: PRT
<213> ORGANISM: Artificial sequence
<220> FEATURE:

<223> OTHER INFORMATION: Synthetic peptide

<400> SEQUENCE: 79

Ser Ser Asn Asn Phe Gly Ala Ile Leu Ser
1               5                   10

<210> SEQ ID NO 80
<211> LENGTH: 10
<212> TYPE: PRT
<213> ORGANISM: Artificial sequence
<220> FEATURE:
<223> OTHER INFORMATION: Synthetic peptide

<400> SEQUENCE: 80

Ser Asn Asn Phe Gly Ala Ile Leu Ser Ser
1               5                   10

<210> SEQ ID NO 81
<211> LENGTH: 10
<212> TYPE: PRT
<213> ORGANISM: Artificial sequence
<220> FEATURE:
<223> OTHER INFORMATION: Synthetic peptide

<400> SEQUENCE: 81

Asn Asn Phe Gly Ala Ile Leu Ser Ser Thr
1               5                   10

<210> SEQ ID NO 82
<211> LENGTH: 10
<212> TYPE: PRT
<213> ORGANISM: Artificial sequence
<220> FEATURE:
<223> OTHER INFORMATION: Synthetic peptide

<400> SEQUENCE: 82

Asn Phe Gly Ala Ile Leu Ser Ser Thr Asn
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic peptide

<400> SEQUENCE: 83

Phe Gly Ala Ile Leu Ser Ser Thr Asn Val
1               5                   10

<210> SEQ ID NO 84
<211> LENGTH: 10
<212> TYPE: PRT
<213> ORGANISM: Artificial sequence
<220> FEATURE:
<223> OTHER INFORMATION: Synthetic peptide

<400> SEQUENCE: 84

Gly Ala Ile Leu Ser Ser Thr Asn Val Gly
1               5                   10

<210> SEQ ID NO 85
<211> LENGTH: 10
<212> TYPE: PRT
<213> ORGANISM: Artificial sequence
<220> FEATURE:
<223> OTHER INFORMATION: Synthetic peptide

```
<400> SEQUENCE: 85

Ala Ile Leu Ser Ser Thr Asn Val Gly Ser
1               5                   10

<210> SEQ ID NO 86
<211> LENGTH: 10
<212> TYPE: PRT
<213> ORGANISM: Artificial sequence
<220> FEATURE:
<223> OTHER INFORMATION: Synthetic peptide

<400> SEQUENCE: 86

Ile Leu Ser Ser Thr Asn Val Gly Ser Asn
1               5                   10

<210> SEQ ID NO 87
<211> LENGTH: 10
<212> TYPE: PRT
<213> ORGANISM: Artificial sequence
<220> FEATURE:
<223> OTHER INFORMATION: Synthetic peptide

<400> SEQUENCE: 87

Leu Ser Ser Thr Asn Val Gly Ser Asn Thr
1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic peptide

<400> SEQUENCE: 88

Ser Ser Thr Asn Val Gly Ser Asn Thr Tyr
1               5                   10

<210> SEQ ID NO 89
<211> LENGTH: 8
<212> TYPE: PRT
<213> ORGANISM: Artificial sequence
<220> FEATURE:
<223> OTHER INFORMATION: Synthetic peptide

<400> SEQUENCE: 89

Asn Ala Gly Ala Ile Leu Ser Ser
1               5

<210> SEQ ID NO 90
<211> LENGTH: 10
<212> TYPE: PRT
<213> ORGANISM: Artificial sequence
<220> FEATURE:
<223> OTHER INFORMATION: Peptide array consensus sequence
<220> FEATURE:
<221> NAME/KEY: misc_feature
<222> LOCATION: (4)..(4)
<223> OTHER INFORMATION: Any amino acid, but cysteine

<400> SEQUENCE: 90

Ser Asn Asn Xaa Gly Ala Ile Leu Ser Ser
1               5                   10

<210> SEQ ID NO 91
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 91

Asn Ala Gly Ala Ile Leu Ser Ser
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic peptide

<400> SEQUENCE: 92

Asn Ala Gly Ala Ile Leu Ser Ser
1               5

<210> SEQ ID NO 93
<211> LENGTH: 8
<212> TYPE: PRT
<213> ORGANISM: Artificial sequence
<220> FEATURE:
<223> OTHER INFORMATION: Synthetic peptide

<400> SEQUENCE: 93

Asn Asp Gly Ala Ile Leu Ser Ser
1               5

<210> SEQ ID NO 94
<211> LENGTH: 8
<212> TYPE: PRT
<213> ORGANISM: Artificial sequence
<220> FEATURE:
<223> OTHER INFORMATION: Synthetic peptide

<400> SEQUENCE: 94

Asn Glu Gly Ala Ile Leu Ser Ser
1               5

<210> SEQ ID NO 95
<211> LENGTH: 8
<212> TYPE: PRT
<213> ORGANISM: Artificial sequence
<220> FEATURE:
<223> OTHER INFORMATION: Synthetic peptide

<400> SEQUENCE: 95

Asn Phe Gly Ala Ile Leu Ser Ser
1               5

<210> SEQ ID NO 96
<211> LENGTH: 8
<212> TYPE: PRT
<213> ORGANISM: Artificial sequence
<220> FEATURE:
<223> OTHER INFORMATION: Synthetic peptide

<400> SEQUENCE: 96

Asn Gly Gly Ala Ile Leu Ser Ser
1               5

<210> SEQ ID NO 97
<211> LENGTH: 8
<212> TYPE: PRT
<213> ORGANISM: Artificial sequence
```

```
<220> FEATURE:
<223> OTHER INFORMATION: Synthetic peptide

<400> SEQUENCE: 97

Asn His Gly Ala Ile Leu Ser Ser
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Asn Ile Gly Ala Ile Leu Ser Ser
1               5

<210> SEQ ID NO 99
<211> LENGTH: 8
<212> TYPE: PRT
<213> ORGANISM: Artificial sequence
<220> FEATURE:
<223> OTHER INFORMATION: Synthetic peptide

<400> SEQUENCE: 99

Asn Lys Gly Ala Ile Leu Ser Ser
1               5

<210> SEQ ID NO 100
<211> LENGTH: 8
<212> TYPE: PRT
<213> ORGANISM: Artificial sequence
<220> FEATURE:
<223> OTHER INFORMATION: Synthetic peptide

<400> SEQUENCE: 100

Asn Leu Gly Ala Ile Leu Ser Ser
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic peptide

<400> SEQUENCE: 101

Asn Met Gly Ala Ile Leu Ser Ser
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic peptide

<400> SEQUENCE: 102

Asn Asn Gly Ala Ile Leu Ser Ser
1               5

<210> SEQ ID NO 103
<211> LENGTH: 8
<212> TYPE: PRT
<213> ORGANISM: Artificial sequence
<220> FEATURE:
```

<223> OTHER INFORMATION: Synthetic peptide

<400> SEQUENCE: 103

Asn Pro Gly Ala Ile Leu Ser Ser
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Asn Gln Gly Ala Ile Leu Ser Ser
1               5

<210> SEQ ID NO 105
<211> LENGTH: 8
<212> TYPE: PRT
<213> ORGANISM: Artificial sequence
<220> FEATURE:
<223> OTHER INFORMATION: Synthetic peptide

<400> SEQUENCE: 105

Asn Arg Gly Ala Ile Leu Ser Ser
1               5

<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Asn Ser Gly Ala Ile Leu Ser Ser
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Asn Thr Gly Ala Ile Leu Ser Ser
1               5

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Asn Val Gly Ala Ile Leu Ser Ser
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 109

Asn Trp Gly Ala Ile Leu Ser Ser
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic peptide

<400> SEQUENCE: 110

Asn Tyr Gly Ala Ile Leu Ser Ser
1               5

<210> SEQ ID NO 111
<211> LENGTH: 6
<212> TYPE: PRT
<213> ORGANISM: Artificial sequence
<220> FEATURE:
<223> OTHER INFORMATION: Synthetic peptide

<400> SEQUENCE: 111

Asn Phe Gly Ala Ile Leu
1               5

<210> SEQ ID NO 112
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 112

Phe Phe Pro
1

<210> SEQ ID NO 113
<211> LENGTH: 4
<212> TYPE: PRT
<213> ORGANISM: Artificial sequence
<220> FEATURE:
<223> OTHER INFORMATION: Synthtic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (2)..(3)
<223> OTHER INFORMATION: D-Stereoisomer
<220> FEATURE:
<221> NAME/KEY: misc_feature
<222> LOCATION: (4)..(4)
<223> OTHER INFORMATION: D and L methyl alanine

<400> SEQUENCE: 113

Xaa Phe Asn Xaa
1

<210> SEQ ID NO 114
<211> LENGTH: 4
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 114

Xaa Asn Phe Xaa
1

<210> SEQ ID NO 115
<211> LENGTH: 2
<212> TYPE: PRT
<213> ORGANISM: Artificial sequence
<220> FEATURE:
<223> OTHER INFORMATION: Synthetic peptide

<400> SEQUENCE: 115

Tyr Tyr
1

<210> SEQ ID NO 116
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: amidated amino acid

<400> SEQUENCE: 116

Tyr Tyr
1

<210> SEQ ID NO 117
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine

<400> SEQUENCE: 117

Xaa Phe Phe
1

<210> SEQ ID NO 118
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: D and L methyl alanine

<400> SEQUENCE: 118

Asn Tyr Xaa
1
```

```
<210> SEQ ID NO 119
<211> LENGTH: 3
<212> TYPE: PRT
<213> ORGANISM: Artificial sequence
<220> FEATURE:
<223> OTHER INFORMATION: Synthetic peptide

<400> SEQUENCE: 119

Asn Tyr Pro
1

<210> SEQ ID NO 120
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 120

Asn Tyr Pro
1

<210> SEQ ID NO 121
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer
<220> FEATURE:
<221> NAME/KEY: misc_feature
<222> LOCATION: (2)..(2)
<223> OTHER INFORMATION: D and L methyl alanine

<400> SEQUENCE: 121

Tyr Xaa
1

<210> SEQ ID NO 122
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 122

Pro Tyr
1

<210> SEQ ID NO 123
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
```

```
<223> OTHER INFORMATION: D-Stereoisomer

<400> SEQUENCE: 123

Tyr Pro
1

<210> SEQ ID NO 124
<211> LENGTH: 6
<212> TYPE: PRT
<213> ORGANISM: Artificial sequence
<220> FEATURE:
<223> OTHER INFORMATION: Synthetic peptide

<400> SEQUENCE: 124

Ala Asn Phe Leu Val His
1               5

<210> SEQ ID NO 125
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 125

Xaa Asn Phe Xaa Val His
1               5

<210> SEQ ID NO 126
<211> LENGTH: 5
<212> TYPE: PRT
<213> ORGANISM: Artificial sequence
<220> FEATURE:
<223> OTHER INFORMATION: Synthetic peptide

<400> SEQUENCE: 126

Ala Asn Phe Leu Val
1               5

<210> SEQ ID NO 127
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 127

Xaa Asn Phe Xaa Val
1               5

<210> SEQ ID NO 128
<211> LENGTH: 3
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 128

Phe Phe Pro
1

<210> SEQ ID NO 129
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: D-Stereoisomer
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 129

Xaa Phe Asn Xaa
1

<210> SEQ ID NO 130
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 130

Phe Asn Pro
1

<210> SEQ ID NO 131
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 131

Xaa Asn Phe Xaa
1

<210> SEQ ID NO 132
<211> LENGTH: 6
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 132

Gln Lys Leu Val Phe Phe
1               5

<210> SEQ ID NO 133
<211> LENGTH: 2
<212> TYPE: PRT
<213> ORGANISM: Artificial sequence
<220> FEATURE:
<223> OTHER INFORMATION: Synthetic peptide

<400> SEQUENCE: 133

Tyr Tyr
1

<210> SEQ ID NO 134
<211> LENGTH: 4
<212> TYPE: PRT
<213> ORGANISM: Artificial sequence
<220> FEATURE:
<223> OTHER INFORMATION: Synthetic peptide

<400> SEQUENCE: 134

Asn Tyr Tyr Pro
1

<210> SEQ ID NO 135
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 135

Tyr Tyr Xaa
1

<210> SEQ ID NO 136
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 136

Xaa Tyr Tyr
1
```

```
<210> SEQ ID NO 137
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 137

Xaa Tyr Tyr Xaa
1

<210> SEQ ID NO 138
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer
<220> FEATURE:
<221> NAME/KEY: misc_feature
<222> LOCATION: (4)..(4)
<223> OTHER INFORMATION: D-Stereoisomer

<400> SEQUENCE: 138

Asn Tyr Tyr Pro
1

<210> SEQ ID NO 139
<211> LENGTH: 3
<212> TYPE: PRT
<213> ORGANISM: Artificial sequence
<220> FEATURE:
<223> OTHER INFORMATION: Synthetic peptide

<400> SEQUENCE: 139

Pro Tyr Tyr
1

<210> SEQ ID NO 140
<211> LENGTH: 3
<212> TYPE: PRT
<213> ORGANISM: Artificial sequence
<220> FEATURE:
<223> OTHER INFORMATION: Synthetic peptide

<400> SEQUENCE: 140

Tyr Tyr Pro
1

<210> SEQ ID NO 141
<211> LENGTH: 4
<212> TYPE: PRT
<213> ORGANISM: Artificial sequence
<220> FEATURE:
<223> OTHER INFORMATION: Synthetic peptide

<400> SEQUENCE: 141

Pro Tyr Tyr Pro
1
```

-continued

<210> SEQ ID NO 142
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 142

Tyr Tyr
1

<210> SEQ ID NO 143
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 143

Pro Xaa
1

<210> SEQ ID NO 144
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 144

Phe Pro
1

<210> SEQ ID NO 145
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 145

Trp Xaa
1

<210> SEQ ID NO 146
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)

```
<223> OTHER INFORMATION: D-Stereoisomer

<400> SEQUENCE: 146

Trp Pro
1

<210> SEQ ID NO 147
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer

<400> SEQUENCE: 147

Phe Pro
1

<210> SEQ ID NO 148
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: D-Stereoisomer

<400> SEQUENCE: 148

Pro Phe
1

<210> SEQ ID NO 149
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 149

Cys Trp Xaa
1

<210> SEQ ID NO 150
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: D-Stereoisomer
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 150
```

```
Cys Trp Xaa
1

<210> SEQ ID NO 151
<211> LENGTH: 5
<212> TYPE: PRT
<213> ORGANISM: Artificial sequence
<220> FEATURE:
<223> OTHER INFORMATION: Synthetic peptide

<400> SEQUENCE: 151

Asp Ala Asn Lys Ala
1               5

<210> SEQ ID NO 152
<211> LENGTH: 37
<212> TYPE: PRT
<213> ORGANISM: Rattus norvegicus
<220> FEATURE:
<221> NAME/KEY: misc_feature
<223> OTHER INFORMATION: Islet amyloid polypeptide (iapp) partial
      sequence

<400> SEQUENCE: 152

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 153
<211> LENGTH: 37
<212> TYPE: PRT
<213> ORGANISM: Homo sapiens
<220> FEATURE:
<221> NAME/KEY: misc_feature
<223> OTHER INFORMATION: Islet amyloid polypeptide (iapp) partial
      sequence

<400> SEQUENCE: 153

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 154
<211> LENGTH: 7
<212> TYPE: PRT
<213> ORGANISM: Artificial sequence
<220> FEATURE:
<223> OTHER INFORMATION: Synthetic peptide

<400> SEQUENCE: 154

Asn Phe Gly Ser Val Gln Phe
1               5

<210> SEQ ID NO 155
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 155

Asn Phe Gly Ser Val Gln Phe Val
1               5

<210> SEQ ID NO 156
<211> LENGTH: 8
<212> TYPE: PRT
<213> ORGANISM: Artificial sequence
<220> FEATURE:
<223> OTHER INFORMATION: Synthetic peptide

<400> SEQUENCE: 156

Asn Phe Gly Ser Val Gln Phe Ala
1               5

<210> SEQ ID NO 157
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 157

Xaa Asn Phe Xaa Val His Ser Ser
1               5

<210> SEQ ID NO 158
<211> LENGTH: 32
<212> TYPE: PRT
<213> ORGANISM: Homo sapiens
<220> FEATURE:
<221> NAME/KEY: misc_feature
<223> OTHER INFORMATION: Human calcitonin

<400> SEQUENCE: 158

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 159
<211> LENGTH: 4
<212> TYPE: PRT
<213> ORGANISM: Artificial sequence
<220> FEATURE:
<223> OTHER INFORMATION: Synthetic peptide

<400> SEQUENCE: 159

Gly Ala Ile Leu
1

<210> SEQ ID NO 160
<211> LENGTH: 5
<212> TYPE: PRT
<213> ORGANISM: Artificial sequence
<220> FEATURE:
<223> OTHER INFORMATION: Synthetic peptide

<400> SEQUENCE: 160
```

Lys Leu Val Phe Phe
1               5

<210> SEQ ID NO 161
<211> LENGTH: 7
<212> TYPE: PRT
<213> ORGANISM: Artificial sequence
<220> FEATURE:
<223> OTHER INFORMATION: Synthetic peptide

<400> SEQUENCE: 161

Lys Leu Val Phe Phe Ala Glu
1               5

<210> SEQ ID NO 162
<211> LENGTH: 8
<212> TYPE: PRT
<213> ORGANISM: Artificial sequence
<220> FEATURE:
<223> OTHER INFORMATION: Synthetic peptide

<400> SEQUENCE: 162

Asn Phe Gly Ser Val Gln Phe Val
1               5

<210> SEQ ID NO 163
<211> LENGTH: 7
<212> TYPE: PRT
<213> ORGANISM: Artificial sequence
<220> FEATURE:
<223> OTHER INFORMATION: Synthetic peptide

<400> SEQUENCE: 163

Gly Asn Asn Gln Gln Asn Tyr
1               5

<210> SEQ ID NO 164
<211> LENGTH: 38
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: Human IAPP derived polypeptide

<400> SEQUENCE: 164

Met Lys Cys Asn Thr Ala Thr Cys Ala Thr Gln Arg Leu Ala Asn Phe
1               5                   10                  15

Leu Val His Ser Ser Asn Asn Phe Gly Ala Ile Leu Ser Ser Thr Asn
            20                  25                  30

Val Gly Ser Asn Thr Tyr
        35

<210> SEQ ID NO 165
<211> LENGTH: 114
<212> TYPE: DNA
<213> ORGANISM: Artificial sequence
<220> FEATURE:
<223> OTHER INFORMATION: A synthetic polynucleotide coding for a human
      IAPP derived polypeptide

<400> SEQUENCE: 165
atgaaatgca acaccgcgac ctgcgcgacc cagcgcctgg cgaactttct ggtgcatagc      60
agcaacaact ttggcgcgat tctgagcagc accaacgtgg gcagcaacac ctat          114

```
<210> SEQ ID NO 166
<211> LENGTH: 114
<212> TYPE: DNA
<213> ORGANISM: Homo sapiens
<220> FEATURE:
<221> NAME/KEY: misc_feature
<223> OTHER INFORMATION: Human IAPP coding  partial cDNA

<400> SEQUENCE: 166
atgaaatgca acactgccac atgtgcaacc cagcgcctgg caaattttt agttcattcc       60 agcaacaact ttggtgccat tctctcatct accaacgtgg gatccaatac atat           114
```